(12) United States Patent
Yu et al.

(10) Patent No.: US 9,861,319 B2
(45) Date of Patent: Jan. 9, 2018

(54) NONCONTACT THREE-DIMENSIONAL DIFFUSE OPTICAL IMAGING OF DEEP TISSUE BLOOD FLOW DISTRIBUTION

(71) Applicant: University of Kentucky Research Foundation, Lexington, KY (US)

(72) Inventors: Guoqiang Yu, Lexington, KY (US); Yu Lin, Lexington, KY (US); Chong Huang, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 72 days.

(21) Appl. No.: 15/078,403

(22) Filed: Mar. 23, 2016

(65) Prior Publication Data

US 2016/0278715 A1    Sep. 29, 2016

Related U.S. Application Data

(60) Provisional application No. 62/136,707, filed on Mar. 23, 2015.

(51) Int. Cl.
*A61B 5/026* (2006.01)
*A61B 5/00* (2006.01)
(Continued)

(52) U.S. Cl.
CPC .......... *A61B 5/7275* (2013.01); *A61B 5/0075* (2013.01); *A61B 5/0091* (2013.01);
(Continued)

(58) Field of Classification Search
CPC .................................................. A61B 5/0075
See application file for complete search history.

(56) References Cited

U.S. PATENT DOCUMENTS

| 5,075,561 A | 12/1991 | Rioux |
| 6,370,422 B1 | 4/2002 | Richards-Kortum et al. |

(Continued)

FOREIGN PATENT DOCUMENTS

| CN | 103163111 A | 6/2013 |
| WO | 2012053908 | 4/2012 |

OTHER PUBLICATIONS

Lin, et al., Noncontact diffuse correlation spectroscopy for noninvasive deep tissue blood flow measurement, Journal of Biomedical Optics, Jan. 2012 • vol. 17(1).

(Continued)

*Primary Examiner* — Kennedy Schaetzle
(74) *Attorney, Agent, or Firm* — King & Schickli, PLLC

(57) ABSTRACT

The present invention provides for three-dimensional reflectance diffuse optical imaging of deep tissue blood flow distribution that removes the need for probe-tissue contact, thereby allowing for such technology to be applied to sensitive, vulnerable, damaged, or reconstructive tissue. The systems utilize noncontact application and detection of near-infrared light through optical lens and detection through a linear array or two-dimensional array of avalanche photodiodes or a two-dimensional array of detectors provided by charge-coupled-device (CCD). Both further feature a finite-element-method (FEM) based facilitation to provide for three-dimensional flow image reconstruction in deep tissues with arbitrary geometries.

11 Claims, 34 Drawing Sheets

(51) Int. Cl.
G06F 17/50 (2006.01)
G01N 21/17 (2006.01)
(52) U.S. Cl.
CPC .......... *A61B 5/0261* (2013.01); *A61B 5/7282* (2013.01); *G06F 17/50* (2013.01); *A61B 5/0073* (2013.01); *A61B 5/708* (2013.01); *A61B 5/7214* (2013.01); *G01N 2021/1787* (2013.01)

(56) References Cited

U.S. PATENT DOCUMENTS

| | | | |
|---|---|---|---|
| 7,235,047 | B2 | 6/2007 | MacAulay et al. |
| 7,242,997 | B2 | 7/2007 | Geng |
| 7,460,248 | B2 | 12/2008 | Kurtz et al. |
| 8,000,775 | B2 | 8/2011 | Pogue et al. |
| 8,353,830 | B2 | 1/2013 | Kanayama et al. |
| 8,563,932 | B2 | 10/2013 | Fang et al. |
| 8,712,504 | B2 | 4/2014 | Godavarty et al. |
| 9,036,970 | B2 | 5/2015 | Guyon et al. |
| 2006/0063995 | A1* | 3/2006 | Yodh .................... A61B 5/0059 600/323 |
| 2009/0234225 | A1 | 9/2009 | Martin et al. |
| 2009/0240139 | A1 | 9/2009 | Yi |
| 2010/0094134 | A1 | 4/2010 | Zhu et al. |
| 2010/0168586 | A1 | 7/2010 | Hillman et al. |
| 2010/0309457 | A1* | 12/2010 | Cui ....................... G01J 9/0215 356/121 |
| 2013/0044185 | A1 | 2/2013 | Krishnaswamy et al. |
| 2014/0236003 | A1 | 8/2014 | Hielscher et al. |

OTHER PUBLICATIONS

Yu, Diffuse Correlation Spectroscopy (DCS): A Diagnostic Tool for Assessing Tissue Blood Flow in Vascular-Related Diseases and Therapies, Current Medical Imaging Reviews, 2012,8, 194-210.
Boas, et al., Spatially varying dynamical properties of turbid media probed with diffusing temporal light correlation, J. Opt. Soc. Am. A/ vol. 14, No. 1/Jan. 1997.
Zhou, et al., Diffuse optical correlation tomography of cerebral blood flow during cortical spreading depression in rat brain, Optics Express 14, 1125-1144 (2006).
Lin, et al., Three-dimensional flow contrast imaging of deep tissue using noncontact diffuse correlation tomography, AIP Applied Physics Letters, 104, 121103 (2014).
Dehghani, et al., Near infrared optical tomography using NIRFAST: Algorithm for numerical model and image reconstruction, Commun. Numer. Meth. Engng (2008).
Fercher, et al., Flow Visualization by Means of Single-Exposure Speckle Photography, Optics Communications, vol. 37, No. 5, Jun. 1981.
Bi, et al., Deep tissue flowmetry based on diffuse speckle contrast analysis, May 1, 2013 / vol. 38, No. 9 / Optics Letters, 1401-1403.
Valdes, et al., Speckle contrast optical spectroscopy, a non-invasive, diffuse optical method for measuring microvascular blood flow in tissue, Biomedical Optics Express, vol. 5, No. 8, Aug. 2014.
Varma, et al., Speckle contrast optical tomography: A new method for deep tissue three-dimensional tomography of blood flow, Biomedical Optics Express, vol. 5, No. 4, Apr. 2014.
Boas, et al., Laser speckle contrast imaging in biomedical optics, Journal of Biomedical Optics 15(1), 011109Jan./Feb. 2010.
Bandyopadhyay, et al., Speckle-visibility spectroscopy: A tool to study time-varying dynamics, Rev. Sci. Instrum. 76, 093110 (2005).
Ruyten, W., Smear correction for frame transfer charge-coupled-device cameras, Optics Letters, vol. 24, No. 13, 878-880, Jul. 1, 1999.
Yuan, S., Sensitivity, Noise and Quantitative Model of Laser Speckle Contrast Imaging, dissertation, 2008.
Irwin, et al., Influences of tissue absorption and scattering on diffuse correlation spectroscopy blood flow measurements, Jul. 1, 2011 / vol. 2, No. 7 / Biomedical Optics Express.
Yuan, et al., Determination of optimal exposure time for imaging of blood flow changes with laser speckle contrast imaging, Applied Optics, vol. 44, No. 10 Apr. 2005.
Ripoll, et al., Free-Space Propagation of Diffuse Light: Theory and Experiments, Physical Review Letters, vol. 91, No. 10, 2003.
Zhang, et al., Design of an optical system consisting of a special telecentric lens for side-scattering measurement on individual cells, Optical Engineering 49(5) 053001 May 2010.
Watanabe, et al., Telecentric Optics for Focus Analysis, IEEE Transactions on Pattern Analysis and Machine Intelligence, vol. 19, No. 12, Dec. 1997.
English machine translation of CN103163111.

* cited by examiner (a)

(b)

NONCONTACT THREE-DIMENSIONAL DIFFUSE OPTICAL IMAGING OF DEEP TISSUE BLOOD FLOW DISTRIBUTION

RELATED APPLICATIONS

This application claims priority to U.S. Provisional Application 62/136,707, filed Mar. 23, 2015, which is hereby incorporated by reference in its entirety.

GOVERNMENT SUPPORT

This invention was made with government support under grants R21-AR062356 and UL-1RR033173 Pilot Grant awarded by the National Institutes of Health. The government may have certain rights in the invention.

FIELD OF THE INVENTION

The present invention relates to the application of diffuse correlation tomography (DCT) through both noncontact (ncDCT) and charge-coupled-device (CCD)-based noncontact speckle contrast (nc_scDCT) approaches for three-dimensional (3-D) reflectance imaging of deep tissue (up to 1.5 cm depth) to better assess any potential tissue injury therein.

BACKGROUND

The ability to image within diseased or sensitive tissue is highly desirable as it provides further information as to the underlying health of the tissue, but remains problematic in successful execution due to accessing the tissue without touching the surface. Significant problems with contact measurements (using a probe in contact with tissue) include the risk for infection of vulnerable tissues (e.g., wounds, burns, reconstructive tissue flaps) and the deformation of soft tissues (e.g., breasts) distorting blood flow and oxygenation.

Chronic wounds affect over 5 million Americans each year, resulting in over $20 billion in health care costs. Individuals with disabilities and diabetes as well as the elderly have the highest risk of developing chronic wounds. Patients afflicted with chronic wounds suffer from physical pain and disabilities in addition to psychological and emotional stresses and poor quality of life. Current treatments for chronic wounds include cleansing, debridement, maintaining a moist tissue environment, and when possible, eliminating the underlying pathology or factors that contributed to poor wound healing. In advanced cases, amputation may become necessary. Death, especially in elderly patients, may result from sepsis that can be associated with chronic wounds. Multiple factors can lead to impaired wound healing. Local factors that influence healing include tissue blood flow and oxygenation. Pressure ulceration, For example, occurs when the skin and underlying tissues are compressed for a period of time between the bone and the surface on which the patient is sitting or lying. Constant pressure against the tissue reduces blood supply to that area which results in tissue ischemia[1, 2]. Ultrasound imaging results have recently shown that early pressure ulcers originate from deep tissues attached to the bone and spread upwards, eventually to the skin[3]. Therefore, quantification of blood flow in deep wound tissues is crucial for accurate diagnosis and treatment monitoring.

As another example of tissue injury, a burn is damage to body's tissues caused by heat, chemicals, electricity, sunlight or radiation. Burns can cause swelling, blistering, scarring and, in serious cases, shock and even death. They also can lead to infections because they damage skin's protective barrier. Treatment for burns depends on the cause of the burn, how deep it is, and how much of the body it covers. Antibiotic creams can prevent or treat infections. For more serious burns, treatment may be needed to clean the wound, replace the skin, and make sure the patient has enough fluids, nutrition, blood flow, and tissue oxygen.

As a further example, mastectomy skin flap necrosis may ultimately lead to implant exposure, infection and implant loss. In some of these cases, the complications may be so devastating as to cause a failure of reconstruction[4,5,6]. Of the 75,000 expander-implant based reconstructions performed in 2013, more than 18,000 resulted in implant loss, secondary to complications[7]. The cost of implant loss alone is >$30,000[8], plus the fees incurred by additional operating room time, clinic visits, inpatient stays, surgeon costs and procedure fees.

Similarly, head and neck cancer accounts for 3 to 5% of all cancers in the United States[9]. Despite all the advances in non-surgical treatments, surgery remains an important tool in the management of these cancers. Primary or salvage surgeries are extensive and often lead to major head and neck defects that require complex reconstructions with local flaps, regional flaps, or free tissue transfer flaps. Intraoperative decreases in blood flow after flap anastomosis have been observed[10,11], which may lead to failure of flap thrombosis.

Thus, knowledge of tissue blood flow changes after tissue transfer may enable surgeons to predict the failure of flap thrombosis at an early stage to salvage ischemic flaps.

Current imaging diagnostic tools include x-ray computed tomography (CT), magnetic resonance imaging (MRI), positron emission tomography (PET) and ultrasonography, but most of these imaging methods are prohibitively expensive and generally only provide tissue morphological information. Moreover, some of these techniques (e.g., CT and PET) expose patients to ionizing radiation[12,13]. Doppler ultrasound is limited in measuring only blood flow in large vessels.

Often, the surface of a tissue does not provide sufficient feedback as to the health of the tissue within. For example, when flap ischemia is a concern, most surgeons rely primarily on careful and frequent visual examination of the flap surface. Several tools and techniques are currently in use to monitor flaps in order to detect changes in viability in a time frame that allows for salvage of the flap from its nonviable state. While transcutaneous or implantable ultrasound Doppler technologies are commonly used to assess blood flow through large axial vessels, peripheral flap blood flow remains largely subjective in its clinical assessment[11,27-29]. Laser Doppler technique has also been used to monitor blood flow at a tiny spot of superficial tissue, which may not reflect precisely hemodynamic changes in the bulk flap tissue[10,30,31]. The ischemia and hypo-perfusion that can occur intra-operatively in the flap are often not evident to the surgeons until days/weeks later when it presents as skin flap necrosis. Therefore, clinical assessment alone is not reliable. For example, mastectomy skin flap necrosis, infection and implant loss are all interlinked by a shortfall of perfusion and tissue oxygen at the microcirculatory level. Previously, a prospective clinical trial of tissue expander-implant breast reconstruction has been conducted with intraoperative evaluation of mastectomy skin flaps by clinical assessment, laser-assisted indocyanine green dye angiography, and fluorescein dye angiography[32]. Due to the requirement of an intravenous injection, these methods lack feasibility for continuous use in clinical preoperative and postoperative settings; and they are time-dependent, requiring evaluation after a particular time period following dye injection. Thus, noninvasive, continuous, and quantitative imaging methods are highly advantageous to assess tissue hemodynamic states and alterations for perioperative management flap ischemia to reduce the likelihood of postoperative ischemic complications.

Near-infrared (NIR: 650 nm to 900 nm) diffuse optical technologies provide a noninvasive and relatively inexpensive tool for functional imaging of tissue hemodynamics in deep microvasculature up to several centimeters[14-17]. The most commonly used NIR diffuse optical spectroscopy/tomography (DOS/DOT) can currently quantify tissue hemoglobin concentration and blood oxygen saturation. Traditional DOS/DOT using the fiber-optic interface has been used over several decades to detect distribution of oxygenation alternations in tissues[18-22].

A relatively new NIR diffuse correlation spectroscopy (DCS) technique has been also developed for direct measurement of blood flow in deep tissues (up to ~1.5 cm)[23,24]. DCS employs coherent NIR light to probe deep tissues and single-photon-counting avalanche photodiodes (APDs) to detect temporal speckle fluctuations of the diffuse light on tissue boundaries. Long-coherence lasers and APD detectors are connected with optical fibers placed on the tissue boundary for DCS measurements. The measured temporal speckle fluctuation depends on the motion of moving scatterers (primarily red blood cells in the microvasculature), which is related to a blood flow index (BFI). BFI can be quantified by iteratively fitting the measured light intensity autocorrelation function.

Despite advances in DCS technologies, there have been limited imaging applications of diffuse correlation tomography (DCT). A probe-tissue contact based DCS/DCT approach has been described, but as with other approaches it remains disadvantaged in vivo due in part to compression-induced hemodynamic alterations or potential infections on ulcerous tissues. Another limitation lies in their reliance on analytical solutions that assumed a simple semi-infinite flat tissue geometry. Thus, an approach without the request of contact measurement may address these limitations.

SUMMARY OF THE INVENTION

The present invention provides systems and methods for three-dimensional (3-D) reflectance imaging of blood flow distribution in deep tissue. The systems offer an approach that avoids contact with the subject being imaged, thereby offering systems that allow for imaging of sensitive, supple or diseased tissue. The imaging can be achieved of depths of 1.5 cm or less. The systems and methods provide for projecting and focusing an imaging probe on to a tissue surface of a subject. The imaging probe may comprise source fibers connected to long-coherence lasers that emit near-infrared (NIR) light. The systems and methods further comprise a detector array also projected and focused on the tissue. The imaging probe may then apply beams of NIR light through a set of optical lenses to the tissue and the detector array to detect the diffused NIR light from the tissue through a second set of optical lenses. An image may then be constructed based on measured diffused near-infrared light transporting from the source fibers through the tissue to the detector array.

The systems and methods provide in part for the detector array to be at least one linear array of photodiodes. In other parts, the detector array may comprise a two-dimensional (2-D) array of photodiodes. In yet further parts, the detector array may comprise a 2-D array detectors provided by a charge-coupled-device (CCD). In instances where the detector array is linear, coupling the imaging probe to a motorized stage allows the probe to be systematically and automatically moved across a region of interest of the tissue.

In aspects where the detector array comprises a 2-D CCD, the NIR light can be applied through at least four source fibers to borders of a region of interest of a tissue of a subject with the CCD detecting near-infrared diffused light through an optical lens coupled to a CCD. Contact with the subject can be avoided by either connecting the source fibers with optical lenses or by applying the light through a Galvo mirror.

The present invention also provides in part for computing systems to construct a 3-D flow image from collected data. The computing systems may execute a finite-element-method (FEM) based facilitation of detected unnormalized electric field autocorrelation function, $G_1(r,\tau) = \langle E(r, t)E^*(r, t+\tau)\rangle$, by applying the data set to an adapted correlation diffusion equation of $\nabla \cdot ((D(r)/v)\nabla G_1(r,\tau)) - (\mu_a(r) + \frac{1}{3}\mu_s'(r) k_0^2 \alpha \langle \Delta r^2(\tau)\rangle)G_1(r,\tau) = -S(r)e^{i2\pi c/\lambda}$ where r is the position vector and v is the light speed in the medium. $\mu_a(r)$ is the medium absorption coefficient, and $D(r) \approx v/3\mu_s'(r)$ is the medium photon diffusion coefficient, $\mu_s'(r)$ is the medium reduced scattering coefficient, $\tau$ is autocorrelation delay time, c is speed of light in vacuum, and $\lambda$ is wavelength and $(r,) = \frac{1}{3}\mu_s'(r)k_0^2\alpha\langle \Delta r^2(\tau)\rangle$ as a dynamic absorption with $k_0$ as the wave number of an incident light field, $\alpha$ is the unitless ratio of dynamic scatterers to total (dynamic and static) scatterers. $\langle \Delta r^2(\tau)\rangle$ is the mean-square displacement in time $\tau$ of the moving scattering particles (e.g., red blood cells); for the case of diffuse motion, $\langle \Delta r^2(\tau)\rangle = 6D_B(r)\tau$ where $D_B(r)$ (unit: $cm^2/s$) is an effective diffusion coefficient of the moving scatterers; and then redefining $\mu_a^d(r,\tau) = 2\mu_s'(r) k_0^2\alpha D_B(r)\tau$ then extracting $\alpha D_B(r)$ as blood flow index that can collectively be compiled with multiple blood flow indices measured at difference source-detector (S-D) pairs to construct an image. In instances where an obtained data set may comprise a measured spatial speckled contrast K (such as by a CCD), these data may be first converted to a blood flow index across each of S-D pair prior to extracting $\alpha D_B(r)$. Such can be accomplished by relating K to the normalized temporal autocorrelation function $g_1$ by $K^2 = 2\beta/T\int_0^T(1-\tau/T)[g_1(r,\tau)]^2 d\tau$, where $\beta$ relates detector and speckle size. This is then followed by identifying a nonlinear relationship by $K^2 = f(\alpha D_B, T, \mu_a, \mu_s', \lambda, \beta, S-D, k_0)$, and, finally minimizing $(K^2-f)^2$ to obtain the blood flow index.

The present invention also provides in part for creating a 3D solid model of the tissue being imaged by first acquiring autocorrelation functions at each measurement location of the S-D array; and then acquiring a surface geometry of the tissue with a 3-D camera that includes the boundaries of the region of interest. Following such, a solid tissue model may be created with arbitrary surface from the captured surface image with a 3-D CAD enabled alignment system. On the tissue model, the sources and detectors from the S-D array on the model can then be aligned which allows for 3-D reconstruction of blood flow index distribution from autocorrelation function measurements.

DETAILED DESCRIPTION

Figure 1:
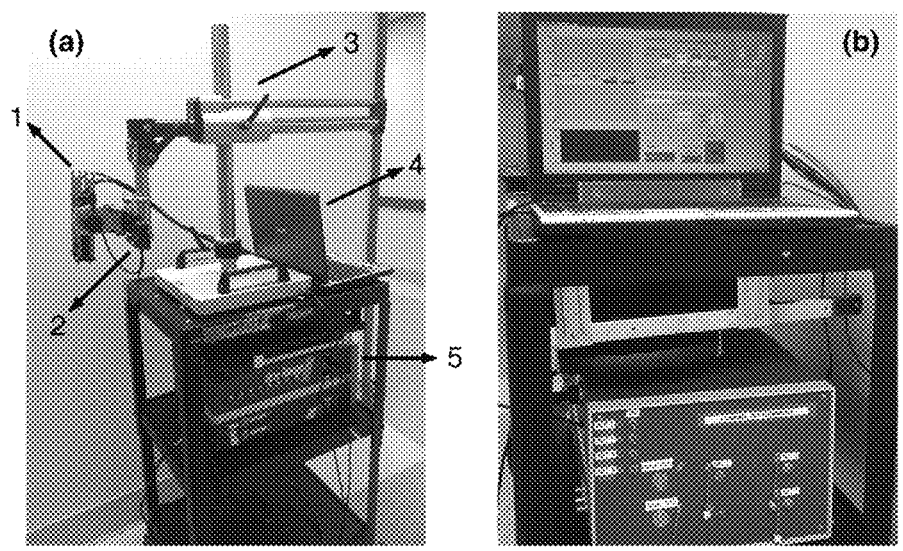
FIG. 1 shows (a) the custom-made noncontact diffuse correlation spectroscopy (ncDCS) system including (1) a noncontact optical probe, (2) a linear motorized stage, (3) a multiple-axis stand holder, (4) a laptop control panel, and (5) a ncDCS device and (b) the front view of ncDCS device.

The present invention concerns improvements in the fields of diffuse correlation spectroscopy (DCS) and diffuse correlation tomography (DCT). The present invention described herein provides for noncontact DCS (ncDCS), noncontact DCT (ncDCT), speckled contrast DCT (scDCT) and noncontact speckle contrast DCT (nc_scDCT) systems and methods of using such for deep tissue flow measurements without probe-tissue contact, as well as novel approaches to creating a reconstructed 3-D image of blood flow distributions from data collected by these systems through a modification to the finite-element-method (FEM)-based 3-D image reconstruction (originally designed for DOT). The FEM-based image reconstruction allows for the recovery of blood flow distributions in deep tissues with arbitrary geometries. Both of these physical systems incorporate core DCS/DCT technology as set forth U.S. Pat. No. 8,082,015 (which is hereby incorporated by reference in its entirety). Briefly DCS/DCT employs coherent near infrared (NIR) light to probe deep tissues and single-photon-counting avalanche photodiodes (APDs) to detect temporal speckle fluctuations of the diffuse light on tissue boundaries. Long-coherence lasers and APD detectors are connected with optical fibers placed on the tissue boundary for contact DCS/DCT measurements. The measured temporal speckle fluctuation depends on the motion of moving red blood cells in the microvasculature (i.e. blood flow). By contrast, diffuse speckled contrast imaging utilizes a charge-coupled-device (CCD) to detect spatial speckle contrasts of the diffuse light throughout the tissue.

Both ncDCT and nc_scDCT systems deliver and detect NIR light through optical lenses to the surface of a tissue, thereby removing the previously required need to be in contact with the tissue. The ncDCT, which features avalanche photodiode (APD) detection, and the nc_scDCT process, which features CCD detection, are distinguished by the transition from temporal to spatial diffuse speckle intensity fluctuations. NIR light ranging from 650 to 900 nm is generated by a coherent laser with the power of ~100 mw. The ncDCT approach uses a limited number of expensive but highly sensitive APDs to detect temporal diffuse speckle fluctuations for blood flow measurement, which limits the system's spatial-temporal resolution and increases instrumentation cost and dimension. With a linear array of APDs in the ncDCT, coverage of the ROI is achieved by mechanically scanning the probe over the ROI for complete coverage, which can take tens of minutes. By contrast, the nc_scDCT approach uses a CCD to detect spatial diffuse speckle contrasts for blood flow measurement. Hundreds of detectors provided by a CCD unit omit the probe scanning phase and significantly improve the spatial and temporal resolution. Further, the CCD detection used in the nc_scDCT allows for higher temporal (a few seconds) and spatial resolution (1 to 2 mm) as well as lower cost and smaller dimension of the instrument, compared to the APDs used in the ncDCT. Further still, single-photon-counting APDs used in ncDCT are more sensitive (but more expensive) than the CCD detection. Both systems are discussed independently below.

With the systems described herein, the present invention further provides, in part, for detecting and imaging blood flow within a deep tissue. Through the type of detector utilized (e.g., via APDs or CCD), tissue can be imaged from the surface to approximately 1.5 cm depth within the tissue. The tissue can be any tissue that is exposed such that NIR light may be applied, such as a naturally exposed tissue, e.g., skin or during a surgical procedure or through the opening of a generated surgical flap.

The present invention similarly provides methods for assessing and monitoring a tissue. Those skilled in the art will appreciate that the systems described herein can obtain an image at any time that an image is desired. For example, using the systems described herein, an image may be obtained before, during and after surgical procedures to determine the success of a procedure, to obtain a diagnosis, or to review or follow a course of treatment. Those skilled in the art will appreciate that the only limitation to obtaining an image of a tissue is access to the tissue such that the system can provide the requisite light.

The present invention further provides systems that can measure or assess multiple parameters within a tissue. As described herein, application of NIR light allows for the detection and assessment of blood flow with a tissue. High-resolution imaging with multiple functional outputs has the potential to guide the creation of more refined treatment strategies that incorporate knowledge of heterogeneities to yield higher intervention efficacy. NIR diffuse optical/fluorescence tomography (DOT/DFT) has gained great interest as a fast, portable, and inexpensive technology for functional blood oxygenation tomography (DOT) or fluorescence concentration tomography (DFT). Through utilizing multiple optical sources and fiber optical switches connected to NIR lasers at different wavelengths (e.g., 785 nm and 830 nm), other parameters such as tissue blood oxygenation or fluorescence (with optical filters) can also be detected. Thus, through incorporating these other imaging methodologies within the systems described herein, a hybrid DOT/DFT/DCT system with nc or sc feature is achieved. Such other detected parameters may then be independently imaged or overlaid with one or more measured parameters (see, e.g. He et al., J. Biomed. Optics. 18: 037001 (2013) and Shang et al., Optics Lett. 34: 3556-3558 (2009)).

Hardware Advancements

All systems discussed improve on limitations in application of the DCS/DCT technology (U.S. Pat. No. 8,082,015, which is hereby incorporated by reference in its entirety). Presented herein are several advancements in the apparatus required for successfully obtaining a desired 3-D image of blood flow distribution in deep tissue noninvasively. The advancements feature the development of noncontact (nc)

systems for APD-based DCT and the development of CCD-based DCT (i.e., speckled contrast (sc) DCT). As discussed herein, these advancements can be integrated to a DCS/DCT system in several ways.

Figure 2:
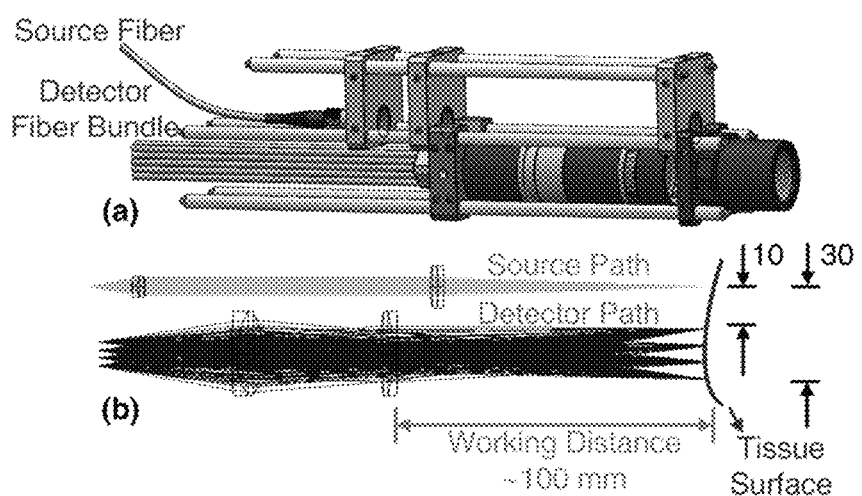
FIG. 2 shows (a) the mechanical configuration and (b) optical paths of ncDCS probe. The source and detector fibers are innovatively projected through separated lens paths onto the tissue surface, which avoids cross-talk between light delivery and detection.

The present invention therefore provides, in part, for systems and methods of using such that are capable of producing a DCT image without contacting the tissue being imaged. As shown in FIGS. 1 and 2, a DCS system that avoids contact with a tissue (the ncDCS apparatus depicted) is a simple spectroscopic version of a DCT system (as described herein) with limited numbers of sources and detectors.

Figure 3:
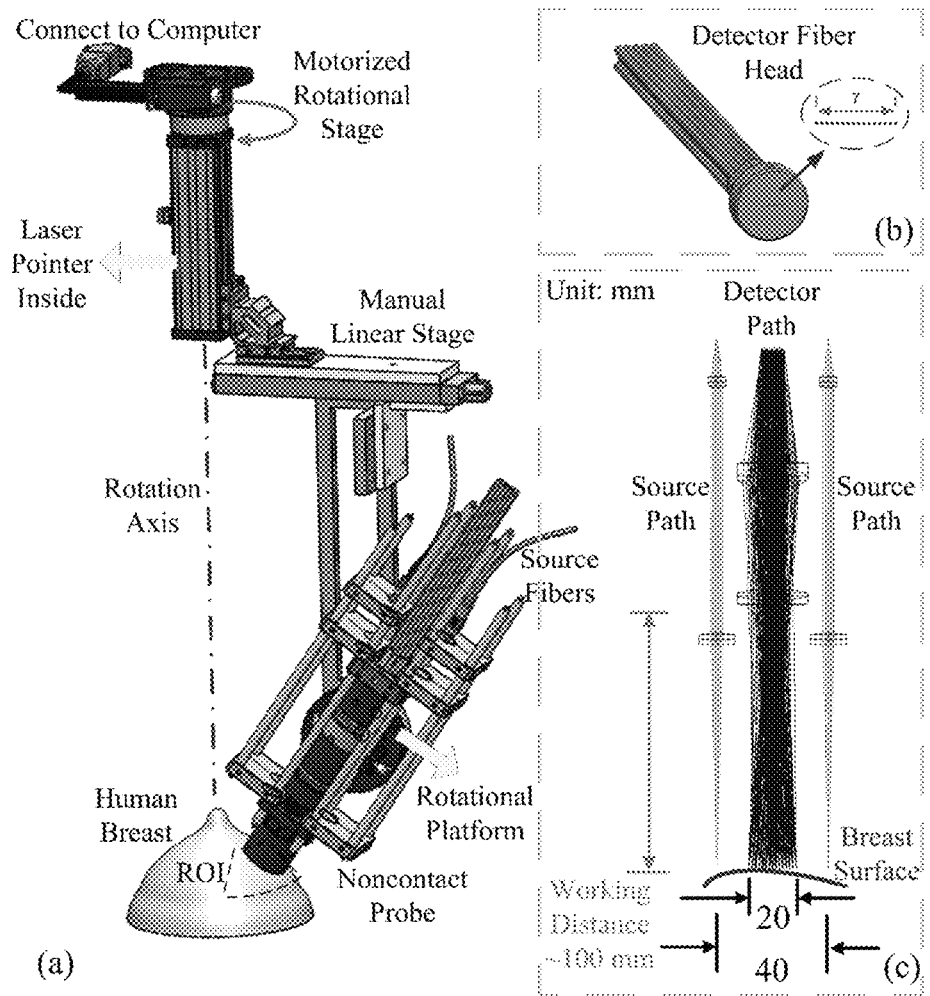
FIG. 3 shows schematic diagram of a noncontact diffuse correlation tomography (ncDCT) with rotational scanning system. (a) A motorized rotational stage was used to remotely scan over a representative region of interest (ROI) on a breast. A laser pointer was used to align the rotation axis approximately through the nipple. The relative position between the ncDCT probe and ROI (i.e., working distance, initial step of scanning) can be adjusted manually by the linear stage and the rotational platform. (b) Fifteen single-mode detector fibers connected with APDs were equally arranged in a 7 mm line to cover a 20 mm range through the magnification of lenses. (c) The source and detector fibers were projected on the breast surface using achromatic lenses. Two source paths projecting two coherent NIR lasers (785 nm) were attached to the sides of the detector path.
Figure 4:
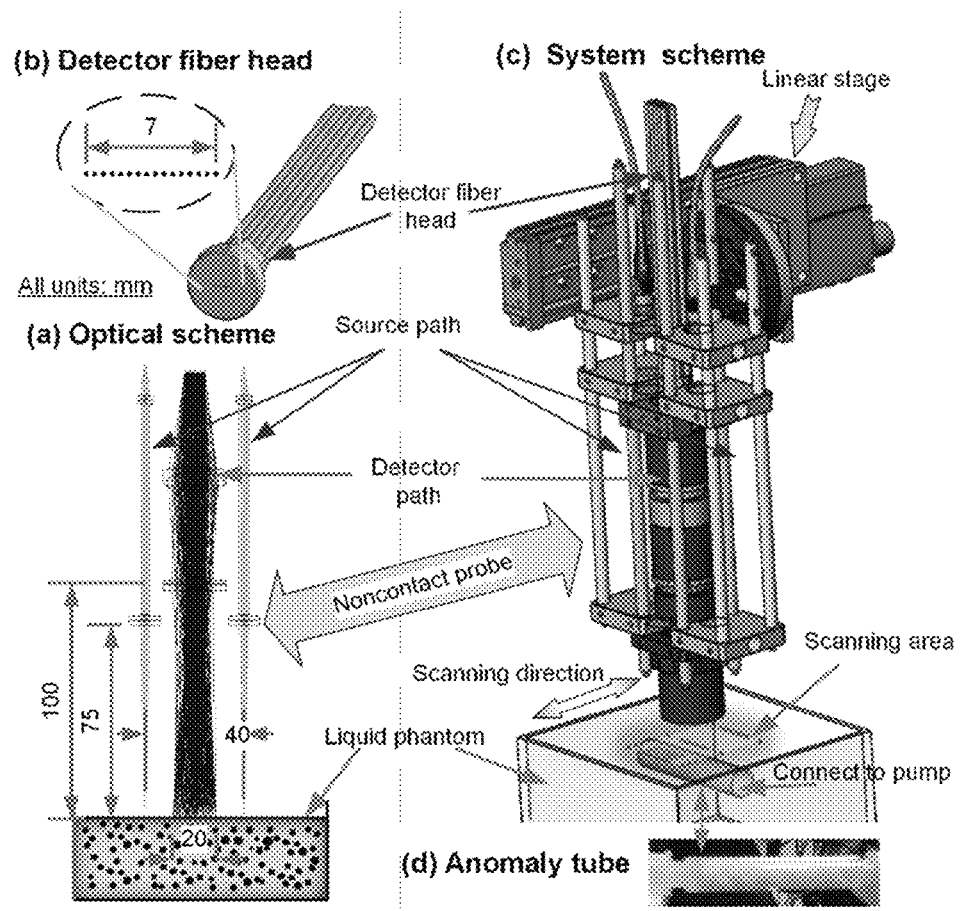
FIG. 4 shows an illustration of (a) the ncDCT focusing apparatus with photon projections to and from a sample, (b) linear array of single-mode detector fibers, (c) motorized linear scanning staging over a representative ROI, and (d) the pump-connected cylindrical tube-shaped anomaly in a tank filled with Intralipid liquid solution.

FIGS. 3 and 4, depict two examples of a noncontact DCT (ncDCT) apparatus that allows for noncontact 3-D imaging of tissue blood flow distributions. These apparati feature a noncontact imaging probe comprised of source fibers to provide NIR light, such as through connection to connected long-coherence lasers and a detector head that features an array of detector fibers. The probe can be positioned within or around a region of interest to be imaged and near infrared light is applied through the source fibers and to the tissue surface through a set of optical lenses. Following diffusion through the tissue, the detector fibers detect the diffused light, via a second set of optical lenses, which in turn allows for measurement of the diffused light traveled through the tissue. As set forth in FIGS. 3 and 4, such systems allow for obtaining data without having the system contact the tissue or even the subject being imaged. As described herein, the detector array can vary from a linear array to a 2-D array. Further, the ncDCT system can be connected to motorized stages such that it can scan over the region of interest (ROI) either rotationally (FIG. 3) or linearly (FIG. 4) to achieve a composite of multiple scans for 3-D image reconstruction. Such an approach, provides a somewhat lengthy sampling time (~ tens of minutes) but reducing the cost (e.g., using less sources and detectors). By contrast, a ncDCT system that features a 2D array of APDs does not require scanning, thereby reducing the sampling time (~ a few seconds) but increasing instrumentation cost and dimension by requiring more sources and detectors.

Figure 5:
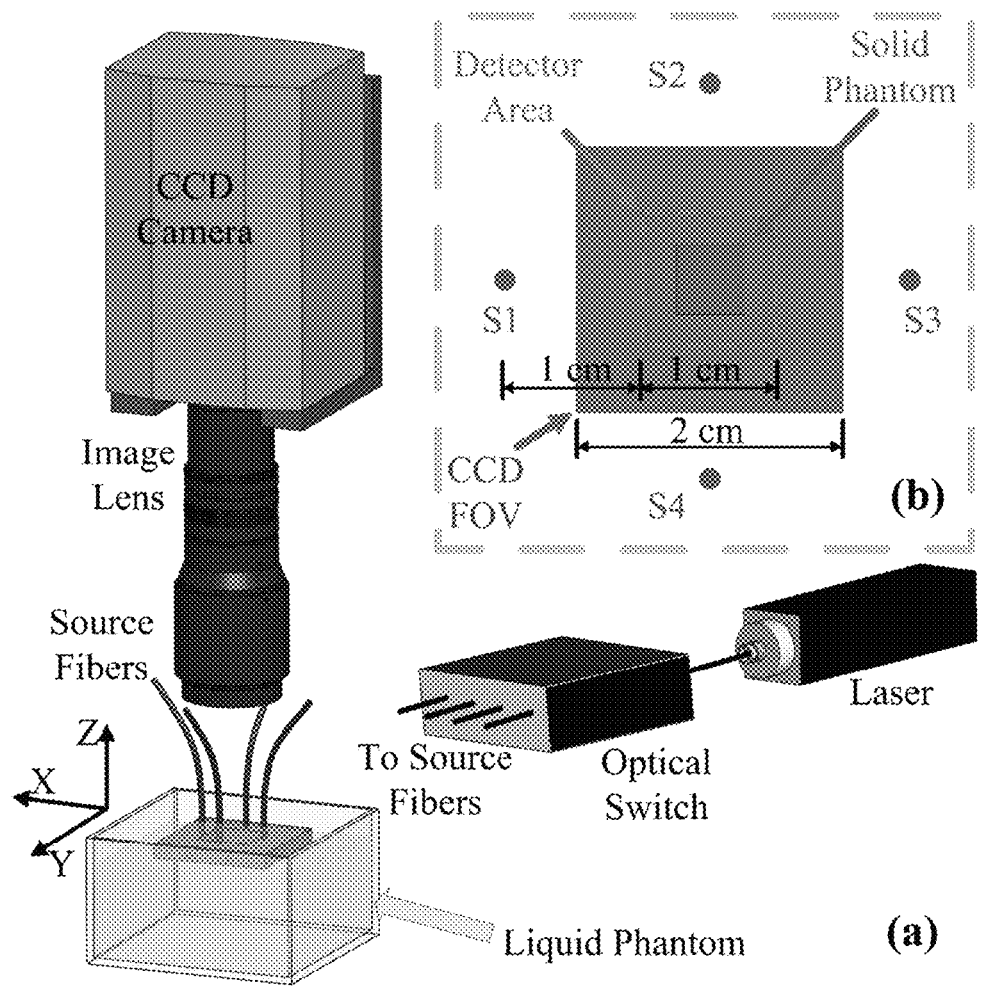
FIG. 5 shows the setup for testing a charge-coupled device (CCD)-based speckle contrast diffuse correlation tomography (scDCT) system for 3-D flow imaging. (a) The CCD is focused onto a liquid phantom surface. A square metal holder positioned four fibers supporting their ferrule tips on the liquid surface. The holder provided a 2.4 cm×2.4 cm open area. The optical switch distributed laser light into the four source fibers sequentially. (b) Configuration of the four sources, CCD field of view (FOV), solid phantom placement, and detector area.
Figure 6:
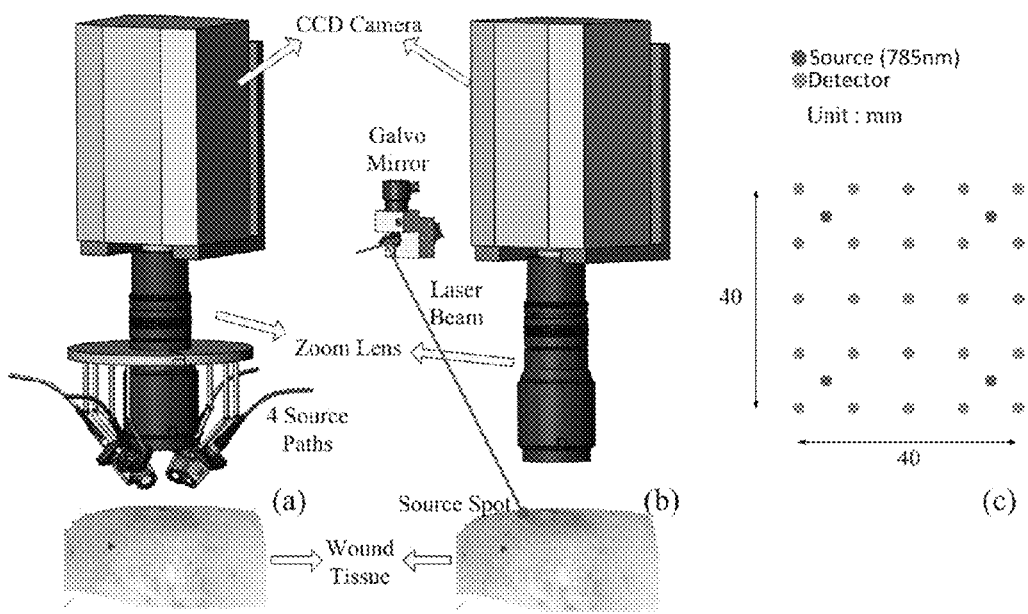
FIG. 6 shows a CCD-based fully noncontact scDCT (nc_scDCT) system using separated sources (a) or Gavano mirror (b) based sources for imaging of flow contrast. (c) A typical source-detector distribution pattern.

The present invention further provides, in part, for systems and methods of using such that detect spatial speckle intensity fluctuations in diffused NIR light. These spatial speckled contrast advancements feature the introduction of a charge-coupled-device (CCD) as the detector array within the system, thereby providing a 2-D detector array capable of rapidly acquiring a 3D image. As seen in FIGS. 5 and 6, the scDCT and nc_scDCT systems provide for semi-noncontact or noncontact reflectance 3-D imaging of tissue blood flow distributions. The scDCT system shown in FIG. 5 is a semi-noncontact system (sources are still contacting the tissue, primarily at the perimeter or boundary of the region of interest to be imaged with the CCD detector not in contact with the tissue), whereas the nc_scDCT system shown in FIG. 6 is a fully noncontact system that utilizes different approaches for providing the sources that do not require contact (e.g. multiple sources arranged around the CCD or through redirection by a Galvo mirror).

Finite-Element-Method (FEM) Based Facilation of ncDCT Image Reconstruction

The present invention also provides for new algorithms, software and computing systems incorporating such that facilitate the processing of data generated by the imaging systems discussed herein. Specifically, FEM-based algorithms for DOT are innovatively modified for the accomplishment of DCT in tissues with arbitrary boundaries. The present invention further incorporates systems that execute the advancements in 3-D image reconstruction, as well as that integrate with other operations to render such images.

In DOT theory, the detected photon fluence rate $\Phi(r,\omega)$ in highly scattering media such as biological tissues obeys the frequency-domain photon diffusion equation $$\nabla \cdot ((D(r)/v)\nabla \Phi(r,\omega)) - (\mu_a(r)+i\omega/v)\Phi(r,\omega) = -S(r,\omega) \quad (1)$$

where r is the position vector and v is the light speed in the medium. $\mu_a(r)$ is the medium absorption coefficient, and $D(r) \approx v/3\mu_s'(r)$ is the medium photon diffusion coefficient where $\mu_s'(r)$ is the medium reduced scattering coefficient. (r, $\omega$) is the isotropic source term modulated at angular frequency $\omega$. The measurements use a point source continuous-wave (CW) approach ($\omega=0$). In DCT theory, focus is on the unnormalized electric field autocorrelation function, $G_1(r,\tau) = \langle E(r,t)E^*(r,t+\tau) \rangle$, obeying a formally similar CW diffusion equation for DOT:

$$\nabla \cdot ((D(r)/v)\nabla G_1(r,\tau)) - (\mu_a(r) + \tfrac{1}{3}\mu_s'(r)k_0^2\alpha \langle \Delta r^2(\tau) \rangle)G_1(r,\tau) = -S(r)e^{j(2\pi c/\lambda)} \quad (2)$$

where r is the position vector and v is the light speed in the medium. $\mu_a(r)$ is the medium absorption coefficient, and $D(r) \approx v/3\mu_s'(r)$ is the medium photon diffusion coefficient, $\mu_s'(r)$ is the medium reduced scattering coefficient, $\tau$ is autocorrelation delay time, c is speed of light in vacuum, and $\lambda$ is wavelength. In practice, only the modulus is considered with the right-hand side then resembling Eq. 1 in CW form (i.e., $-S(r)$). Next is written $\mu_a^d(r,\tau) = \tfrac{1}{3}\mu_s'(r)k_0^2\alpha\langle \Delta r^2(\tau)\rangle$, having the same unit as $\mu_a(r)$ and stemming from the common referral to $\tfrac{1}{3}\mu_s'(r)k_0^2\alpha\langle \Delta r^2(\tau)\rangle$ (i.e. $\nabla \cdot ((D(r)/v)\nabla G_1(r,\tau)) - (\mu_a(r)+\mu_a^d(r,\tau))G_1(r,\tau) = -S(r)e^{j(2\pi c/\lambda)}$) as the "dynamic absorption" of correlation with delay time $\tau$ due to dynamic processes. $k_0$ is the wave number of the incident light field. $\alpha$ is the unitless ratio of dynamic scatterers to total (dynamic and static) scatterers. $\langle \Delta r^2(\tau)\rangle$ is the mean-square displacement in time $\tau$ of the moving scattering particles (e.g., red blood cells); for the case of diffuse motion, $\langle \Delta r^2(\tau) \rangle = 6D_B(r)\tau$ where $D_B(r)$ (unit: cm$^2$/s) is an effective diffusion coefficient of the moving scatterers. Thus, the dynamic absorption is redefined to $\mu_a^d(r,) = 2\mu_s'(r)k_0^2\alpha D_B(r)\tau$. The combined term $\alpha D_B(r)$ is referred to as the blood flow index in tissues and can be extracted by fitting the analytical solution of Eq. 2.

Proper algorithms for the forward/inverse solutions to Eq. 2 can therefore be employed to reconstruct flow index contrast. The FEM framework has been applied to model light transportation in comprehensive diffuse media to resolve the geometry and heterogeneity limitations for DOT. Exploiting the high mathematical similarity of the forward and inverse problems (e.g., boundary condition and mathematical assumptions) between DOT (Eq. 1) with CW source and DCT (Eq. 2), the application of FEM in DCT is achieved. This concept is introduced into the FEM-based light transport and image reconstruction modules from NIR-FAST as a shortcut for FEM implementation. NIRFAST is a publically available image reconstruction package based on the diffusive model and FEM method for DOT. DCT then can be conceptualized as a formulation of DOT which with CW computes $G_1(r,\tau)$ instead of $\Phi(r,\omega)$, by updating $\mu_a(r)$ to $\mu_a(r)+\mu_a^d(r,\tau)$, and reconstructing $\mu_a(r)+\mu_a^d(r,\tau)$ instead of $\mu_a(r)$ only. The correlation function can be simulated using multiple delay times and combining all $G_1(\tau)$ along the time sequence $\tau$. Reconstructed $(r)+\mu_a^d(r,\tau)$ then enables extracting the flow index $\alpha D_B(r)$ through the definition of $\mu_a^d(r,\tau)$. As a result, the realm of DCT becomes available for comprehensive imaging under arbitrary geometries and optical properties.

Image reconstruction from spatial speckled contrast systems (e.g. scDCT/nc_scDCT) can similarly be achieved as FEM-based ncDCT. For a certain CCD camera exposure time, T, the spatial speckle contrast, K, is defined as the ratio of the standard deviation, σ, to mean, μ, intensities across pixels in a chosen window (e.g. 7×7), i.e., K=σ/μ. Using the Siegert relationship, this spatial speckle contrast parameter K can be related to the normalized temporal electric field autocorrelation function g1 by $$K^2 = 2\beta/T \int_0^T (1-\tau/T)[g_1(r,\tau)]^2 d\tau \quad (3)$$

where β relates detector and speckle size. We substitute in the form of g1 from the analytical solution to Eq. 1 for semi-infinite geometry and find a nonlinear relationship between speckle contrast and BFI, i.e., $K^2 = f(\alpha D_B, T, \mu_a, \mu_s', \lambda, \beta, S\text{-}D, k_0)$ where S-D is source-detector separation. We then minimize the squared difference between the experimentally measured speckle contrast and theoretical result, $(K^2-f)^2$, with respect to extracting the blood flow index (BFI). These calculated BFI's are then representative of the boundary measurements for insertion into the modified NIRFAST program as developed previously for FEM-based ncDCT blood flow reconstructions.

The present invention further provides a smear correction algorithm that can be employed to correct point-source illumination contributions during image capture with the frame transfer CCD and reflectance measurement setup. Briefly, the speckle contrast obtained from a frame transfer CCD camera may be deviated from the theoretical presence by intensity disorder from the frame transfer process. More specifically, visual stripes (smears) can be induced extending from bright features in the image into the direction opposite that of the charge transfer process. Along this direction, the smear can be corrected using an algorithm described by Eq. 4. The actual pixel intensity signal of the $x^{th}$ column and $y^{th}$ row (x,y) can be restored by the measured value i'(x,y) with $$i(x,y) = i'(x,y) - \eta t_{ft}/n_p T \sum_{n=1}^{y-1} i(x,n) \quad (4)$$

where $t_{ft}$ is frame transfer time, $n_p$ is number of pixel rows when the frame has moved to the readout buffer, and η is the efficiency with which photoelectrons are generated during the charge-transfer process relative to the efficiency with which photoelectrons are generated during the image capture period. In the examples herein, the CCD frame transfer time is ~1 ms with set 7×7 windows at the same distance to the source location for a symmetric intensity distribution, leading to η value of 0.67.

Preprocessing of raw CCD images is required as follows. Spatial speckle contrast contributions due to hardware noise (i.e., shot noise and dark noise) are accounted for correcting the speckle contrast computation, $K_{meas}=(\sigma/\mu)$, of windowed regions. Briefly, dark images are used to mitigate speckle contrast influences from dark noise, $I_C=I-I_D$, where I is the original intensity of a single pixel and $I_D$ is the intensity of dark current. The shot noise of $I_C$ follows Poisson statistics, $(I_C)=\sqrt{(I_C)}$, which are incorporated into the correction calculation. The shot and dark corrected speckle contrast is then given by $$K = \sqrt{\frac{\sigma^2(I) - \sigma^2(I_D) - \sigma_S^2(I_C)}{\mu^2(I_C)}}. \quad (5)$$

Noncontact DCS/DCT

The present invention provides in part for noncontact measurement methodologies (ncDCS/ncDCT) for the characterization of tissue blood flow within deep tissue. FIGS. 1 and 2 show a possible apparatus arrangement for a ncDCS system that provides measurements of deep tissue blood flow without contacting the tissue. NIR diffuse correlation spectroscopy (DCS) has recently emerged as a highly advantageous blood flow monitoring modality, but requires contact-based interaction with the sample or tissue being examined. Such contact measurements can promote hemodynamic variations induced by compression or disturb sensitive areas.

The present invention provides an apparatus and a method of utilizing DCT without contact (ncDCT) for 3-D flow imaging of deep tissue (FIGS. 3 and 4). The present invention addresses the disadvantages associated with contact-based DCT systems, partially through a motorized stage for automated and customizable ROI scanning capabilities. The invention further provides a finite-element-method (FEM) based facilitation of DCT image reconstruction of blood flow distribution, which may be integrated into other systems, such as an open software package for diffuse optical tomography (DOT) termed NIRFAST. Validation of the system is demonstrated herein through computer simulations and a phantom testing design allowing flow variations.

The present invention provides a noncontact probe that utilizes at least two identical laser source paths and at least one detector path for ncDCT (FIGS. 3 and 4). The source fiber applies NIR light through the first set of optical lenses to the tissue and the detector senses the applied light after it has diffused through the tissue. In each source path, output from a multimode fiber connected to a laser is projected onto the tissue phantom surface through lenses. The numbers of source and detector paths can be varied as needed. A detector fiber head in the detector path contains single-mode fibers equally arranged in a line covering a pre-determined range though lenses at desired working distance. The photons traveling through the sample are collected by a detector array of APDs through the detector path. The array may be linear or multi-linear. A multi-channel autocorrelator board takes the APD outputs and simultaneously calculates the temporal autocorrelation functions for each of S-D pairs. Another facet provides the integration of a motorized stage for automatic and precise ROI scanning through probe translation.

FIGS. 3 and 4 show a possible apparatus arrangement for a ncDCT system that provides 3-D imaging of deep tissue blood flow distribution without contacting the tissue. Two sets of optical lenses project source and detector fibers respectively onto the tissue surface. The separation of source and detector paths then allows for the arrangement of large source-detector distances (up to 3 cm), thus providing for probing deep tissues up to ~1.5 cm depth. This noncontact design allows for noninvasive hemodynamic assessment of tissues, such as ulcerous tissues, which overcome the contact limitations (e.g., the infection of wounds). Further, as depicted in FIGS. 3 and 4, a linear array of APDs (e.g., 15 APDs) and two laser sources connected to a mobile lens-focusing system provide automatic and noncontact scanning of flow in a region of interest (ROI). These boundary measurements can then be combined with a FEM-based facilitation of ncDCT image reconstruction for arbitrary tissue geometry (as discussed herein), which can be then pioneered and integrated into a system, such as the open software package NIRFAST that was designed originally for DOT[34]. Initial validation efforts for the innovative ncDCT system have been made using computer simulations, tissue phantoms, mammary tumors, and ulcerous tissues (see also EXAMPLES section herein).

Figure 13:
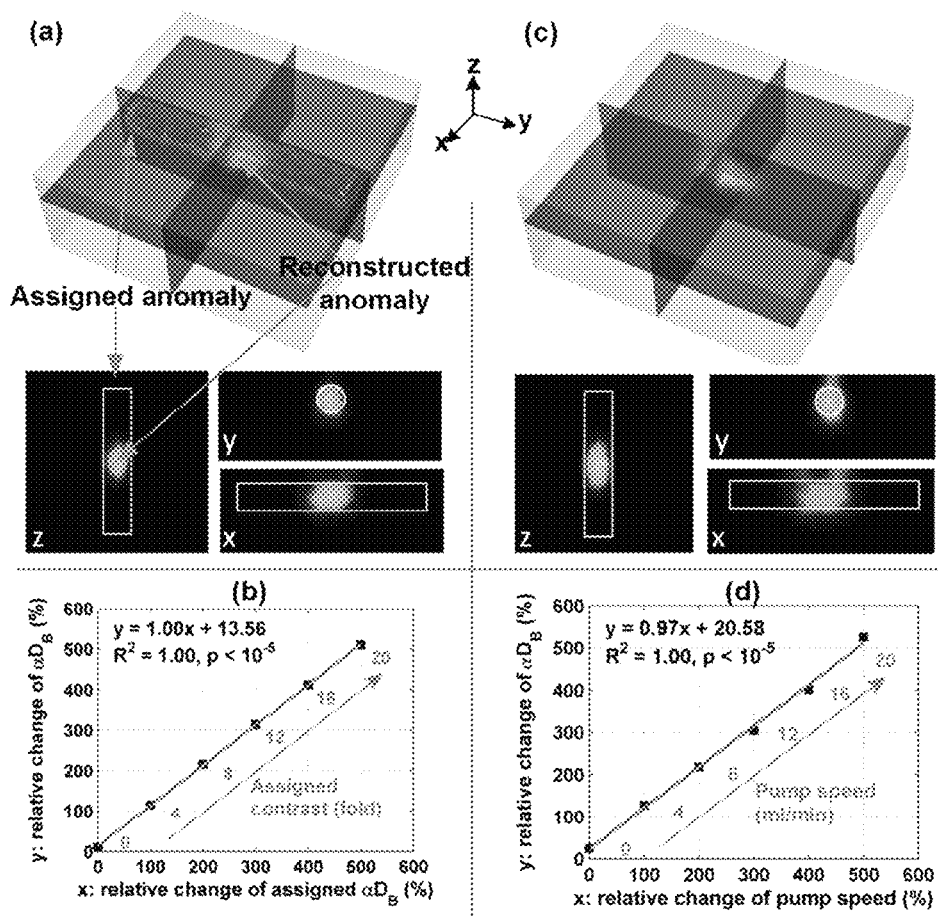
FIG. 13 shows results of computer simulations and phantom experiments measured by ncDCT on a homogeneous slab background and internally placed tube-shaped anomaly of varied flow contrast. The reconstructed anomaly from the last step with highest flow contrast is shown (a) 3-D overlaid on the assigned anomaly and two-dimensional (2-D) cross-section views (x, y, z) in the simulation and (c) in the phantom experiment. Both (b) and (d) show a linear relationship between the assigned anomaly and reconstructed flow indices expressed as ratios of relative changes respectively in the simulation and phantom experiment.
Figure 14:
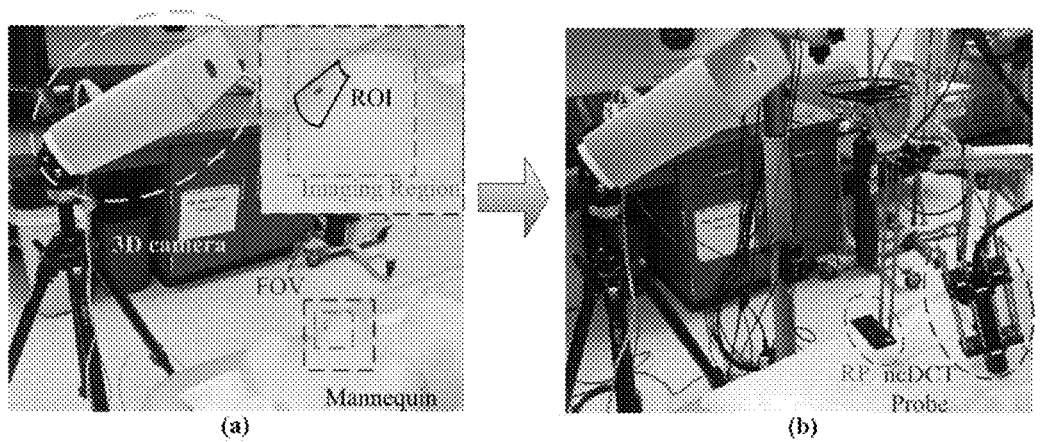
FIG. 14 shows a 3-D camera to obtain surface images of the breast and reference plane (RP) for ncDCT image reconstruction. (a) The breast surface with source marks was imaged by the 3-D camera. An "imaging region" (~5"×5"), displayed in the inset, was selected inside the FOV for generating the solid breast model (see FIG. 32). (b) After the mannequin was removed, a small foam pad was attached to the ncDCT scanner. The 3-D camera took another image to include the small foam pad whose surface (RP) was adjusted perpendicularly to the rotation axis. The RP was used for the coregistration of two coordinate systems: 3-D camera and ncDCT.

FIG. 13 provides examples of application of this ncDCT in computer simulations and using a tissue-like phantom with anomaly flow contrast design[33]. The cylindrical tube-shaped anomaly was clearly reconstructed in both simulation and phantom arrangements. Recovered and assigned flow contrast changes in anomaly were found to be highly correlated. These results exhibit application of ncDCT for 3-D imaging of deep tissue blood flow heterogeneities.

The ncDCT imaging system has also successfully been utilized on mammary tumors in human subjects (FIGS. 14 to 27)[35]. ncDCT scanning procedures across the ROI (e.g., a breast tumor), similar to those described in the phantom experiments except that the breast tumor was scanned using a rotational probe around the nipple. The breast tumors were first determined by ultrasound imaging, then scanned by the ncDCT probe. After DCT data acquisition, another scanning was done with a commercial 3-D photogrammetric camera (NextEngine, CA, USA) producing a boundary surface with corresponding marks. This surface was extended into a solid model using SolidWorks® and S-D locations were aligned on the model surface (see, e.g., EX. 3 herein). This solid model was next converted to a solid mesh in ANSYS®. The mesh and S-D spatial coordinates were then finally input into the modified NIRFAST software enabling 3-D tomographic reconstruction of blood flow contrast[36-38].

Figure 10:
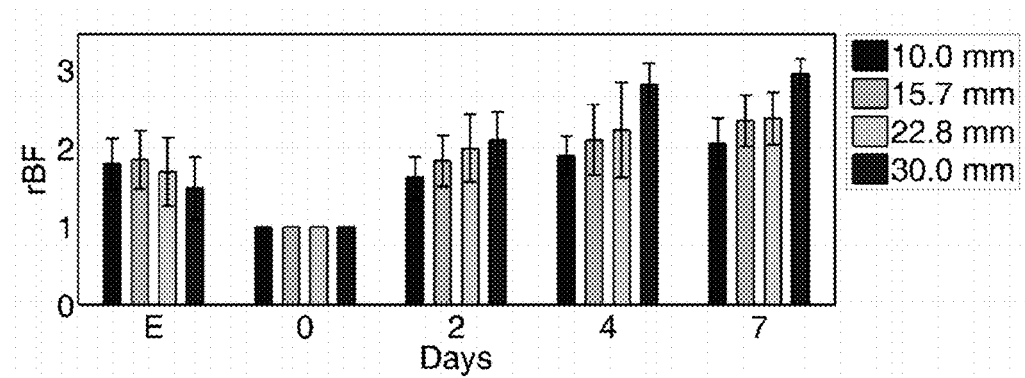
FIG. 10 shows Averaged rBF data measured by ncDCS at four S-D separations in all successful cases over seven days. Error bars represent standard errors over subjects.
Figure 11:
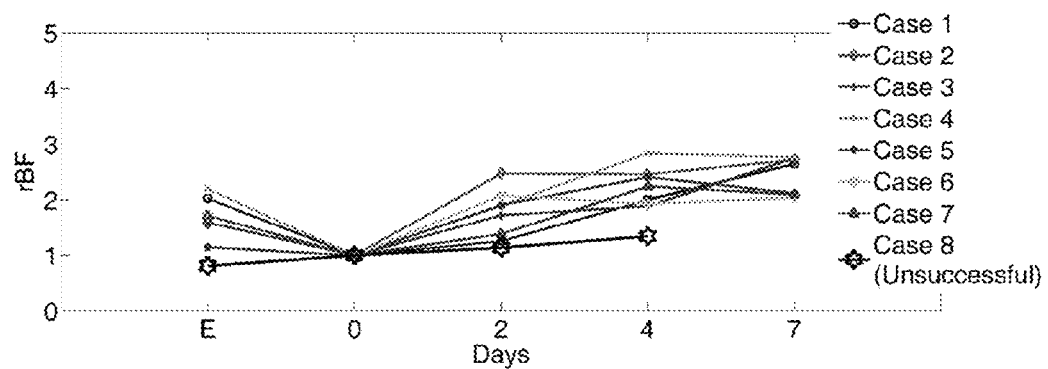
FIG. 11 shows the rBF data measured by ncDCS from all flap cases (cases 1 to 8) including the unsuccessful one (case 8) highlighted with large hexagrams. Note that data from the unsuccessful case (case 8) at day 7 are not available due to the subsequent re-flap before that day. The error bars (see FIG. 13) for individual cases are not shown for clarity

To further investigate the application of the noncontact systems, the ncDCS system has been examined on free tissue transfer flaps where eight free flaps were elevated in patients with head and neck cancer (see FIGS. 7-12, EX. 1 herein)[39]. Multiple measurements probing the same region of the transferred tissue were continually performed before and during surgery as well as on postoperative days. Postoperative blood flow values were normalized to the intraoperative baselines (assigning '1') for the calculation of relative BFI change (rBF). FIG. 11 shows the results from all eight cases including seven successes (Cases 1 to 7) and one failure (Case 8). Interestingly, rBF changes/recoveries in the unsuccessful flap during and post vessel anastomosis were found to be smaller than all successful flaps, suggesting the potential of ncDCT measurements for early prediction of ischemic flaps.

2-D Source-Detector Array

The ncDCT system discussed above primarily concerns a linear array of photodiodes to detect diffused NIR light. Such a linear array can be systematically moved across a region of interest to capture data set for 3D flow image. Those skilled in the art will appreciate that using a 2-D detector array that obtains data along two axes at once removes or reduces the need to move the detector array. While the mechanical scanning of a linear S-D fiber array in ncDCT to cover a ROI provides a way to increase sampling density and reduce cost, these approaches involve increases in the time required for measurement and may be therefore prone to the presence of motion artifacts. The present invention therefore further provides for modification of the ncDCT system that features a 2-D replacement of the linear APD array (e.g. 2-D array of APDs, such as 15×15 APDs), alleviating ROI scanning and cutting the acquisition time from tens of minutes to a few seconds to minutes. Those skilled in the art will appreciate that the number of APDs (both in length and width of the detector array) present can be adjusted to accommodate the region of interest.

CCD-Based Speckle Contrast Diffuse Correlation Tomography (scDCT)

The present invention further provides for a 2-D detector array comprised of a charge-coupled-device (CCD) that also allows for data acquisition along 2 axes, thereby removing or reducing the need to move the capturing detectors to obtain data for the region of interest. An adjustable zoom lens is used to adapt a ROI with different areas. The CCD-based spatial diffuse speckle contrast DCT (scDCT) apparatus and method of use thereof combines the benefits of CCD detection with the FEM-based DCT flow reconstruction discussed herein. Hundreds of S-D pairs provided by the CCD allow one skilled in the art to omit a probe scanning phase, significantly improving the spatial and temporal resolution, and reduce equipment complication, dimension, and cost.

Application to reflectance tomographic imaging is provided by the present invention through the development of a robust technique that combines the benefits of CCD detection and FEM-based DCT flow reconstruction[41-43]. The imaging process can be simplified by converting the speckle contrast to boundary flow indices and retaining the leverage of FEM-based DCT reconstruction advancements. This unique method, termed speckle contrast DCT (scDCT), facilitates 3-D flow contrast imaging of complex turbid media (see e.g. FIG. 5)[40]. As this technique promotes incorporation of both heterogeneous optical properties and arbitrary tissue boundaries, scDCT utilizes highly representative sample characteristics in the recovery of accurate flow data. This scDCT technique is applied on a reflectance-based measurement which more adequately represents the situation encountered in larger subjects such as humans where transmission is not practical in most cases (due to the limited penetration depth of light), enhancing translatability. A smear correction algorithm is also provided herein that assists to resolve the influences on data uniquely incurred when using frame-transfer CCDs with the point-source illumination and reflectance setup.[6]

Testing the scDCT for 3-D imaging of deep flow distribution in tissue phantoms with an anomaly is depicted in FIG. 5 and FIGS. 28 to 31. A cube-shaped solid anomaly (flow=0) with ~7 mm side length was submerged ~2 mm beneath the surface of an Intralipid liquid solution (flow≠0). A square metal holder positioned four source fibers in contact with the liquid surface (FIG. 5a). An optical switch distributed laser light (830 nm) into the four source fibers (S1 to S4), sequentially. The configuration of anomaly placement, sources, CCD detection area, and field of view (FOV) is shown in FIG. 31b. Reconstructed 3-D and 2-D cross-sectional views of the anomaly flow contrast are shown in FIG. 31c and FIG. 31d, respectively, which meet our expectations.

Noncontact scDCT (nc_scDCT)

As with APDs, the systems utilizing CCD as a 2-D detector array can be utilized in a manner that avoids contact with the tissue being imaged. Such a system is referred to herein as noncontact speckle contrast DCT (nc_scDCT). The scDCT system itself, exemplified in FIG. 5, is a semi-noncontact system (i.e., sources remain in contact with the tissue). A fully noncontact scDCT system (i.e., nc_scDCT) can be achieved by using multiple source fibers that are positioned around the CCD (such as affixed to the exterior of the CCD lens as seen in FIG. 6a) or one source coupled to a Galvo mirror (see e.g. FIG. 6b). Both remove the need of contact between the sources and the tissue. FIG. 6c shows an example of a typical source-detector distribution diagram for this system.

Sources and Detectors Alignment on 3-D Tissue Modeling

To render an image using the ncDCT system, first the imaging probe is set at the desired working distance (as used in the EXAMPLES herein, such a distance is ~10 cm) from the tissue area to be imaged. The autocorrelation function at each sampling location is then taken while also automatically scanning the probe linearly (see, e.g. Lin et al., App. Phys. Lett. 104: 121103 (2014)) or rotationally (see e.g., Huang et al. App. Optics 54: 8808-8816 (2015)). The width of the region of interest with the systems exemplified herein is typically around 4 cm wide. Next, boundaries of the targeted area are obtained by a commercial 3-D camera. A model of the tissue is then created with an arbitrary surface using a 3-D CAD software program, followed by the alignment of sources and detectors to the surface of the 3-D model. The boundary flow index is then fitted from the obtained autocorrelation function for each S-D pair at each sampling location. Collected data are then entered into modified FEM-based software (e.g., NIRFAST) for 3-D flow image reconstruction.

In instances of performing nc_scDCT, following setup of the system and ensuring both source and detectors are focused at the target surface, the surface intensity image alternatively for each source location should be obtained. Then, the boundaries of the target may be taken by a commercial 3-D camera. Tissue is then modeled with an arbitrary surface in 3-D CAD software and the sources and detectors are aligned on the surface of the 3-D model. Then, the intensity image is corrected for smeared intensity and the speckle contrast K and correct related noises are calculated as discussed above. The boundary flow index for each detector from K is then fitted and flow index information of the S-D set is combined with the forward and inverse solutions from NIRFAST for 3-D flow image reconstruction.

Further References

The following are listed as background and to provide further details to the features described herein. All are hereby incorporated by reference in their entirety: 1. Leachtenauer et al. Conference proceedings: Annual International Conference of the IEEE Engineering in Medicine and Biology Society IEEE Engineering in Medicine and Biology Society Annual Conference. 2006; 1:6380-3; 2. Liu et al. *J Rehabil Res Dev.* 2006; 43:209-18; 3. Kanno et al. *Spinal Cord.* 2009; 47:225-9; 4. Colwell et al. *Plastic and reconstructive surgery.* 2011; 128:1170-8; 5. Spear S L, Carter M E and Schwarz K. Prophylactic mastectomy: indications, options, and reconstructive alternatives. *Plastic and reconstructive surgery.* 2005; 115:891-909; 6. Spear et al. *Plastic and reconstructive surgery.* 2014; 133:605e-614e; 7. Surgeons. ASoP. 2014 report of the 2013 statistics: National Clearinghouse of Plastic Surgery Statistics. Available at: www.plasticsurgery.org/Documents/news-resources/statistics/2013-statistics/plastic-surgery-statistics-full-report-2013.pdf . . . 2014; 8. Kanuri et al. *Plastic and reconstructive surgery.* 2014; 133:448e-54e; 9. Haddad R I. Multidisciplinary management of head and neck cancer. New York: Demos Medical; 2011; 10. Holzle et al. Journal of cranio-maxillo-facial surgery: official publication of the European Association for Cranio-Maxillo-Facial Surgery. 2006; 34:25-33; 11. Lorenzetti et al. *J Reconstr Microsurg.* 2001; 17:163-167; 12. Prionas et al. *Radiology.* 2010; 256: 714-23; 13. Avril et al. Journal of clinical oncology: official journal of the American Society of Clinical Oncology. 1996; 14:1848-57; 14. Durduran et al. *Opt Lett.* 2005; 30:2915-7; 15. Zhou et al. *J Biomed Opt.* 2007; 12:051903; 16. Yu et al. *J Biomed Opt.* 2012; 17:010901; 17. Choe et al. *PloS one.* 2014; 9:e99683; 18. Choe et al. *J Biomed Opt.* 2009; 14:024020; 19. Tromberg et al. *Medical physics.* 2008; 35:2443-51; 20. Zhu et al. *Radiology.* 2010; 256:367-78. 10; 21. Fang et al. *Radiology.* 2011; 258:89-97; 22. Flexman et al. *J Biomed Opt.* 2011; 16:076014; 23. Lin et al. *Appl Phys Lett.* 2014; 104; 24. Boas et al. *J Opt Soc Am A Opt Image Sci Vis.* 1997; 14:192-215; 25. Pryor et al. Otolaryngology—head and neck surgery: official journal of American Academy of Otolaryngology—Head and Neck Surgery. 2006; 135:714-8; 26. Luu et al. *Curr Opin Otolaryngo.* 2009; 17:267-269; 27. Ichinose et al. *J Reconstr Microsurg.* 2004; 20:207-213; 28. Hanasono et al. *J Reconstr Microsurg.* 2009; 25:417-424; 29. Lorenzetti et al. *Microsurg.* 1999; 19:196-199; 30. Smits et al. *J Appl Physiol.* 1986; 61:666-72; 31. Kienle et al. *Phys Med Biol.* 2001; 46:1231-44; 32. Komorowska-Timek et al. *Plastic and reconstructive surgery.* 2010; 125:1065-73; 33. Lin et al. *Applied physics letters.* 2014; 104:121103; 34. He et al. Commun Numer Meth Engng. 2009; 25; 35. He et al. *J Biomed Opt.* 2015; 20:86003; 36. Choe R. Diffuse optical tomography and spectroscopy of breast cancer and fetal brain. 2005; 37. Wilson et al. *Intl Cancer.* 1991; 47:344-7; 38. Beaney et al. *Lancet.* 1984; 1:131-4; 39. Huang et al. *Journal of biomedical optics.* 2015; 20:75008; 40. Huang et al. *Medical Physics Letters.* 2015; 42:4000; 41. Fercher et al. *Opt Commun.* 1981; 37:326-330; 42. Bi et al. *Opt Lett.* 2013; 38:1401-3; 43. Valdes et al. *Biomed Opt Express.* 2014; 5:2769-84.

EXAMPLES

Ex. 1: Noncontact Diffuse Optical Assessment of Blood Flow Changes in Head and Neck Free Tissue Transfer Flaps The custom-made ncDCS system for the noncontact measurement of tissue blood flow is shown in FIG. 1. A noncontact optical probe is held by a platform connected to a linear motorized stage. A multiple axis stand holder provides free movements to adjust the location and incident angle of the probe. A DCS flowmetry is controlled by a laptop for continuous monitoring of tissue blood flow as soon as the noncontact probe is aligned over the target tissue. The four-channel DCS device consists of a long-coherence-length (>5 m) NIR laser diode (785 nm, 100 mW, Crysta-Laser Inc, California), four single-photon-counting avalanche photodiodes (APDs, Perkin Elmer, Canada), and a four-channel correlator (correlator.com, New Jersey). The ncDCS system is integrated compactly and portably to ensure convenient operation in both operating and patient rooms.

FIG. 2(a) shows the details of the noncontact probe structure. The source fiber (WF200/220/245, CeramOptec, Massachusetts) connected to the long-coherence laser is projected onto the tissue surface through achromatic lenses [FIG. 2(b)]. The detector fiber bundle [FIG. 2(a)], including California), are equally arranged in a 7-mm line to cover a 20-mm range through the magnification of lenses. The source and detector fibers are aligned to focus on the tissue surface.

Photons emitted from the laser are injected through the source path into the tissue sample. Only a few photons traveling through the sample can be eventually collected through the detection path by the linear detector array of four APDs. The four source-detector (S-D) distances are set as 10.0, 15.7, 22.8, and 30.0 mm [FIG. 10]. According to the diffuse theory, the photon penetration depth is about half of the S-D distance.[28-30] Thus, for the probe structure described above, corresponding light penetration depths range approximately from 5 to 15 mm. The correlator takes the four APD outputs and calculates the light intensity autocorrelation functions, which are used to extract tissue blood flow information. The sampling rate of DCS measurement is 1 Hz.

Details about DCS theory and data processing have been described in literature.[21,22,26,27,31,32] Briefly, light intensity fluctuation with time detected by APD is associated with the motion of red blood cells in tissue microvasculature and can be quantified by the decay of the intensity autocorrelation function calculated by the autocorrelator. From the normalized intensity autocorrelation function, the electric field temporal autocorrelation function is determined, which satisfies the correlation diffusion equation in highly scattering media.[16] By fitting the electric field autocorrelation curve to an analytical solution of correlation diffusion equation with a semi-infinite medium geometry, a blood flow index (BFI) is extracted.[30] The relative change of blood flow (rBF) can be calculated by normalizing the time-course BFI data to the baseline value taken before physiological changes to be studied.

Most previous DCS measurements were based on a continuous manner, either with contact[19,22,32-36] or noncontact[26,27] probes, to quantify blood flow changes without variation of the DCS device in long period intervals. In this study, however, we intended to measure the same flap at different days with the noncontact probe. In order to investigate ncDCS stability with this noncontinuous measurement protocol, the ncDCS probe was first tested on a homogenous liquid phantom placed in an aquarium. The tissue-like liquid phantom comprised Intralipid (Fresenius Kabi, Sweden), distilled water, and India ink (Black India, Massachusetts) and has been used extensively for DCS calibrations.[37] Intralipid particles provide control of scattering ($\mu_s'$) and Brownian motion (flow) while India ink controls absorption ($\mu_a$). We set $\mu_a$=0.05 cm$^{-1}$ and $\mu_s'$=7.0 cm$^{-1}$. We measured the same liquid phantom once a day over seven days. We also tested the stability of ncDCS measurements on the forearm of a healthy subject in a similar manner. For each measurement in a day, flow data were taken for 2 min from the same location of the phantom/forearm with the same ncDCS probe. The flow values measured over seven days were normalized to the first day, representing flow variations over a week.

Blood Flow Measurement Protocol of Free Tissue Transfer

Seven patients with head and neck cancer undergoing free tissue transfer participated in this study as part of their oncologic extirpation and reconstruction procedure at the University of Kentucky hospital. Written consents were obtained from all patients as well as the healthy subject (as a control for the forearm measurement) in accordance with approval by the University of Kentucky's Institutional Review Board. In total, eight free flaps were elevated on the seven patients. Patient 7 underwent a flap that failed (case 8) and another subsequent successful flap (case 7). Details for patient demographic and reconstruction information are listed in Table 1. All free flaps were raised in a usual manner.[38] After complete elevation of the flap with only the main arterial pedicle and venae comitantes remaining attached to its native blood supply, an optical measurement using the ncDCS probe was performed [FIG. 7(a)]. After this measurement, the arterial pedicle and venae comitantes were ligated. The appropriate free flap was inset to reconstruct the corresponding head and neck defects and the venous and arterial pedicles were anastomosed to recipient vessels from the external carotid system and internal jugular venous system. Each arterial pedicle was anastomosed in an end-to-end configuration using 9-0 nylon sutures. Venous pedicles were attached in either an end-to-end or an end-to-side configuration using venous couplers.

TABLE 1

Patient demographic and reconstruction information

| Patient Number | Age | Gender | Type of flap | Successful flap? |
|---|---|---|---|---|
| P1 (case 1) | 63 | M | RFFF | Y |
| P2 (case 2) | 65 | M | ALT | Y |
| P3 (case 3) | 54 | M | ALT | Y |
| P4 (case 4) | 46 | F | RFFF | Y |
| P5 (case 5) | 64 | F | RFFF | Y |
| P6 (case 6) | 74 | M | RFFF | Y |
| P7 (case 7) | 74 | F | RFFF | Y |
| P7 (case 8) | 74 | F | FFF | N |

Note:
RFFF, radial forearm free flap.
ALT, anterior lateral thigh free flap;
FFF, fibula free flap.

Figure 7:
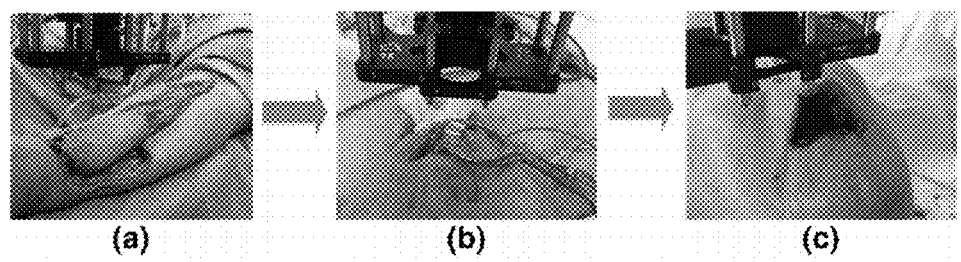
FIG. 7 shows the protocol for perioperative blood flow monitoring during free tissue transfer measured by ncDCS: (a) intraoperative measurement on the elevated flap; (b) intraoperative measurement on the flap after anastomosis through mouth cavity; (c) postoperative measurement on the transferred flap.

Approximately 30 min after anastomosis of these vessels, a second optical measurement was performed at the location of the transferred tissue within the head and neck (oral cavity, orbit, or neopharynx) [FIG. 7(b)]. In addition, multiple optical measurements probing at the same location of the transferred free tissue were performed on postoperative days 2, 4, and 7 in a similar fashion to the intraoperative measurement after anastomosis [FIG. 7(c)]. FIG. 7 illustrates the protocol of blood flow measurements performed specifically for the reconstruction of an oral cavity defect (P7). In each setting, optical measurements were taken with the ncDCS optical probe directed toward the cutaneous surface of the reconstructed tissue and were kept at the same working distance and spot throughout the protocol. During intraoperative measurements, we took photos using a camera to record the locations of the ncDCS source. Note that the focused light source point (785 nm) on the tissue surface can be recorded by the camera. For postoperative measurements, we tried our best to align our probe to cover the same region of the flap. DCS data collection time for each measurement was approximately 2 min at a sampling rate of 1 Hz.

Data Analysis

The BFI data (2 min) obtained from the four S-D distances of ncDCS during the operation at the intraoperative flap elevation step and on the three postoperative days (i.e., days 2, 4, and 7) were normalized to the averaged BFI baseline values (assigning "1") taken at ~30 min after flap anastomosis, yielding rBF. The 2-min rBF data were then averaged to generate mean rBF values at four S-D distances, respectively. Finally, the mean standard deviation of the rBF values at four S-D distances were calculated to represent the rBF value and corresponding flow heterogeneity across the measured bulk flap tissue. Statistical tests for averaged rBF differences at different time points were performed using one-way repeated measures ANOVA with main effects of the time period. p value<0.05 was considered significant for statistical results.

Results

Figure 8:
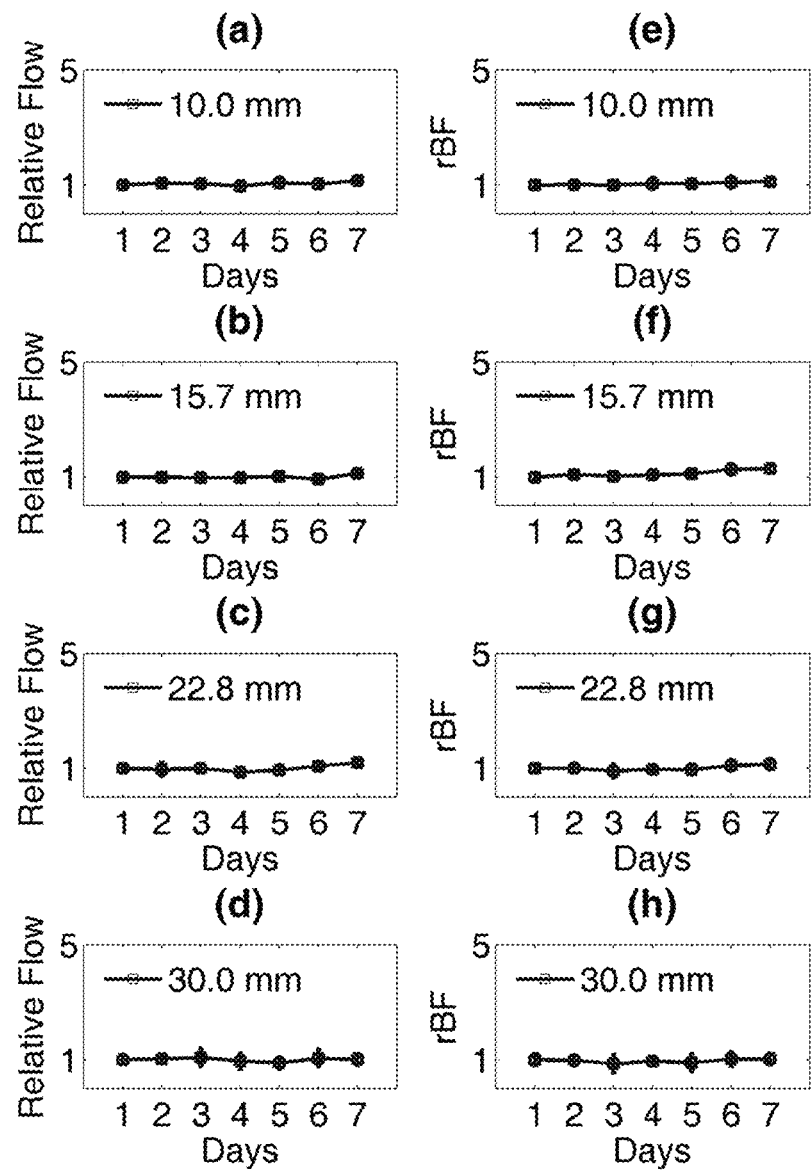
FIG. 8 shows the flow variations at the four different S-D separations (10.0, 15.7, 22.8, 30.0 mm) measured by ncDCS on the (a)-(d) liquid phantom and (e)-(h) healthy forearm over seven days. The error bars represent the standard deviations over the 2-min measurements.

FIG. 8 shows relatively smaller changes in flow over seven days measured from the liquid phantom [FIGS. 8(a)-8(d)] and healthy forearm [FIGS. 8(e)-8(h)]. Flow variations over days measured at all S-D pairs were fairly constant, indicating the stability of ncDCS for non-continuous measurements. By averaging rBF (or relative flow in the phantom) values over the four S-D separations, we found that the largest flow variations were only 1.09±0.23 from the phantom and 1.13±0.24 from the forearm (mean±standard deviation).

Figure 9:
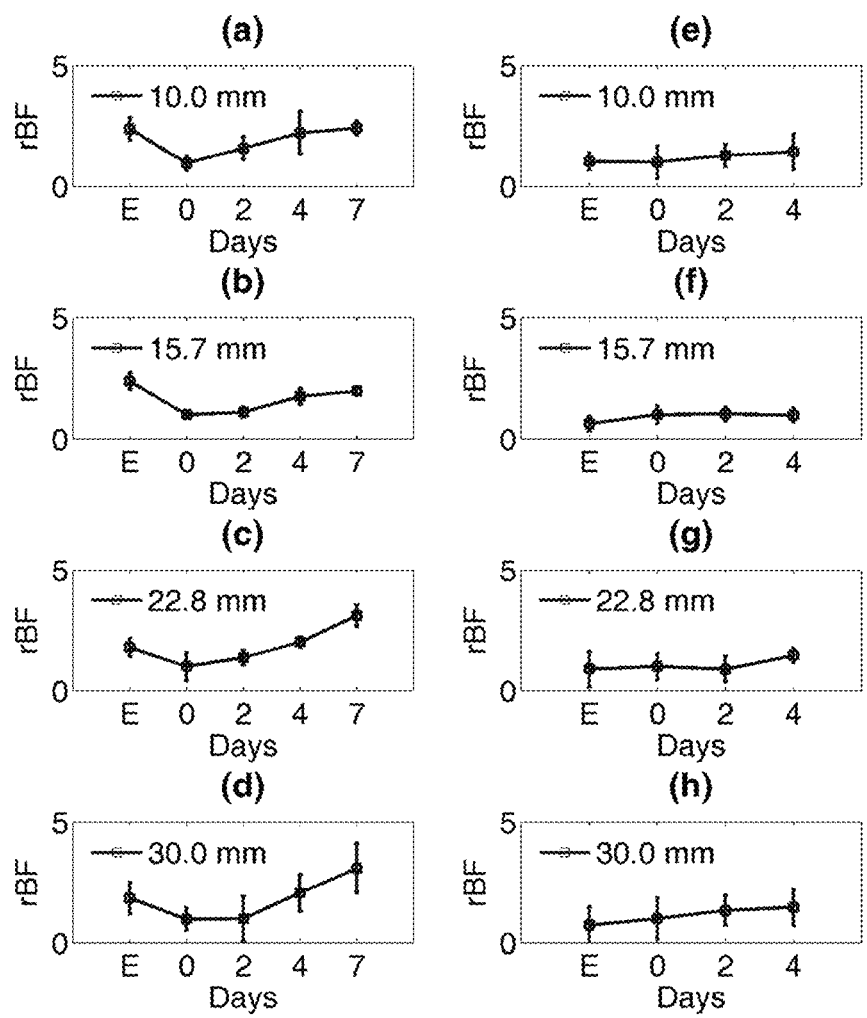
FIG. 9 shows the blood flow variations (rBF) measured by ncDCS at (a)-(d) four S-D separations in one successful case (case 1) and (e)-(h) the unsuccessful case during the operation and at postoperative days 2, 4, 7 (data are not available at postoperative day 7 for the unsuccessful case). "E" represents the time point when the flap is raised. Day "0" represents ~30 min after flap anastomosis, which is used as the baseline for normalization. Error bars represent standard deviations over the 2-min time course data.

By contrast, remarkably larger rBF variations were observed from all patients over the seven days. FIG. 9 shows illustrative results measured from one typical successful case (case 1) and the failure case (case 8). FIG. 10 shows the average results over the seven successful cases; significant differences were found among the flow responses obtained from the four separations (one-way ANOVA test, p<0.001). Although heterogeneous flow responses at different S-D pairs existed due to the tissue heterogeneity at different depths and regions of tissues, the trends of blood flow alterations measured at different S-D separations were fairly consistent in each case (FIG. 9) and over subjects (FIG. 10).

We then calculated bulk blood flow in the flap by averaging DCS data obtained from the four S-D detectors, which represented the overall flap hemodynamics better than that from a local tissue volume detected by a single S-D pair. FIG. 11 shows these results from all eight free flap cases including seven successes (cases 1 to 7) and one failure (case 8). Larger variations in rBF were observed in all patients at all measurement time points. In the group data of successful cases, an initial decrease of the blood flow was observed intraoperatively (from the elevation of free flap to the end of vessel anastomosis), followed by a graduate flow recovery during the following postoperative days. By contrast, rBF changes/recoveries in the unsuccessful flap during and post vessel anastomosis were smaller than all successful flaps.

Figure 12:
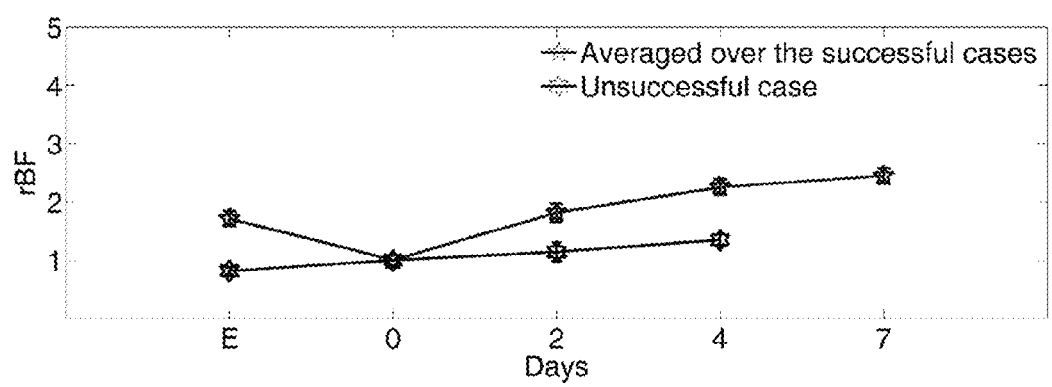
FIG. 12 shows the comparison of rBF changes measured by ncDCS between the successful and unsuccessful flaps. Averaged rBF values over the seven successful cases during operation and on postoperative days 2, 4, 7 are presented as mean standard errors (error bars represent the variations over seven cases). rBF from the unsuccessful flap (case 8) was measured at the time of flap elevation and on postoperative days 2 and 4.

For better comparison, the averaged rBF values over the seven successful flaps as compared to the unsuccessful flap (case 8) are shown in FIG. 12. For the group data of seven successful flaps, average intraoperative rBF at the time of flap elevation was 1.71±0.12 (mean±standard error). Average postoperative rBF on postoperative days 2, 4, and 7 were 1.89±0.15, 2.26±0.13, and 2.43±0.13 (mean±standard error), respectively. The rBF variations over all measurement time points were significant (one-way ANOVA test, p<0.001). By contrast, rBF values observed from the unsuccessful flaps were 0.82, 1.14, and 1.34, respectively, at the time of flap elevation and on postoperative days 2 and 4, which were apparently lower than the successful cases.

Discussion and Conclusions

This study focused on evaluating the microvascular circulation of free flaps both intraoperatively and postoperatively using a novel ncDCS technique. Due to previous blood flow measurements using DCS or ncDCS performed mostly in a continuous manner,[19,22,26,27,32-36] a challenge of this study was the quantitative stability of the non-continuous measurements over several days. To facilitate a quantitative comparison during perioperative monitoring period (7 days) in the protocol, rBF (or relative flow) in the liquid phantom with a stable flow and in the healthy forearm were monitored by ncDCS once a day over one week.

The results demonstrated fairly stable flow values during the non-continuous measurements (see FIG. 8). The mean flow variations over the four S-D pairs during the measurement period were less than 9% (phantom) and 13% (forearm), respectively. By contrast, the results shown in FIGS. 9-12 indicated significantly larger flow variations in the reconstructed flaps over the perioperative measurement period. The perioperative variations of blood flow in the elevated flaps meet the expectation of physiological responses to any surgical insult. There is almost always an initial drop of blood flow after vessel anastomosis as fresh flaps are ischemic.[39] The postoperative continuous increase in rBF results from the gradual recovery of tissue injuries associated with the decrease of vascular resistance in those elevated flaps.[7] Depending of the degree of ischemia and the amount of time before recovery of blood flow, the flap will either die or recover.[39] Interestingly, blood flow in the unsuccessful case did not show either the initial drop of blood flow after vessel anastomosis or the postoperative recovery. Although more cases need to be performed, the observed perioperative differences in blood flow between the unsuccessful and successful flaps (see FIGS. 11 and 12) demonstrate the potential of ncDCS measurements to predict early free flap failures.

Our results are comparable to data available in literature obtained using other technologies such as laser Doppler[8] and ultrasound Doppler.[4-6] For example, intraoperative decreases in blood flow after flap anastomosis[6,8] and postoperative increases/recoveries in blood flow/velocity[4,5,8] were observed, which are similar to our results (see FIGS. 10 and 12). A previous case study also reported lower blood flow after anastomosis in an unsuccessful flap.[6] In addition, preliminary results from a pilot study showed the potential of blood flow measurements using laser Doppler to predict flap failure before other clinical signs.[8] However, in contrast to ultrasound or laser Doppler technology that focuses on evaluating blood flow/velocity in large vessels or superficial tissues, the nature of ncDCS measurement is to quantify blood flow changes in deep tissue microvasculature.[20,26] Since appropriate blood flow in tissue microvasculature is the key for the survival of flaps,[49,41] ncDCS may become a useful tool with more sensitive measurements than the ultrasound/laser Doppler technology in monitoring tissue flap vascularity. The ncDCS technology is feasible for perioperative measurements of tissue blood flow in all flaps included within this study, despite the anatomical challenges that these flaps present intraoperatively and postoperatively. These findings are encouraging as this technology may offer surgeons the ability to assess tissue blood flow in real time during the surgery, immediately after vessel anastomosis, as well as in the early postoperative period when flap compromise is the highest. A prominent advantage of the ncDCS system is the use of its noncontact probe, which allows measurements to be taken under nonsterile conditions. It also avoids potential distortion in blood flow signals resulting from contact-probe compression on the target tissue. Furthermore, the noncontact probe is able to assess blood flow over the reconstructed tissue without interfering with the sterility of the surgical fields and the surgical setup. Several challenges have arisen in the early implementation and use of this device. The complex anatomical configurations of head and neck reconstructions and patients' limitations have been successfully addressed. For example, flaps used to reconstruct the oral cavity are difficult to assess fully. Adaptations by measuring through the intact skin and submental tissues up to the reconstruction tissue have shown promise (cases 5 and 7). Practically, tissue blood flow can be assessed approximately up to 15 mm below the skin surface with this current model of the DCS system (i.e., half of the maximum S-D distance of 30 mm).

However, tissue congestion and edema may affect light penetration and blood flow measurement, which needs further evaluations using tissue-simulated phantoms.[42] In this study, tissue blood flow was measured by ncDCS intraoperatively and postoperatively. During intraoperative measurements, the patient was anesthetized and thus there was no motion artifact in blood flow measurements. During postoperative measurements, the subject was asked to keep still during the short period of measurements (~2 min). We did not find obvious motion artifacts in postoperative measurements either. Moreover, we averaged the 2-min data to reduce the variation during measurements. In addition, the potential influence of probing tissue curvature on ncDCS flow measurements has been previously investigated by our group.[27] The results revealed that curvature resulted in slight underestimation in BFI, but not in rBF. Blood flow quantification in this study was performed by ncDCS in a longitudinal time frame with limited point measurements (i.e., four S-D pairs). We indeed observed the heterogeneity of blood flow responses at different depths and regions due to the tissue heterogeneity (see FIGS. 9 and 10). Ideally, 3-D imaging of flap would provide complete information for predicting the flap viability. However, our ncDCS system has limited numbers of sources and detectors and thus cannot generate a 3-D flow image. Recently, ncDCS has been extended in our laboratory to the noncontact diffuse correlation tomography (ncDCT)[42] and speckle contrast diffuse correlation tomography (scDCT).[43] Both ncDCT and scDCT have the potential to assess the spatial flow distributions in deep flaps with 3-D tomographic information.

In conclusion, we were able to use the ncDCS in multiple and complex head and neck reconstructions with different free tissue transfers. ncDCS is a promising tool that may provide objective information regarding flap viability in real-time intraoperatively and in the early postoperative periods, thus allowing surgeons early identification of those compromised and ischemic flaps with the hope of salvaging them.

References: 1. Haddad, Multidisciplinary Management of Head and Neck Cancer, Demos Medical, New York (2011); 2. Pryor et al. Otolaryngol. Head Neck Surg. 135(5), 714-718 (2006); 3. Luu et al. Curr. Opin. Otolaryngo. 17(4), 267-269 (2009); 4. Ichinose et al., J. Reconstr. Microsurg. 20(3), 207-213 (2004); 5. Hanasono et al., J. Reconstr. Microsurg. 25(7), 417-424 (2009); 6. Lorenzetti et al., J. Reconstr. Microsurg. 17(3), 163-167 (2001); 7. Lorenzetti et al., Microsurgery 19(4), 196-199 (1999); 8. Holzle et al., J. Cranio-Maxillo-Facial Surg. 34(1), 25-33 (2006); 9. Smits et al., J. Appl. Physiol. 61(2), 666-672 (1986); 10. Kienle, Phys. Med. Biol. 46(4), 1231-1244 (2001); 11. Fantini et al., Phys. Med. Biol. 44(6), 1543-1563 (1999); 12. Franceschini et al., J. Biomed. Opt. 11(5), 054007 (2006); 13. Sunar et al., J. Biomed. Opt. 11(6), 064021 (2006); 14. Duncan et al., Phys. Med. Biol. 40(2), 295-304 (1995); 15. Tian et al., J. Biomed. Opt. 14(5), 054016 (2009); 16. Boas et al., Phys. Rev. Lett. 75(9), 1855-1858 (1995); 17. Boas et al., J. Opt. Soc. Am. A 14(1), 192-215 (1997); 18. Pine et al., Phys. Rev. Lett. 60(12), 1134-1137 (1988); 19. Yu et al., J. Biomed. Opt. 16(2), 027004 (2011); 20. Yu, Curr. Med. Imaging Rev. 8(3), 194-210 (2012); 21. Dong et al., Biomed. Opt. Express 3(2), 259-272 (2012); 22. Gurley et al., J. Biomed. Opt. 17(7), 075010 (2012); 23. Gioux et al., J. Biomed. Opt. 16(8), 086015 (2011); 24. Gravvanis et al., World J. Surg. 31(1), 11-18 (2007); 25. Nguyen et al., J. Surg. Res. 177(2), e83-e88 (2012); 26. Lin et al., J. Biomed. Opt. 17(1), 010502 (2012); 27. Li et al., Sci. Rep. 3,1358 (2013); 28. Van Beekvelt et al., J. Appl. Physiol. 90(2), 511-519 (2001); 29. Yu et al., J. Biomed. Opt. 10(2), 024027 (2005); 30. Shang et al., Biomed. Opt. Express 1(2), 500-511 (2010); 31. Yu et al., Opt. Express 15(3), 1064-1075 (2007); 32. Shang et al., Opt. Lett. 34(22), 3556-3558 (2009); 33. Shang et al., J. Biomed. Opt. 18(10), 105002 (2013). 34. Cheng et al., Appl. Opt. 52(30), 7324-7330 (2013); 35. Cheng et al., J. Biomed. Opt. 19(1), 017001 (2014); 36. Shang et al., Phys. Med. Biol. 56(10), 3015-3032 (2011); 37. et al., Biomed. Opt. Express 2(7), 1969-1985 (2011); 38. Urken, Atlas of Regional and Free Flaps for Head and Neck Reconstruction: Flap Harvest and Insetting, 2nd ed., LWW, Riverwoods, Ill. (2011); 39. Myers, Plast. Reconstr. Surg. 78(6), 813-814 (1986); 40. Jokuszies et al., J. Reconstr. Microsurg. 22(7), 513-518 (2006); 41. Gurlek et al., J. Reconstr. Microsurg. 13(5), 345-349 (1997); 42. Lin et al., Appl. Phys. Lett. 104(12), 121103 (2014); 43. Huang et al., Med. Phys. 42(7), 4000-4006 (2015).

Ex2: Three-Dimensional Flow Contrast Imaging of Deep Tissue Using Noncontact Diffuse Correlation Tomography Blood flow distribution in tissues can provide vital information to healthcare professionals including clinicians and research investigators. Alterations in blood flow may result, for example, in regions of tissue presenting with ischemia and hypoxia. These abnormalities are associated with and help characterize many diseases including pressure ulcers, stroke, and cancer. Furthermore, blood flow contrast imaging can assist in applications such as cancer diagnosis and therapy monitoring.[1] Near-infrared diffuse correlation spectroscopy (DCS) has emerged as a highly advantageous blood flow monitoring modality through inherent noninvasiveness, safe application, portability, deep tissue probing (up to several cm), and relative affordability.[1-4] Most DCS systems employ contact-based interaction with the sample. However, in tissues, contact measurements can promote hemodynamic variations induced by compression or disturb sensitive areas. We have recently developed a noncontact DCS system that uses a lens-focusing technique to circumvent these influences.[2,4]

Despite advances in DCS applicability there have been limited tomographical imaging realizations. A few studies involving three-dimensional (3-D) diffuse correlation tomography (DCT) have been performed with tissue-like phantoms, computer simulations, and in vivo rat brain.[5-7] An early contact-based approach was applied to phantoms,[5] but is disadvantaged in vivo as described previously. Very few noncontact-based DCT examinations have been conducted as well. In these, lenses were positioned between a sample and optical fiber grid connected to light and detection elements.[6,7]

These arrangements, however, were only tested on small animals with limited source-detector (S-D) separations ranging from 2 to 10 mm. Flexibility is minimal and expense increases with the scaling of the region of interest (ROI).

Another limitation of these studies is reliance on analytical solutions assuming a simple semi-infinite geometry and strict heterogeneities (e.g., spherical) of tissue which precludes the transition to complex boundaries and imperfect heterogeneities. Complications would also become apparent in accommodating complex boundaries with numerous S-D fibers. Furthermore, in testing these types of systems, the imitation of flow contrast changes often relies on solid phantoms (no flow) embedded in liquid phantoms (Intralipid; Brownian particle motion) or the converse case. This method lacks elegance due to the restrictively static nature of the components once prepared, specifically the solid phantom material. The current study seeks to remedy many of these concerns. First, we extended our noncontact DCS system[2,4] to noncontact DCT (ncDCT) using a motorized stage for automated and customizable ROI scanning capabilities. Next, a finite-element-method (FEM) based facilitation of DCT image reconstruction was accomplished through integration into an open software package for diffuse optical spectroscopy/tomography (DOS/DOT) termed NIRFAST.[8] Finally, validation efforts included computer simulations and a phantom testing design allowing flow variations.

Extending DCS into DCT attaches the burden of collecting many boundary measurements. As such, our noncontact probe was upgraded to have two identical laser source paths and one detector path (FIG. 4(a)) doubling our previous number of available S-D pairs. In each source path, output from a multimode fiber (WF200/220/245, CeramOptec, MA, USA) connected to a laser was projected onto the tissue phantom surface through lenses.[2,4] The detector fiber head (FIG. 4(b)) in the detector path contained 15 single-mode fibers (SM800-5.6-125, Fibercore, CA, USA) equally arranged in a 7 mm line covering a 20 mm range through lenses at 100 mm working distance. The resulting S-D separations were in the span of 10 to 30 mm, thus allowing up to ~15 mm penetration depth.[1] Instrument operation involves two 825 nm long coherence lasers (coherence length>5 m, CrystaLaser, NV, USA) emitting photons to tissue through individual source paths alternatively. The photons traveling through the sample are collected by a detector array of 15 avalanche photodiodes (APD, Perkin Elmer, Canada) through the detector path. A multiple channel autocorrelator (Correlator.com, NJ, USA) takes the APD outputs and simultaneously calculates the correlation functions for the 15 S-D pairs per source.[3] Another significant improvement was the integration of a motorized stage for automatic and precise ROI scanning (FIG. 4(c)) through probe translation. Either rotational or linear motion staging is available to maximally fit the subject geometry (e.g., breast shape or slab shape). This design feature enables large ROI coverage and flexible S-D arrangements without greatly increasing hardware requirements and costs (e.g., fibers, APDs, and correlators). In this study, the ncDCT modality was motivated by the linear stage (T-LSM200A, Zaber, Canada).

Application of DCS theory, as well as correction for smearing is performed using the algorithms described herein. To test our theoretical DCT technique through computer simulations, we first evaluated forward solution accuracy in a homogeneous situation (i.e., no anomaly). A slab mesh [dimension (mm): 90 (H)×90 (W)×35 (D)] was generated with total node number 73 949 simulating liquid phantom solution in a slab shaped container (e.g., aquarium). Optical properties were set throughout at $\mu_s'$=8.00 cm$^{-1}$ and $\mu_a$=0.045 cm$^{-1}$ close to breast tissue values.[9] The slab flow indices ($\alpha D_B$) were set close to Intralipid phantom values[5,10] at 1×10$^{-8}$ cm$^2$/s and correspond to the background tissue. As shown in FIG. 4(c), the noncontact probe was scanned linearly (mimicked in simulation) across the ROI in 15 steps with an increment of 4 mm/step generating a scanning area of 40 mm×56 mm and 450 (15 steps×15 APDs×2 sources) effective S-D pairs. The forward solution (i.e., $G_1(\tau)$) was calculated by the modified NIRFAST with s from 0 to 8×10$^{-6}$ s. Minimal simulation aberrations over the measured ROI (1% mean discrepancy and 1.45% standard deviation) were observed between $\alpha DB$ extracted using the established semi-infinite analytical solution[2] of Eq. (2) and the assigned $\alpha DB$. With the forward solution verified, the next simulation embodied recovery of an anomalous presence and subsequent contrasts. A cylindrical tube-shaped anomaly [dimension (mm): 13 (Dia.)×80 (L)] was inserted beneath the middle of the ROI with a depth of 12.5 mm from the tube center to the ROI surface. The anomaly optical properties (i.e., $\mu_a$ and $\mu_s'$) were matched to the background tissue. The attributed anomaly $\alpha D_B$ was varied with contrast ranging from 0, 4, 8, 12, 16, and 20 times of the background (1×10$^{-8}$ cm$^2$/s). Reconstruction was conducted on a second mesh with coarse finite element division (node number: 11 025) and the same optical properties. The delay time $\tau$=3.2×10$^{-6}$ s was used to calculate $\mu_a^d(\tau)$. Due to limited ROI dimensions along the tube, only partial anomaly reconstruction was possible (FIG. 13(a)). For percentage flow change comparison, the reconstructed anomaly peak flow value was normalized to the averaged step differences of $\alpha D_B$. Both the shape (FIG. 13(a)) and relative anomaly flow contrast changes (FIG. 13(b)) were well reconstructed (regression slope=1.00, R$^2$=1.00, and p<10$^{-5}$). We also used a half maximum threshold to segment the anomaly and then calculated its mean flow value. An excellent linear relationship was also observed between the reconstructed and assigned percentage flow changes (data are not shown; regression slope=1.00, R$^2$=1.00, and p<10$^{-5}$).

To evaluate the errors in depth reconstruction (localization) of the anomaly and their dependence on the size of anomaly, we performed supplementary simulations using the existing tube and a smaller tube [6 (Dia.) mm 80 (L) mm]. The anomaly central depth was varied up to 16.5 mm beneath the surface.

The reconstructed central depths of the tube anomalies and the relative changes of flow index contrasts were accurate when the assigned anomaly was localized in the sensitive region of light diffusion (i.e., anomaly central depth 12.5 mm; data are not shown). These simulation results demonstrated the robustness of the proposed FEM-based ncDCT technique.

We next validated the developed system in practical object measurements by phantom experimentation. A background of liquid phantom was placed in an aquarium (FIG. 4(c)) and a pump-connected cylindrical tube anomaly was filled with liquid and small pieces of solid phantom (FIG. 4(d)). The tissue-like liquid phantom comprised Intralipid, distilled water, and India ink and has been used extensively for DCS calibrations.[4] Intralipid particles (Fresenius Kabi, Sweden) provide control of scattering ($\mu_s'$) and Brownian motion ($D_B$; $\alpha \approx 1$) while India ink controls absorption ($\mu_a$).

We set $\mu_s'$ and $\mu_a$, respectively, at 8.10 cm$^{-1}$ and 0.044 cm$^{-1}$ while quantifying them with a FD tissue-oximeter (Imagent, ISS, IL, USA).[11] To create flow index contrasts against the background, a clear plastic tube [dimension (mm): 13.5 (Dia.) 80 (L)] with a very thin wall (0.35 mm) was placed at 12.5 mm (tube center to ROI surface) into the background liquid phantom (FIG. 4). The tube was mostly filled with small pieces of solid phantom ($\mu_s'$=10.00 cm$^{-1}$ and $\mu_a$=0.10 cm$^{-1}$) to randomize pumped particle motions as Brownian motion and generate a diffusive circumstance for photons. Solid phantoms comprised titanium dioxide, silicon, and carbon black. A peristaltic pump (HV-77201-60, Cole Parmer, Ill., USA) connected in series with a hydraulic capacitor that damped fluid pulsations was employed to create step increases in steady flow from 0 to 20 ml/min at 4 ml/min increments within the tube. The high percentage of solid components (no particle motion therein) made the flow index in the tube close to 0 when no flow motivation was induced by the pump. The noncontact probe was first calibrated to the homogeneous liquid phantom region to unify $\alpha D_B$ measurement for each S-D separation. The scanning procedure was linear as assumed in simulations. Total scanning time was 20 min with 60 s sampling time per step at 0.5 Hz DCS sampling rate for each laser. For each S-D pair, the interval average (60×0.5=30 points) represents the corresponding boundary measurement for that step. We used identical reconstruction parameters as the simulation including slab mesh and delay time t with the exception of a median filter application. This latter addition assisted in stabilizing inherent experimental noise not encountered in the ideal simulation.8 The relationship between macro pumped flow (unit: ml/min) and micro particle motion ($\alpha D_B$ unit: $cm^2/s$) is complicated, but was confirmed linear.[12] For this case, the assigned flow represents the macro flow (pump speed) rather than DCS indices. In FIG. 13(d), relative macro and micro flow changes were presented in the same way used in simulation. A tube-shaped anomaly was clearly recognizable after image reconstruction (FIG. 13(c)). The reconstructed flow indices accurately captured the flow changes in the tube when quantified with the peak value (FIG. 13(d); linear regression slope=0.97, $R^2$=1.00, and $p<10^{-5}$) and with the mean of segmented anomaly (data are not shown; linear regression slope=0.99, $R^2$=0.96, and $p<10^{-3}$). The liquid phantom system provided both a circumstance of complex dynamic particles and changes of particle motion and possesses the potential for easily updating tissue properties in both the background and the anomaly.

In the simulations and phantom tests, we note that no optical property mismatch between anomaly and background was induced, i.e., $\Delta\mu_s'$=0 and $\Delta\mu_a$=0. Our previous studies have revealed that the mismatch of $\mu_a$ and $\mu_s'$ resulted in estimation errors of DCS flow index.[10] To evaluate these influences on ncDCT, we carried out supplementary computer simulations and phantom experiments; the optical properties of background or anomaly were changed to create $\mu_a$ and $\mu_s'$ contrasts. We found that inaccurate $\mu_s'$ assumptions resulted in much greater flow index contrast errors than inaccurate $\mu_a$, which are consistent with our previous findings.[10] Nevertheless, the relative changes of reconstructed flow index contrasts over a large range of property contrast variations (2- to 3-fold) were accurately reconstructed even with the incorrect assumptions of optical properties (data are not shown). The problem of modeling such heterogeneity can be solved by combining DCT with other FD or time-domain DOT imaging instruments. To our advantage, the FEM-based implementation software proposed is fully capable of incorporating such arbitrary heterogeneities.

Previous DCT studies emphasized assigning a selective delay time t to each S-D pair based on the analytical or approximate solution of Eq. (2) which relies on simple geometry and optical properties as mentioned above.[6] By contrast, we propose to use a uniform T. From the view of $\mu_a^d(\tau)$, assigning uniform t unifies the $\mu_a^d(\tau)$ on the same time scale such that t does not generate extra $\mu_a^d(\tau)$ contrast. $\tau$ ($3.2\times10^{-6}$ s) was selected in this study based on a few simulations and exhaustive sensitivity optimization has not yet been completed. Specifically, we selected several small t values ($\tau\leq1.9\times10^{-5}$ s) from the entire range (generally from $1.0\times10^{-7}$ to $1.0\times10^{-3}$ s) to reconstruct flow contrasts in computer simulations for comparisons. The variations in the mean values and regression slopes of flow index contrasts reconstructed with different s were found to be 5±10% and <5%, respectively (data are not shown), indicating the robustness of ncDCT method in this range. Note that large t (e.g., $>1.9\times10^{-5}$ s) may lead to unstable results in reconstructed flow indices. Based on the definition of dynamic absorption $\mu_a^d(\tau)$ in Eq. (2), a large $\tau$ may result in an effective absorption ($\mu_a+\mu_a^d(\tau)$) greater than the normal range of tissue absorption, thus influencing the stabilities of forward and inverse solutions in NIRFAST. A good $\tau$ selection is complicated by considerations such as the occurrence of any weight distinctions or redundancies between equations generated by different $\tau$. This may be especially true when the flow contrast of the imaging anomaly differs greatly.

Furthermore, recruiting multiple s (assemble more equations at different time scales for each S-D pair) may promote robustness in solving an ill-posed inverse problem. These questions provide for further exploration.

In conclusion, we reported a ncDCT system for 3-D flow contrast imaging. A FEM framework was introduced to simulate temporal electric field autocorrelation diffusive transport and reconstruct spatially distributed flow contrasts. The imaging capability of flow contrasts was validated through both simulations and phantom experimentation. We tested the ncDCT system on a simple semi-infinite geometry herein, but by incorporating other imaging modalities (e.g., MRI and photogrammetric scanning) arbitrary geometry can be obtained. The noncontact breakthrough design enables potential imaging of deep blood flow contrast in real human tissues (e.g., breast tumor, pressure ulcer) without distorting hemodynamic properties.

References: 1 Yu, Curr. Med. Imaging Rev. 8(3), 194 (2012); 2 Li et al., Sci. Rep. 3, 1358 (2013); 3 Cheng et al., Neuroimage 62(3), 1445 (2012); 4 Lin et al., J. Biomed. Opt. 17(1), 010502 (2012); 5 Boas et al., J. Opt. Soc. Am. A 14(1), 192 (1997); 6 Culver et al., J. Cereb. Blood Flow Metab. 23(8), 911 (2003); 7 Zhou et al., Opt Express 14, 1125 (2006); 8 Dehghani et al., Commun. Numer. Methods Eng. 25(6), 711 (2009); 9 Durduran et al., Phys. Med. Biol. 47(16), 2847 (2002); 10 Irwin et al., Biomed. Opt. Express 2(7), 1969 (2011); 11 Fantini et al., J. Opt. Soc. Am. B 11(10), 2128 (1994); 12 Diop et al., Biomed. Opt. Express 2(7), 2068 (2011).

Ex. 3: Alignment of Sources and Detectors on Breast Surface for Noncontact Diffuse Correlation Tomography of Breast Tumors The altered tissue hemodynamics and metabolism in tumor pathogenesis have been well documented. It has been noted that the autonomic growth and spread of malignant tumors are partially dependent on increased angiogenesis arising from the increased metabolic demand[1-3]. Previous studies in breast cancer reported that hypermetabolism and increased angiogenesis were linked to increased blood flow, total hemoglobin concentration, and tissue metabolism[4-10]. For example, positron emission tomography showed significant tumor-to-normal tissue blood flow contrasts in breasts up to fivefold higher[4]. In carcinomas compared to benign lesions, flow velocities in large arteries adjacent to tumors acquired by Doppler ultrasound were significantly higher by up to threefold[9]. Thus, the functional imaging of tumor hemodynamics/metabolism is an exciting new strategy and provides a more finely grained and individualized understanding of cancer pathophysiology and treatment[11,12].

Near-infrared (NIR) diffuse optical spectroscopy/tomography (DOS/DOT) is a noninvasive, portable, and relatively inexpensive tool for functional imaging of deep tumor oxygenation[6-8,13-15]. NIR diffuse correlation spectroscopy/tomography (DCS/DCT) has also been developed more recently, which is capable of imaging blood flow distributions in deep tissues[16-23]. Most of these diffuse optical techniques deliver and receive NIR light using optical fibers placed on top of the tissue surface. These contact-based approaches may be disadvantaged for in vivo measurements due to the distortion of tissue hemodynamics resulted from the compression of probe contact on soft tissues with irregular boundaries. To overcome this limitation, our laboratory has recently developed a noncontact DCS/DCT (ncDCS/ncDCT) system for three-dimensional (3D) imaging of human tissue blood flow distribution without probe—tissue contact[24-26]. A finite element method (FEM)[27,28] based framework was also established facilitating ncDCT image reconstruction for tissues with arbitrary geometries[26].

This ncDCT system has been tested in tissue-like liquid phantoms with a simple semi-infinite geometry[26]. During the test, a motorized linear stage was employed to carry out ncDCT probe scanning over the flat surface of liquid phantoms. However, when applying the ncDCT system for in vivo investigations, the system must be modified to adapt to complex tissue boundaries. The goal of this study was to adapt the ncDCT system for the use of tumor detection in human breasts. For this purpose, we designed a motorized rotational stage to scan over the breast tissue and used a commercial 3D camera (NextEngine, California, USA) to obtain breast surface geometry. Several challenges exist when inputting the geometrical information to the FEM-based image reconstruction of ncDCT. First, the breast surface contour mesh generated by the 3D camera must be extended to a solid volume mesh to include the tissue volume imaged. Second, because the data from the 3D camera and ncDCT were collected in different coordinate systems, coregistration of the two coordinates is necessary. Finally, the projected sources and detectors of ncDCT (several hundreds of pairs) on the breast surface must be precisely aligned on the surface of solid mesh for the accomplishment of image reconstruction.

Computer-aided design (CAD) is a powerful tool for 2D and 3D solid modeling and coordinate transformation, and has been increasingly applied in the biomedical field [29,30]. The application programming interface (API) has been recently introduced to CAD software (e.g., SolidWorks, Dassault Systemes, Massachusetts, USA), which allows to access and control CAD software easily. In this study, we proposed a CAD-based approach to create the solid volume mesh from the surface contour mesh (generated by a 3D camera), to coregister the data obtained from the 3D camera and ncDCT, and finally to align the sources and detectors of ncDCT on the surface of the solid breast model.

We then evaluated the accuracy of source alignment on the breast surface as well as the influence of alignment errors on flow image reconstruction of breast tumor. This approach lays the groundwork of ncDCT for in vivo imaging of spatial blood flow distribution in breast tissues.

Methods and Materials

A. Motorized Rotational Probe for ncDCT Details about ncDCT can be found elsewhere [26]. FIG. 3 shows the rotational probe design of ncDCT for the imaging of tissue blood flow distribution in human breast. Two source fibers (WF200/220/245, CeramOptec, Massachusetts, USA) connected to two long-coherence lasers (785 nm, CrystaLaser, Nevada, USA) were projected alternatively onto the breast surface through achromatic lenses [FIG. 3(c)]. The detector fiber bundle [FIG. 3(b)] consisted of 15 single-mode fibers (SM800-5.6-125, Fibercore, California, USA), which were equally arranged in a 7 mm line to cover a 20 mm range through the magnification of lenses. A long-pass filter with a cutoff wavelength of 750 nm (FEL0750, Thorlabs, New Jersey, USA) was set in the detector path to reduce the influence of ambient light.

The probe head was adjusted to focus the source and detector fiber tips on the breast surface. Photons emitted from the lasers were injected alternatively through the two source paths into the tissue sample. Photons transported/scattered through the sample were eventually collected through the detection path by a linear detector array of 15 avalanche photodiodes (APDs, Perkin Elmer, Canada). The distance between the two projected sources was 40 mm and the resulting source-detector (S-D) separations were in the span of 10 to 30 mm [FIG. 3(c)]. A multichannel autocorrelator (Correlator.com, New Jersey, USA) took the 15 APD outputs and calculated the light intensity autocorrelation functions to extract blood flow index. A linear stage (5236A16, McMaster-Carr, Illinois, USA) and a custom-made rotational platform were used to manually align the line-shape probe at the initial scanning position of a selected region of interest (ROI) and approximately parallel to the breast tissue surface B. Scanning Procedure over Breast Tissue Surface. A breast model of a plastic mannequin placed on a bed was first used to explore the feasibility of the scanning protocol over the breast. A laser pointer inside the rotation arm was used to align the rotation axis approximately through the nipple [FIG. 3(a)].

The optical probe was then adjusted to make the two source chief rays approximately perpendicular to the surface of the mannequin breast. The probe scanned 60 deg over a ROI through 21 steps with a 3-deg increment per step. Total scanning time was i<<25 min with 60 s sampling time per step at 1 Hz sampling rate for each DCS laser source. The projected source pairs at the 1st, 11th, and 21st steps, as well as the rotation center, were visually marked on the breast surface using a marker pen.

After ncDCT probe scanning, the breast surface with marks was imaged by the 3D camera [FIG. 14(a)]. The camera operated at a working distance of ~17 in, and with a field of view (FOV) of 10 in×13 in. [see the inset in FIG. 14(a)] and an acquisition time of ~2 min. The mannequin was then removed from the bed and a small foam pad perpendicular to the rotation axis was attached to the DCS scanner [FIG. 14(b)]. The 3D camera took another image to include the small foam pad as a reference plane (RP), which was used for the coregistration of two coordinate systems: 3D camera and ncDCT. Note that the 3D camera was kept at the exact same position/location when taking the two images [FIGS. 14(a) and 14(b)].

After the feasibility test in the mannequin breast model, we used a similar but simplified protocol to scan over a ROI on a realistic human breast. A 22-year-old female subject who had a fibro-adenoma (benign tumor with no evidence of malignancy) in the breast volunteered to participate in this study after written consent in accordance with approval of the Institutional Review Board at the University of Kentucky. The subject lay supine on the bed comfortably and her body was fixed on the bed using soft form pads and pillows to reduce potential body motion artifacts during measurements. The tumor location was determined by ultrasound imaging, and the tumor mass margin along the longitudinal and latitudinal directions was marked on the ultrasound image. The ncDCT probe then scanned 60 deg over a ROI throughout 16 scanning steps with a 4-deg increment per step. This simplified protocol reduced the scanning time to ~17 min. Consequently, six marks of three source pairs were made at the 1st, 8th, and 16th steps. Following ncDCT scanning, in situ breast tissue optical properties (i.e., reduced scattering coefficient $\mu_s'$ and absorption coefficient $\mu_a$ were measured at three different locations by a commercial frequency-domain tissue oximeter (Imagent, ISS, Illinois, USA).

The averaged $\mu_s'$ and $\mu_a$ over multiple sites were used as initial inputs for flow image reconstruction. Finally, 3D camera scanning procedures were performed identically to those used in the mannequin breast model as described above. The total measurement time in the clinical room was ~25 min.

Figure 15:
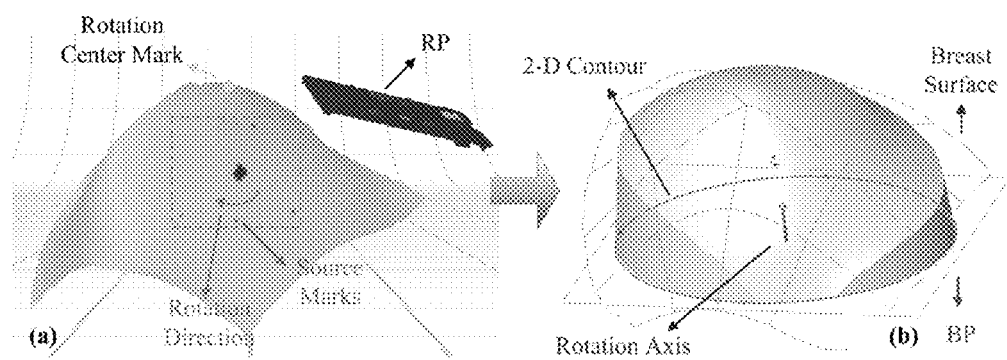
FIG. 15 shows procedures converting the acquired breast surface to a solid breast model for ncDCT image reconstruction. (a) The mannequin breast surface with source marks and the reference plane (RP) were integrated into one image. The three pairs of source marks and the rotation center mark can be clearly seen. (b) A bottom plane (BP) parallel to the RP was created and a 3-D solid breast model was then generated by extruding the 2-D contour on BP along the rotation axis to the 3D breast surface.

C. Solid Modeling of Breast Tissue Volume. For 3D flow image reconstructions, a solid breast model/mesh including the tissue volumes to be imaged is required. FIG. 15 illustrates the procedure to convert the mannequin (or human) breast surface image acquired by the 3D camera to a solid volume model. The 3D camera control software (ScanStudio HD, NextEngine, California, USA) generated a 3D surface mesh with three pairs of source marks and a rotation center mark [FIG. 15(a)]. The RP is also displayed in the figure. A non-uniform rational basis spline (NURBS) continuous surface was extracted by autofitting the nodes of the surface mesh. We then created a bottom plane (BP) parallel to the RP. The distance between the BP and the rotation center point was set as 50 mm. Finally, a solid breast model was generated by extruding a 2D circular contour on the BP along the rotation axis to the breast surface [FIG. 15(b)]. This solid breast model including the marked ROI was eventually used to generate a 3D tissue volume mesh for flow image reconstruction. The volume of the solid breast model was determined by the area of 2D circular contour, the angle of the extruding, and the distance between the BP and the rotation center point. These parameters should be selected individually to ensure photons being diffused sufficiently inside a relatively large tissue volume[31]. On the other hand, the tissue volume should be minimized to reduce the calculation burden for image reconstruction.

Figure 16:
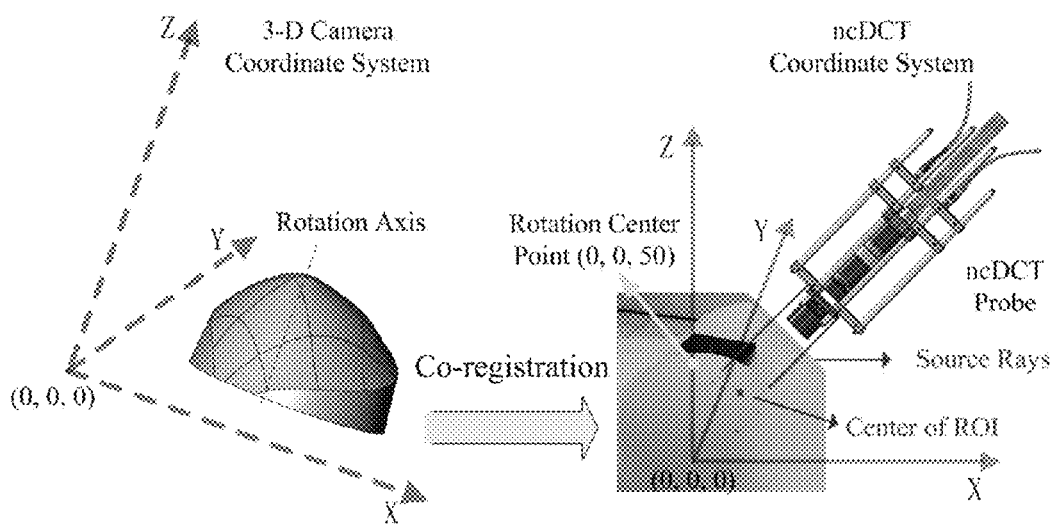
FIG. 16 shows coregistration procedures to place the solid breast model obtained in 3-D camera coordinate system (left) into the ncDCT coordinate system (right). The rotation center of the ncDCT probe obtained by the 3-D camera (left) was placed at (0, 0, 50 mm) in the ncDCT coordinate system (right).
Figure 17:
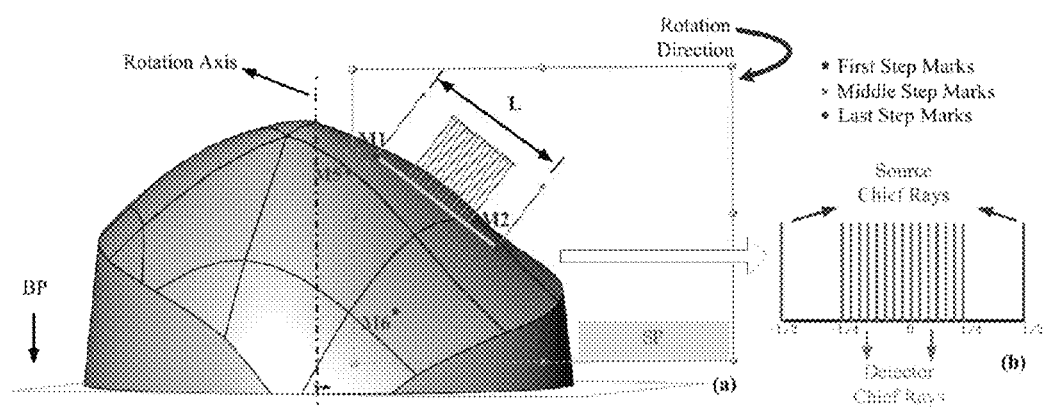
FIG. 17 shows alignment of sources and detectors of ncDCT on the surface of the solid breast model. (a) A scanning plane (SP) perpendicular to the BP and crossing the optical rays of sources and detectors was first aligned to pass through the initial pair of source marks (M1 and M2). (b) Each source or detector path was then simplified as a single chief optical ray perpendicular to the straight line connecting the source marks (M1 to M2). The sources and detectors along the chief optical rays were then projected onto the surface of the solid breast model. The SP was next rotated around the rotation axis step-by-step with a 3-deg increment per step for projecting sources and detectors at all scanning steps.

D. Coregistration of the Solid Breast Model and ncDCT Coordinate Systems. The breast surface imaging and ncDCT scanning were originally implemented in different coordinate systems (FIG. 16). For the coregistration of the two systems, we defined the x-y plane of the ncDCT coordinate system at the BP and z-axis along the rotation axis of the ncDCT. The coordinate of the rotation center was thus at (0, 0, 50 mm). The initial scanning position of the ncDCT linear array was aligned to the ncDCT system by adjusting the two source rays through the source marks made at the first step. This coregistration procedure allowed us to place the solid breast model into the ncDCT coordinate.

E. Alignment of Sources and Detectors on the Surface of the Solid Breast Model. For FEM-based ncDCT image reconstructions, sources and detectors must be projected on the breast tissue surface. We employed the CAD method operated by API to define a scanning plane (SP) perpendicular to the BP and passing through the initial pair of source marks [M1 and M2, FIG. 17(a)] and to mimic the probe scanning procedure over the breast surface.

Each source or detector path in the SP was simplified as a single chief optical ray [FIG. 17(b)] perpendicular to a crossing straight line (M1 to M2). The two sources were located at −L/2 and L/2 along the crossing line of length L and the 15 detectors spanned in the range of −L/4 to L/4. We then projected the sources and detectors along the chief optical rays onto the surface of the solid breast model. The projected points of intersection on the breast surface represented the aligned sources and detectors at the initial scanning step. The SP with source and detector rays was repeatedly rotated around the rotation axis for projecting sources and detectors at all scanning steps onto the surface of the solid breast model.

F. Evaluation of Source Alignment Errors. To characterize the alignment errors at different scanning steps, we quantified the distance from the aligned source points to the corresponding source marks. The absolute alignment error (σ: mm) was measured by the distance between the aligned and marked source points. The relative alignment errors were evaluated along the radial ($\gamma_{rad}$) and tangential ($\gamma_{tan}$) directions of the rotation by calculating the ratios of radial and tangential distance deviations ($\sigma_{rad}$ and $\sigma_{tan}$) to the measured radial and tangential distances ($l_{rad}$ and $l_{tan}$), respectively: $\gamma_{tan}=\sigma_{tan}/l_{tan}\times 100\%$; $\gamma_{rad}=\sigma_{rad}/l_{rad}\times 100\%$.

Figure 18:
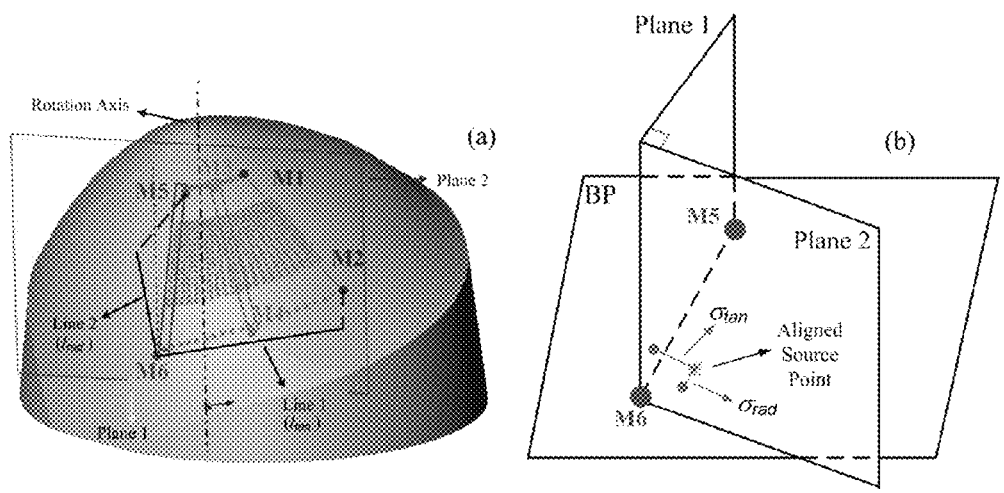
FIG. 18 shows characterization of source alignment errors at different scanning steps of ncDCT. (a) The projected source close to M6 is used for demonstration. Line 1 and Line 2 are perpendicular projections of M6-M2 and M6-M5 on the BP, respectively. The lengths of Line 1 and Line 2 are defined as $I_{tan}$ and $I_{rad}$, respectively. Plane 1 crosses M5 and M6 while Plane 2 crosses M6 and is perpendicular to Plane 1. Both Plane 1 and Plane 2 are perpendicular to the BP. (b) $\sigma_{tan}$ and $\sigma_{rad}$ are the distances between the aligned and marked source points along tangential and radial directions, respectively, which can be measured by the distances from the aligned source point to the Plane 1 and Plane 2, respectively
Figure 19:
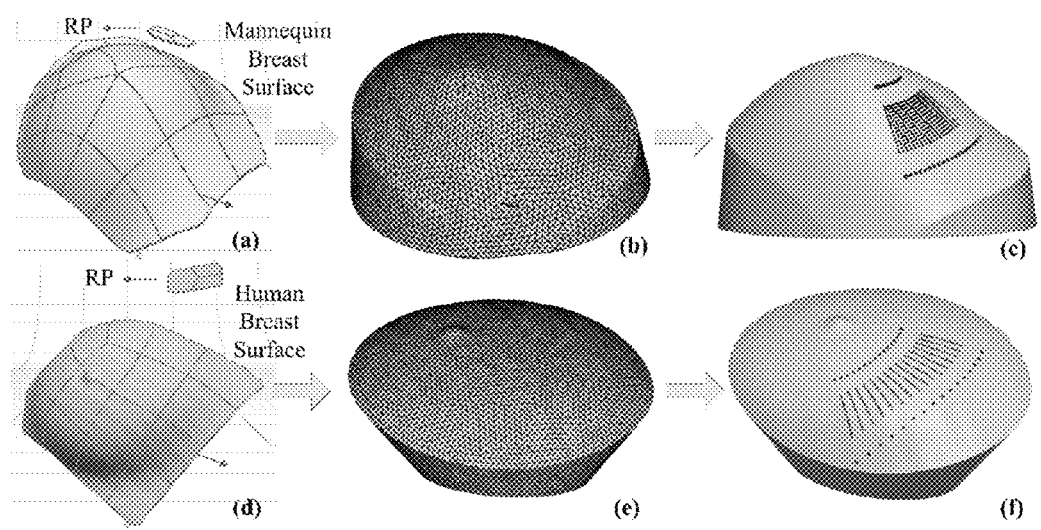
FIG. 19 shows ncDCT modeling procedures and results of solid breast meshes with the sources and detectors aligned on the mannequin (upper panel) and human (bottom panel) breasts. The images of mannequin (a) and human (d) breast surfaces and corresponding reference planes were obtained by the 3-D camera. The 3-D solid breast models were generated by extruding the 2-D circular contours on BP along the rotation axis to the breast surfaces. The breast volume meshes [(b) and (e)] were then created from the 3-D solid breast models. Finally, the sources and detectors were aligned on the surfaces of solid volume meshes [(c) and (f)].
Figure 20:
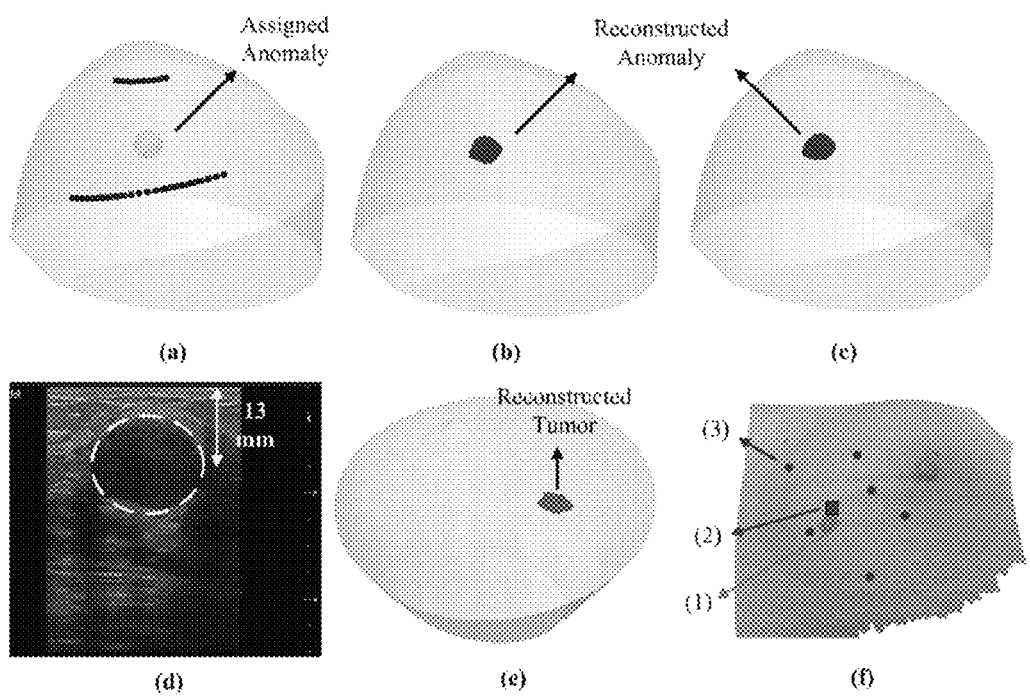
FIG. 20 shows ncDCT image reconstruction results from computer simulations (upper panel) and the human breast (bottom panel). (a) A breast mesh with an assigned sphere anomaly (radius=5 mm) at the center of the ROI and 8 mm beneath the surface of the mannequin breast. The red and blue dots represent the sources without and with alignment errors, respectively. The detectors are not shown for clarity. (b) Reconstructed anomaly using the sources and detectors without alignment errors. (c) Reconstructed anomaly using the sources and detectors with assigned alignment errors. (d) Ultrasound image of breast tumor (inside the dashed circle area) in the human subject. (e) Reconstructed human breast tumor using the solid breast mesh with the sources and detectors aligned on the human breast. (f) Comparison of tumor locations determined by ncDCT and ultrasound imaging on x-y plane: (1) the reconstructed tumor is projected on the breast surface, (2) the central location of the tumor determined by the ultrasound probe, and (3) source marks of ncDCT scanning.

FIG. 18 demonstrates how to quantify the relative alignment errors at the source mark M6. Briefly, two planes (Plane 1 and Plane 2) were set up to be perpendicular to the BP. Plane 1 crossed the mark pair of M5 and M6 along the radial direction while Plane 2 was crossing M6 and perpendicular to Plane 1 along the tangential direction. σ tan and σrad were the distances from the aligned source (nearby M6) to the two planes, respectively. $l_{rad}$ and $l_{tan}$ were the projected distances on the BP from M6 to M5 and from M6 to M2, respectively.

G. FEM-Based Flow Image Reconstruction of ncDCT. Details about the FEM-based forward and inverse solutions of ncDCT for blood flow imaging reconstruction can be found in our recent publications[26]. Briefly, the facilitation of DCT image reconstruction is accomplished through integration into an open software package for FEM-based DOT termed NIRFAST[27,28]. Exploiting the high mathematical similarity of the forward/inverse problems (e.g., boundary condition and mathematical assumptions) between DOT and DCT, we introduce a "dynamic absorption" of correlation with delay time due to dynamic processes of moving scatterers (primarily red blood cells). DCT can then be conceptualized as a modified formulation of DOT, which computes autocorrelation function instead of photon fluence rate. For computer simulations, the autocorrelation function can be generated using multiple delay times (e.g., 60 τ was used in this study) in the forward solution. For imaging reconstruction, the blood flow distribution can be extracted using the measured boundary data at multiple S-D pairs in the inverse solution.

3. Results

A. Solid Models with Aligned Sources and Detectors

The mannequin breast model and the human breast were used to demonstrate the CAD-based approach described earlier. FIGS. 19(a)-19(c) illustrate the modeling procedures and results obtained from the mannequin breast model. The 3D NURBS surface image [FIG. 19(a)] was transformed to the solid volume mesh by ANSYS (ANSYS, Pennsylvania, USA) with an average node distance of 2 mm [FIG. 19(b)]. The sources and detectors were then aligned on the surface of volume mesh [FIG. 19(c)]. Similarly, FIGS. 19(d)-19(f) illustrate the modeling procedures and results obtained from an in vivo human breast. The resulting volume meshes [FIGS. 19(c) and 19(f)] with sources and detectors aligned on their surfaces can be input into NIRFAST[27,28] for ncDCT image reconstructions[26].

B. Source Alignment Errors

Table 2 summarizes the measured radial and tangential distances ($l_{rad}$ and $l_{tan}$) at different source marks as well as corresponding absolute and relative alignment errors of the sources on the surfaces of mannequin and human breast. For both cases, the absolute errors (σ) increased with the increase of scanning step, which is expected as the alignment was calibrated on the first pair of source marks (M1 and M2). On average, the absolute error observed in the human breast (σ=2.64±1.65 mm) was larger than that in the mannequin breast (σ=0.79±0.50 mm). The mean relative error in the tangential direction ($\gamma_{tan}$=4.56±2.18%) was larger than that in the radial direction ($\gamma_{rad}$=2.43±1.17%), indicating the major contribution of tangential errors to the alignment errors. Similarly to the absolute errors, γ tan increased with the increase of scanning step and its mean value in the human breast (5.63±2.44%) was larger than that in the mannequin breast (3.50±1.48%).

TABLE 2

Absolute and Relative Alignment Errors between the Projected Sources and the Original Source Marks on the Mannequin and Human Breasts

| Case | Marks | σ(mm) | $\sigma_{tan}$ (mm) | $l_{tan}$ (mm) | $\gamma_{tan}$ (%) | $\sigma_{rad}$ (mm) | $l_{rad}$ (mm) | $\gamma_{rad}$ (%) |
|---|---|---|---|---|---|---|---|---|
| Mannequin | M3 | 1.34 | 0.23 | 9.24 | 2.48 | 1.06 | 35.33 | 3.00 |
|  | M4 | 1.25 | 0.64 | 23.87 | 2.68 | 0.75 |  | 2.12 |
|  | M5 | 1.79 | 0.84 | 14.79 | 5.67 | 1.04 | 32.46 | 3.20 |
|  | M6 | 2.56 | 1.43 | 45.03 | 3.17 | 1.09 |  | 3.35 |
| Human | M3 | 1.11 | 0.90 | 22.38 | 4.02 | 0.52 | 39.20 | 1.32 |
|  | M4 | 2.28 | 1.56 | 39.80 | 3.92 | 1.64 |  | 4.18 |
|  | M5 | 4.20 | 3.83 | 41.96 | 9.13 | 0.32 | 34.61 | 0.92 |
|  | M6 | 6.26 | 4.26 | 78.27 | 5.44 | 0.46 |  | 1.33 |

C. Impact of Source and Detector Alignment Errors on Flow Image Reconstruction

In order to evaluate the impact of alignment errors on imaging reconstruction of blood flow contrast, computer simulations were conducted on the mannequin breast [FIG. 20(a)]. A sphere anomaly with a radius of 5 mm was assigned to be 8 mm beneath the surface of the breast to mimic a breast tumor. A solid mesh was created with 4 mm node distance and was refined to 1 mm node around the known anomaly region (~20 mm radius) to improve detection resolution while not overwhelmingly increasing the number of nodes. For simplicity, optical properties for both anomaly and background were set throughout the tissue at $\mu_a$=0.06 cm$^{-1}$ and $\mu_s'$=6 cm$^{-1}$. The flow indices for background and anomaly were set as 1×10$^{-8}$ cm$^2$/s and 5×10$^{-8}$ cm$^2$/s, respectively, resulting in a relative flow contrast (rBF) of five-fold between the anomaly (tumor) and surrounding nodes (healthy tissues). We then assigned alignment errors of 10% in the rotation angles (i.e., 3.3° instead of 3°) for all sources and detectors at all scanning steps. For example, the source alignment errors at M5 and M6 were: $\gamma_{tan}$=10.55%; $\gamma_{rad}$=2.04% and $\gamma_{tan}$=9.85%; $\gamma_{rad}$=4.93%, respectively. The levels of these errors are consistent with our experimental results shown in Table 2. The impact of alignment errors on the tumor location and blood flow contrast was evaluated by comparing the reconstructed results with and without alignment errors.

FIGS. 20(b) and 20(c) show the reconstructed anomaly using the sources and detectors without and with alignment errors, respectively. The reconstructed anomaly centers deviated 1.30 mm (without alignment errors) and 2.07 mm (with alignment errors) from the assigned original coordinate [FIG. 20(a)], respectively. The shift of the anomaly central location (0.77 mm) was less than the node distance (1 mm). When using a full width half maximum (FWHM) threshold to segment the anomaly[32], the mean values of reconstructed flow contrasts were 5.63-fold and 5.68-fold, respectively. Thus, the deviation of average rBF contrasts caused by alignment errors was less than 1%.

D. In Vivo Breast Tumor Reconstruction Using ncDCT

FIG. 20(e) shows the reconstructed 3D flow contrast image of tumor inside the patient's breast using the FWHM threshold to segment the tumor. The central depth and dimension of the reconstructed tumor were 9.7 mm and 16.9 mm×15.5 mm, respectively. The measured $\mu_a$ and $\mu_s'$ of the breast tissue using the Imagent were 0.04 cm$^{-1}$ and 7.8 cm$^{-1}$, respectively, which were used as inputs for flow image reconstruction. The peak and averaged tumor-to-normal blood flow contrasts were 16.2-fold and 11.3-fold, respectively. The ultrasound image [FIG. 20(d)] shows a tumor with the dimension of 19.0 mm×18.3 mm at the central depth of 13.0 mm beneath the breast surface. FIG. 20(f) shows the reconstructed tumor projected on the surface of the breast, which agrees with the tumor location on the x-y plane determined by the ultrasound image.

4. Discussion and Conclusions

Most DCT measurements used optical fibers in contact with tissues for photon emission/collection and required tissues to conform to simple boundaries such as a slab. The compression on the tissue may introduce distortions in tissue hemodynamics[33]. An obvious solution to this problem is to place the sources and detectors away from the interface, allowing for the noncontact imaging of arbitrary boundaries. We have recently developed a noncontact DCT system and have demonstrated its feasibility for 3D imaging of flow contrasts in tissue phantoms with a simple flat surface[26]. Our ultimate goal is to translate this ncDCT system from benchtop to clinics for imaging of in vivo tissues with complex geometries such as human breasts.

This reports a critical step toward the translation of the ncDCT system for in vivo imaging of breast tumors. Currently, a variety of methods exist for obtaining irregular tissue geometries. Previous studies for DOT have used magnetic resonance imaging (MRI)[28,34,35] and computer tomography (CT)[36] to obtain solid volume meshes for imaging reconstruction. Hybrid systems combining DOT and MRI have also been reported recently[37-40]. However, the high cost, large instrumentation, and poor mobility of MRI or CT are major limiting factors for their frequent use in clinic. Only a few studies used 3D cameras to generate tissue surface geometries for DOT. For example, Dehghani et al. employed a 3D camera to scan over human breast surface before placing the source and detector fibers on its surface[41]. Obvious deformation of breast tissues was observed after placing the optical fibers for the contact DOT measurements. Previous fluorescence tomography studies in small animals (mouse or rat) used a 3D camera or CCD camera to acquire animal surface geometry, where the animals were either fixed in a small chamber[42,43] or rotated over 360 deg[44,45]. However, translation of these methods from small animals to humans is not straightforward since many constraining factors associated with human subjects must be considered, such as safety, flexibility, and comfort.

Our study utilized a 3D camera to obtain the surface geometry of the breast. The 3D camera can be placed at the bedside close to the subject, which makes the operation flexible in clinical rooms. The fully noncontact measurements by both 3D camera and ncDCT guarantee subject safety and comfort. The CAD-based approach with API allows us to convert the 3D surface profile to the 3D solid model, coregister the two coordinate systems (i.e., 3D camera and ncDCT), and align automatically the sources and detectors of ncDCT on the surface of the solid breast model.

Most of previous studies used a software such as Netgen[28], iso2mesh[46], or Matlab[43] to generate a volume mesh from the surface mesh obtained by a 3D camera[47] or CCD[44]. The source and detector locations on the surface of volume mesh were determined by ray tracing on the individual surface mesh nodes. Therefore, the accuracy of S-D alignment depended on the distance and distribution of surface mesh nodes. By contrast, we aligned the sources and detectors directly on the continuous surface (NURBS), which was extracted by autofitting the nodes of the surface mesh using CAD tools. Therefore, our alignment did not rely on the surface nodes. Furthermore, the CAD-based alignment method used in this study mimicked the same scanning procedure of the ncDCT probe, thus providing an easy way to assess the performances of scanning and alignment.

The accuracy of S-D alignment on the breast model is critical as it affects the accuracy of flow image reconstruction. Note that for simplicity the alignment accuracies in this study were characterized based only on the representative sources marked at the initial, middle, and final steps. We observed in this study that maximal alignment errors over scanning steps were less than 10%; i.e., 5.67% (mannequin) and 9.13% (human) in the tangential direction, and 3.35% (mannequin) and 4.18% (human) in the radial direction (Table 2). On average, the relative errors in the tangential direction were larger than those in the radial direction for both mannequin and human breasts, and the tangential errors increased with the increase of scanning step. These are expected since any imprecision of mechanically rotational scanning by the ncDCT probe should result in larger tangential errors along the rotation direction compared to the radial errors. Furthermore, the tangential errors may be accumulated with the increase of scanning step. By contrast, the radial errors are generally not accumulative as the length of the rigid scanning arm is fixed. In addition, perpendicularity between the rotation axis and the breast surface may also affect the alignment accuracy. The mechanical scanning errors can be reduced by using a high-precision motorized stage and the non-perpendicularity may be corrected by using an intelligent system to adjust the scanning axis based on a dynamic scanning of breast surface geometry.

It is also not surprising that the tangential errors observed in the human breast are larger than those found in the mannequin breast because some influencing factors may not be well controlled in human subjects, such as the irregular shape of a real breast as well as a subject's breathing or moving during the ncDCT measurement. However, the total averaging time of 60 s for blood flow measurement at each scanning step has greatly reduced the influence of a subject's breathing. To reduce potential motion artifacts resulted from body motion, we can re-mark source positions immediately after the body motion occurs and use difference marks for the alignment. Integration of all marked source positions for the alignment can increase the alignment accuracy, which will be the subject of our future work.

Computer simulations are commonly used to evaluate the performance of an imaging system. In this study, the impact of alignment errors on image reconstruction was determined by quantifying the deviations of central location and flow contrast of the assigned tumor inside the breast. The deviation of the reconstructed anomaly location (0.77 mm) resulting from the alignment errors was found to be smaller than the mesh node distance (1 mm) and the deviation of reconstructed flow contrast due to the alignment errors was less than 1%. Thus, the impacts of alignment errors on flow image reconstruction are ignorable.

The results from the patient with tumor demonstrate the feasibility of ncDCT in clinical use. The average tumor-to-normal blood flow contrast of 11.3-fold observed in this study is comparable to previously reported flow contrasts of 2- to 10-fold in breast tumors detected by DCS[10,48], noticing that tumor blood flow contrasts quantified by DCS may be underestimated due to the partial volume effect. In addition, the potential cross talk between $\mu_a$, $\mu_s'$, and blood flow may also result in overestimation or underestimation of blood flow contrasts[49]. When assuming homogeneous $\mu_a$ and $\mu_s'$ over the entire breast, the realistic heterogeneous $\mu_a$ and $\mu_s'$ over the tumor can generate errors in tumor blood flow contrast. To overcome this limitation, a separate DOT instrument enabling 3D imaging of $\mu_a$ and $\mu_s'$ distributions in the breast is needed[50,51].

The reconstructed tumor central depth of 9.7 mm is slightly shorter than the ultrasound finding (13.0 mm). This is likely due to the deep location of the tumor, which is slightly beyond the sensitive depth of diffuse light detected by our current ncDCT system. Based on photon diffuse theory, the penetration depth of diffuse light is ~½ of the S-D separation [49]. The largest S-D separation of current ncDCT is 30 mm, allowing for a penetration depth up to ~15 mm. It is thus not surprising that the reconstruction errors increased as the tumor (dimension based on ultrasound image: 19.0 mm×18.3 mm) center was located at a depth of 13 mm. In addition, noises from clinical measurements may also contribute to the reconstruction errors.

For the verification, we conducted computer simulations with the same size/location of a spherical anomaly (diameter=18 mm) as the human tumor and similar level of measurement noises. We observed that the reconstructed anomaly was located at ~10.9 mm beneath the breast surface with a diameter of 15.1 mm (data are not shown), which fairly agreed with our in vivo measurement results (i.e., tumor central depth=9.7 mm and dimension=16.9 mm×15.5 mm).

The focus of this study was to develop a CAD-based approach to align the sources and detectors of ncDCT on the surface of breast volume mesh for blood flow image reconstruction. We evaluated the accuracy of the source alignments using computer simulations and on a plastic mannequin and an in vivo human breast. Although we reported only one in vivo human case in this paper as an example, more simulations and in vivo imaging results from human breasts have been recently published by our group[52].

Theoretically, ultrasound imaging is not a part of ncDCT setup. However, given that fact that our ncDCT is the first optical imaging system providing 3D blood flow contrast distributions in breast tumors, we do need to compare our results with other standard imaging modalities (such as ultrasound photography) for validation. Also, ultrasound imaging of breast tumors helps us to determine the region of interest for ncDCT scanning. In addition, a priori knowledge of tumor location and volume can improve flow contrast reconstruction [52], which will be the subject of our future work.

In conclusion, we have developed a motorized rotational probe for ncDCT imaging of breast tissues and a CAD-based approach for the alignment of sources and detectors on the surface of solid breast models. The generated breast volume mesh along with the boundary data collected from the aligned sources and detectors can be used for FEM-based flow image reconstruction.

The results indicate that relative source alignment errors on both mannequin and human breasts are less than 10% throughout all scanning steps, which result in minor impact on flow image reconstruction. The recovery of in vivo breast tumor demonstrates the feasibility of ncDCT for clinical applications. Furthermore, the ncDCT system has the potential to be used for the imaging of deep blood flow distributions in a variety of soft or vulnerable tissues (e.g., breast tumor, pressure ulcer, burned tissue).

References: 1. Vaupel et al., Cancer Res. 49, 6449-6465 (1989); 2. Barrett et al., J. Magn. Reson. Imaging 26, 235-249 (2007); 3. Cuenod et al., Abdom. Imaging 31, 188-193 (2006); 4. Wilson et al., Int. J. Cancer 47, 344-347 (1991); 5. Intes et al., Acad. Radiol. 12, 934-947 (2005); 6. Ntziachristos et al., Neoplasia 4, 347-354 (2002); 7. Durduran et al., Opt. Lett. 30, 2915-2917 (2005); 8. Zhu et al., Radiology 266, 433-442 (2013); 9. Madjar et al., Gynecol. Oncol. 64, 392-403 (1997); 10. Zhou et al., J. Biomed. Opt. 12,051903 (2007); 11. Cyran et al., Radiat. Oncol. 9, 1-15 (2014); 12. Raje et al., Clin. Cancer Res. 14, 2387-2395 (2008); 13. Pogue et al., Radiology 218, 261-266 (2001); 14. Culver et al., Med. Phys. 30, 235-247 (2003); 15. Zhu et al., Radiology 237, 57-66 (2005); 16. Maret et al., Z. Phys. B 65, 409-413 (1987); 17. Pine et al., Phys. Rev. Lett. 60, 1134-1137 (1988); 18. Yodh et al., Phys. Today 48(3), 34-40 (1995); 19. Boas et al., Phys. Rev. Lett. 75, 1855-1858 (1995); 20. Li et al., J. Biomed. Opt. 10, 044002 (2005); 21. Sunar et al., J. Biomed. Opt. 11, 064021 (2006); 22. Diop et al., Biomed. Opt. Express 2, 2068-2082 (2011); 23. Culver et al., J. Cereb. Blood Flow Metab. 23, 911-924 (2003); 24. Lin et al., J. Biomed. Opt. 17, 010502 (2012); 25. Li et al., Sci. Rep. 3, 1-10 (2013); 26. Lin et al., Appl. Phys. Lett. 104, 121103 (2014); 27. Dehghani et al., Commun. Numer. Methods Eng. 25, 711-732 (2009); 28. Jermyn et al., J. Biomed. Opt. 18, 086007 (2013); 29. Kashefi et al., Acta Mech. Sin. 30, 259-273 (2014); 30. Chen et al., Med. Phys. 38, 6285-6299 (2011); 31. Busch et al., Acad. Radiol. 21, 151-161 (2014); 32. Dehghani et al., Appl. Opt. 42, 3117-3128 (2003); 33. Busch, Ph.D. thesis (University of Pennsylvania, 2011); 34. Brooksby et al., IEEE J. Sel. Top. Quantum Electron. 9, 199-209 (2003); 35. Srinivasan et al., Med. Phys. 34, 4545-4557 (2007); 36. Gibson et al., Phys. Med. Biol. 48, 481-495 (2003); 37. Li et al., Opt. Lett. 35, 3964-3966 (2010); 38. Mastanduno et al., Acad. Radiol. 21, 141-150 (2014); 39. Zhang et al., Rev. Sci. Instrum. 77, 114301 (2006); 40. Brooksby et al., Rev. Sci. Instrum. 75, 5262-5270 (2004); 41. Dehghani et al., Phys. Med. Biol. 49, 1131-1145 (2004); 42. Schulz et al., IEEE Trans. Med. Imaging 23, 492-500 (2004); 43. Kumar et al., IEEE Trans. Med. Imaging 27, 1152-1163 (2008); 44. Ducros et al., J. Biomed. Opt. 18, 020503 (2013); 45. Lasser et al., IEEE Trans. Med. Imaging 27, 188-194 (2008); 46. Fang et al., IEEE International Symposium on Biomedical Imaging, Boston, Mass. (IEEE, 2009), pp. 1142-1145; 47. Lapointe et al., Rev. Sci. Instrum. 83, 063703 (2012); 48. Choe et al., PLoS ONE 9, e99683 (2014); 49. Irwin et al., Biomed. Opt. Express 2, 1969-1985 (2011); 50. Choe et al., J. Biomed. Opt. 14, 024020 (2009); 51. Enfield et al., J. Biomed. Opt. 18, 56012 (2013); 52. He et al., J. Biomed. Opt. 20, 086003 (2015).

Ex. 4: Noncontact Diffuse Correlation Tomography of Human Breast Tumor

The current clinical standard for breast screening is x-ray mammography, with recent evidence confirming that mammograms offer substantial benefit for early cancer detection. However, mammography is hampered by a significant false-positive rate, which is especially high for women with dense breast tissue.

The dense breast population is a particularly important subset of women because they experience higher incidence and mortality rates from the disease.[1,2] Other imaging diagnostic tools for breast cancers include x-ray computed tomography (CT), magnetic resonance imaging (MRI), positron emission tomography (PET), and ultrasonography.[3-5] Most of these imaging methods are prohibitively expensive and generally only provide tumor morphological information with low specificity. Moreover, some of these techniques (e.g., CT and PET) expose patients to ionizing radiation.[6,7]

The autonomic growth and spread of malignant tumors are dependent on increased angiogenesis arising from the increased metabolic demand.[8] Since functional alternations in tumors often appear earlier than detectable morphological changes, functional imaging of tumor hemodynamics and metabolism is a new strategy for early cancer diagnosis.[9] Near-infrared (NIR) diffuse optical technologies provide a noninvasive and relatively inexpensive tool for functional imaging of tumor hemodynamics in deep microvasculature up to several centimeters.[10-13]

The most commonly used NIR diffuse optical spectroscopy/tomography (DOS/DOT) can quantify total hemoglobin concentration (THC) and blood oxygen saturation ($StO_2$) in tumors.[14,15] DOS/DOT has been used over several decades to detect oxygenation alternations in breast tumors.[16-20] For example, THC was found up to 2-fold higher in malignant lesions than nearby healthy tissues.[15] More recently, a novel NIR diffuse correlation spectroscopy (DCS) technique has also been developed for direct measurement of blood flow index (BFI) in deep tissues.[21]

A few pilot studies of breast tumors using DCS have found increased blood flow inside the tumor in contrast to surrounding normal tissues.[10] Real-time monitoring of breast tumor blood flow response to neoadjuvant chemotherapy also demonstrated the potential of DCS for assessing cancer therapies.[22,23]

Despite advances in DCS technologies, there have been limited imaging applications of diffuse correlation tomography (DCT) for tumor detection. An early probe-tissue contact-based DCT approach was applied to tissue phantoms[24] but was disadvantaged in vivo due in part to compression-induced hemodynamic alterations. A few noncontact-based DCT examinations have been conducted using the camera lenses positioned between a sample and optical fibers connected to source and detection elements.[25,26] These arrangements, however, were only tested on the brain of small animals with limited probing depth (<5 mm). Another limitation of these imaging studies was their reliance on analytical solutions that assumed a simple semi-infinite flat tissue geometry.

Our group has recently developed a novel noncontact DCT (ncDCT) system enabling three-dimensional (3-D) imaging of deep tissue blood flow distribution without contacting the tissue.[21,27,28] Our ncDCT system employs two sets of optical lenses to project source and detector fibers, respectively, onto the tissue surface. The separation of source and detector paths allows for the arrangement of large source-detector distances, thus enabling probing deep tissues up to centimeters. Furthermore, a finite-element-method (FEM) based facilitation of ncDCT image reconstruction for arbitrary tissue geometry is pioneered and integrated into an open software package (NIRFAST), designed originally for DOT.[29] Initial validation efforts for the innovative ncDCT system have been made using computer simulations and tumor-like phantoms on a simple slab-shaped tissue boundary (i.e., semi-infinite geometry).[21]

This reports our first step to adapt the ncDCT system for in vivo imaging of blood flow distribution in human breast tumors. We used a commercial 3-D camera (NextEngine, California) to obtain breast surface geometry and then converted it to a solid volume mesh for ncDCT image reconstruction.

Computer simulations were carried out to characterize the performance of an ncDCT system for imaging an anomaly (tumor) with varied flow contrasts and depths inside the tissue volumes under different surface boundaries. The malignant tumors inside human breasts (determined by ultrasound imaging) were then scanned using the ncDCT probe, and high tumor-to-normal flow contrasts were observed in the reconstructed images. To the best of our knowledge, we demonstrate, in this report, the first 3-D blood flow contrast imaging of human breast tumors using the noninvasive ncDCT.

Materials and Methods

Noncontact Diffuse Correlation Tomography System Instrumentation

As reported previously,[21] our ncDCT probe is a lens-focused apparatus, which has two identical source paths and one detector path configured in a linear array. In each source path, output from a multimode source fiber (WF200/220/245, Ceram-Optec, Massachusetts) connected to a laser (825 nm) on the DCS instrument is projected onto the tissue through lenses. Fifteen single-mode detector fibers (SM800-5.6-125, Fibercore, California) are equally spanned in the detector path connected to a detector array. The source-detector (S-D) separations vary from 10 to 30 mm, thus enabling up to ~15 mm penetration depth.[21] Two long coherence lasers at 825 nm (coherence length>5 m, CrystaLaser, Nevada) emit light to tissue through individual source paths, alternatively.

The photons traveling through the tissue sample are collected by the detector array of 15 avalanche photodiodes (APD, Perkin Elmer, Canada) through the detector path. A multichannel autocorrelator (Correlator.com, New Jersey) takes the APD outputs and calculates 15 correlation functions simultaneously. A motorized stage was integrated into the optical system, which rotates the ncDCT probe around the nipple for scanning a region of interest (ROI) on the breast surface. The outcomes from this scanning are the boundary data of intensity autocorrelation functions collected at hundreds of S-D pairs on the ROI (see the example in FIG. 25).

Diffuse correlation spectroscopy/diffuse correlation tomography principle and noise model was utilized using the algorithms described herein.

Figure 21:
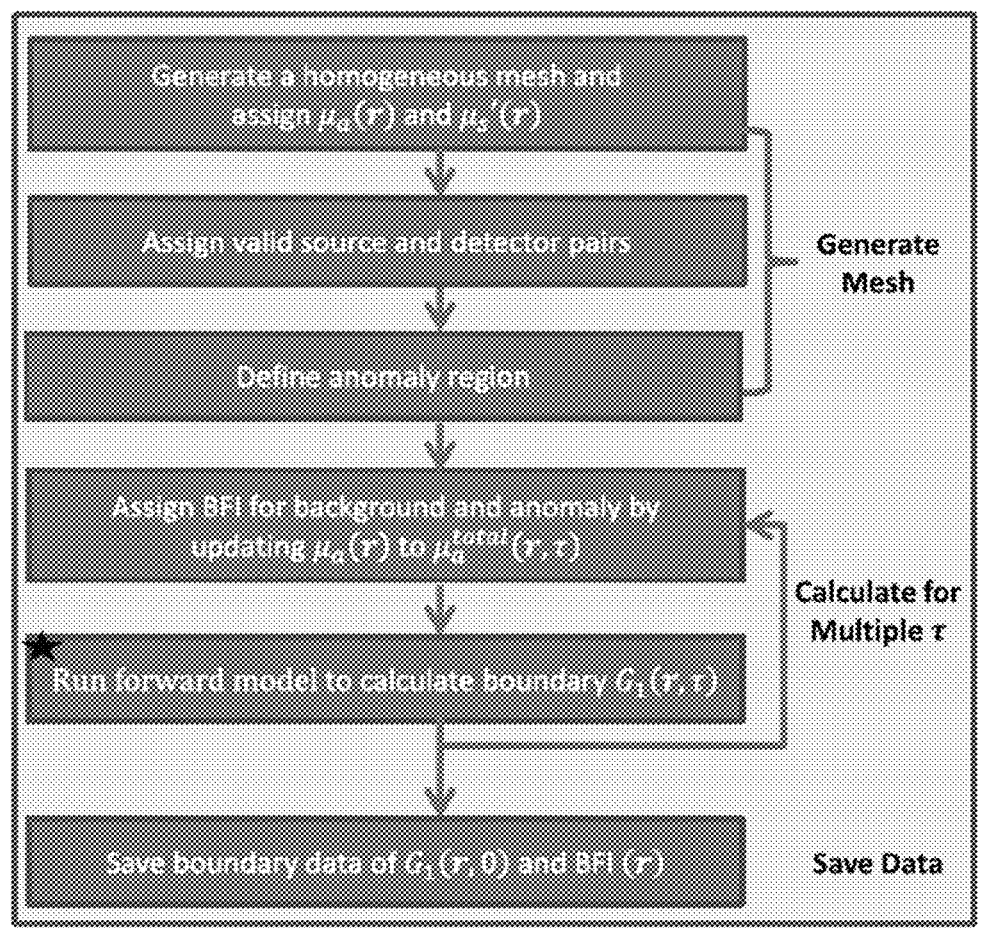
FIG. 21 shows a flowchart outlining the sequence and commands used in the modified NIRFAST to generate a forward model for ncDCT image reconstruction.
Figure 22:
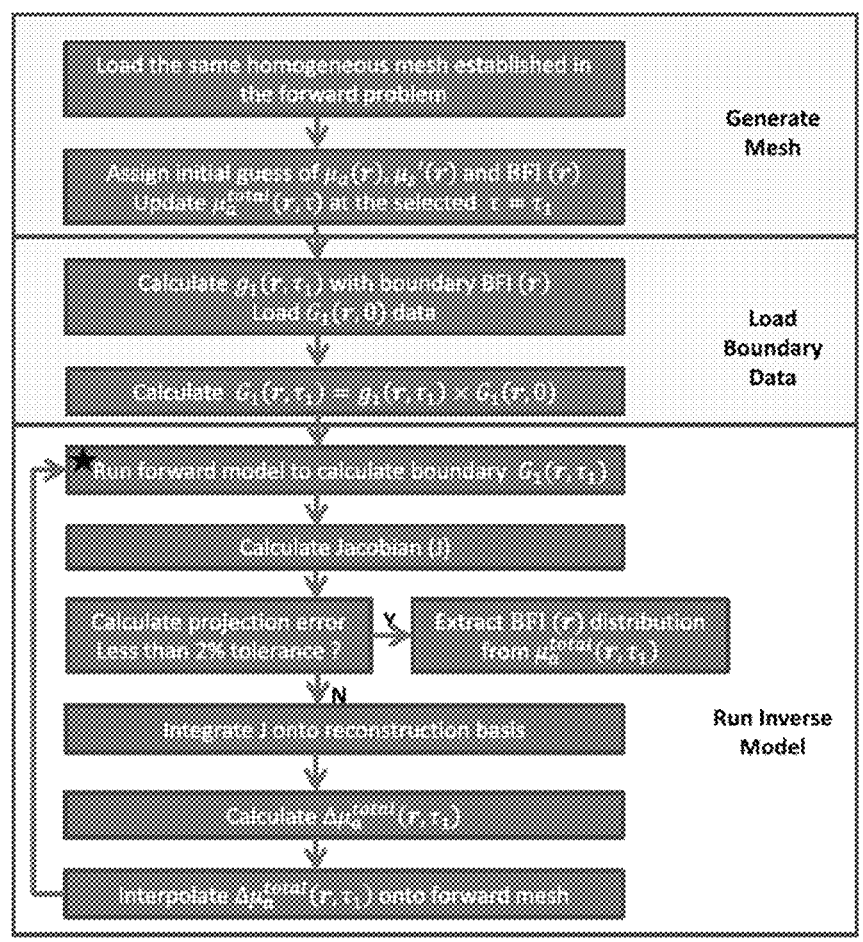
FIG. 22 shows a flowchart outlining the sequence and commands used in the modified NIRFAST to solve diffuse correlation tomography inverse problem for ncDCT image reconstruction.

FIGS. 21 and 22 illustrate the main commands executed for solving the forward and inverse problems, respectively, in ncDCT using modified NIRFAST. A homogeneous background tissue volume mesh with assigned initial optical properties of $\mu_a(r)$ and $\mu_s'(r)$ is first generated in the forward solution (see FIG. 21). All S-D pairs corresponding to the actual or simulated scanning of ncDCT probe are placed on the surface of the background mesh. However, only those with valid links between sources and detectors are configured as effective pairs for image reconstruction. An anomaly region (mimicking a tumor) inside the background volume mesh is then defined and assigned a BFI contrast relative to the surrounding background. Based on the designed distributions of BFIs, $\mu_a^{total}(r, \tau)$ is updated for each voxel inside the entire tissue volume within a certain range of $\tau$. The autocorrelation functions $G_1(r, \tau)$ for multiple t from all effective S-D pairs are then calculated by running the forward model. The boundary BFI data at all effective S-D pairs are then extracted by fitting $G_1(r, \tau)$ to the analytical solution of Eq. (2) under semi-infinite homogeneous geometry. It is noted that even though the forward problem simulates the light propagation in breast tumor models, some commands (e.g., "Run forward model . . . ") are also executed for experimental data reconstruction.

To evaluate noise influence on image reconstruction through simulations, randomized noise varying at different t is generated based on a noise model originally derived for DCS.[32,33] The noise level depends on the detected photon count rate (i.e., light intensity) at each S-D pair, which is estimated using the light intensity detected from in vivo breast tissues (see Sec. 2.3). This noise is applied to the simulated $g_2(r, \tau)$ curves. Multiple $g_2(r, \tau)$ curves with noise are generated for each S-D pair and then averaged to improve the signal-to-noise ratio (SNR). This simulation mimics our in vivo measurements and data averaging process in human breasts. Finally, $g_2(r, \tau)$ curves are converted to $G_1(r, \tau)$ curves to generate boundary BFI data.

Solving the inverse problem for image reconstruction is conducted on a second mesh with a coarse finite element division (pixel basis)[29,34] (see FIG. 22). Initial values of background BFI and optical properties [$\mu_a(r)$ and $\mu_s'(r)$] along with the selected $\tau$ ($\tau=\tau_1$ was specifically noted herein) are assigned to generate a homogeneous inverse mesh. The simulated or measured boundary BFI data are converted to $g_1(r, \tau)$ at the selected t using the semi-infinite analytical solution of Eq. (2),[27,33,35,36] and further converted to $G_1(r,\tau)$ by multiplying with $G_1(r, 0)$. The boundary $G_1(r, \tau)$ is then input into the inverse model to reconstruct the $\mu_a^{total}(r, \tau)$ distribution inside the entire tissue volume. The BFI distributions are finally extracted through the definition of $\mu_a^d(r, \tau)$.

Computer Simulation Protocols

We conducted several computer simulations to characterize the performance of the ncDCT system. The first simulation tested the abilities of ncDCT in recovery of an anomaly (tumor) beneath the surfaces of a slab and a female plastic mannequin breast (see herein). The second simulation evaluated the reconstruction accuracies of the anomaly with varied depths and flow contrasts in the same plastic mannequin breast. The influence of noise on ncDCT image reconstruction was also assessed and compared with the results without noise. The last simulation applied a priori structural knowledge of the anomaly in the inverse mesh to improve the accuracy of flow image reconstruction.

Reconstructions of a tumor in slab-shaped and breast-shaped tissues

To evaluate the reconstruction of an anomaly inside a background tissue volume with a simple semi-infinite geometry, a slab volume [dimension (mm): 100(H)×100(W)×40 (D)] was first generated in SolidWorksR (Dassault Systemes, Massachusetts) and then segmented into finite elements using ANSYSR (ANSYS, Pennsylvania). A total of 15,996 nodes were created with node distances of 3 and 6 mm in the ROI and the surrounding region, respectively [FIG. 23(*a*)]. Different mesh resolutions were employed to reduce the total node number while maintaining appropriate spatial resolution in the ROI. The segmented mesh nodes and elements information were then input into MATLABR (Math Works, Massachusetts) to generate all mesh files needed for the simulations with modified NIRFAST. The slab volume mesh represented a healthy background tissue volume. A spherical anomaly with a diameter of 10 mm mimicking a tumor was then placed at the ROI center, and the anomaly centroid location was 7 mm beneath the surface of background tissue volume [FIG. 23(a)]. Optical properties for both tumor and background tissues were set homogeneous throughout the entire slab as $\mu_s'$=6.00 cm$^{-1}$ and $\mu_a$=0.06 cm$^{-1}$.

The blood flow indices for the background and anomaly were set as $1\times10^{-8}$ cm$^2$/s and $10\times10^{-8}$ cm$^2$/s, respectively, resulting in a 10-fold flow contrast between the tumor and surrounding normal tissues [FIG. 23(c)]. The ncDCT probe with a linear S-D array scanning rotationally over the ROI was simulated for 21 steps with 3 deg/step to collect the boundary data [FIG. 23(a)], where coordinates were calculated with MATLAB. There were a total of 42 sources and 315 detectors distributed on the ROI. Thus, 630 (315×2) S-D pairs were effectively available and used for image reconstruction. The autocorrelation functions $G_1(r, \tau)$ from the effective S-D pairs were calculated by the modified NIRFAST software with t ranging from 0 to $3.2\times10^{-5}$ s (50 consecutive t). Reconstruction was conducted on the same mesh with a pixel basis of 20×20×25 and a $\tau_1$=8.7×10$^{-6}$ s. The t selection has been discussed in our previous publication.[21] The presenting anomaly was extracted with the full-width at half-maximum (FWHM) criterion[37] on the reconstructed DCT image. The averaged BFI and the center location of the reconstructed anomaly were computed by averaging the BFIs and node coordinates within the anomaly.

In order to assess the ability of ncDCT for imaging a tumor inside breast, we conducted a computer simulation on a female plastic mannequin breast. The surface geometry of the mannequin breast with source marks of ncDCT was scanned by a commercial 3-D camera (NextEngine, California), which was further converted to a solid breast tissue volume using Solid Works. To align the sources and detectors of ncDCT on the breast model surface for image reconstruction, a scanning plane perpendicular to the breast surface and crossing the optical rays of 2 sources and 15 detectors was created in SolidWorks.

The scanning plane was first aligned passing through the first pair of source marks and then rotated step-by-step around the rotation axis with an angle increment of 3 deg, matching our experimental procedure [FIG. 23(a)]. At each step, the sources and detectors along the optical rays were projected onto the surface of the solid breast model.

Similar to the slab meshing, the solid breast volume was segmented into finite elements with node distances of 3 and 6 mm in the ROI and surrounding region. A solid volume mesh [largest dimension (mm): 100(H)×78(W)×70(D)] with total nodes of 14,717 was generated for simulations. A spherical tumor with a diameter of 10 mm and a node distance of 3 mm was then placed at the ROI center, and the tumor centroid location was 7 mm beneath the breast surface [FIG. 23(e)]. For comparisons, we assigned the same optical properties and BFI contrast as those used in slab-tissue simulation. The boundary data were also collected in the same manner over the ROI on the breast surface. Identical breast-shaped mesh with a pixel basis of 20×20×30 and $\tau_1$=8.7×10$^{-6}$ s were used for image reconstruction.

Quantification of Tumor Location and Flow Contrast in the Breast-Shaped Tissue

This simulation used the same tumor model in the breast-shaped mesh with the same configuration and optical properties [see FIG. 23(e)]. The tumor was placed beneath the surface of the breast-shaped mesh with varied central depths from 7 to 15 mm at 1 mm increment/step. It is noted that breast tumors with their centroid locations within the sensitive region of diffuse light (i.e., the detected penetration depth of NIR light is ~½ of the S-D separation)[35,38,39] were our most interested study population, since more reliable reconstructions can be generated. At each depth, the tumor-to-normal flow contrast was increased from 0- to 20-fold at 5-fold increment/step. The reconstructed tumor depth was characterized as the shortest distance from the reconstructed anomaly center to the breast mesh surface.

The measurement accuracy of the ncDCT system was assessed by quantifying the discrepancies between the reconstructed and assigned values in tumor central location and flow contrast.

To evaluate the noise influence on image reconstruction, we added noise on the subsets of boundary data collected from the tumor with 10-fold flow contrast throughout all varied depths. Forty $g_2(r, \tau)$ curves with noises were generated and averaged at each effective S-D pair for DCT image reconstruction.

Reconstruction with a Priori Knowledge of Tumor Location and Volume

To improve the reconstruction accuracy of anomaly blood flow contrast, the soft-constraint method[37,40-42] in NIRFAST package was tested in this simulation. A priori structural information of tumor (i.e., central location and tumor volume) was included in the inverse mesh by labeling the nodes in the inverse mesh according to the regions of tumor or surrounding tissues. A regularization matrix L was applied to the penalty term in the minimization function for the DCT inverse problem, which was equivalent to applying a Laplacian-type filter to minimize variation within each region.

Simulations were done with the spherical anomaly (10-fold flow contrast and diameter=10 mm) placed at either 7 or 15 mm central depth beneath the breast surface and with or without noise.

In-Vivo Blood Flow Imaging of Human Breast Tumor

To explore the feasibility of an ncDCT imaging system in clinical applications, two female patients with low-grade carcinoma were recruited from University of Kentucky Comprehensive Breast Care Center, with signed informed consent approved by the University of Kentucky Institution Review Board. The patient lay in a supine position and the major tumor lesion inside the breast was determined by radiologists using ultrasound imaging prior to the optical measurement. The tumor mass margins along the radio direction were marked on the ultrasound images.

The ncDCT probe was driven by a step motor to scan rotationally around the breast nipple over the region of breast tumor. The scanning procedures were similar to those described herein. Briefly, 15 and 21 scanning steps were taken to cover the tumor bearing regions in the two breasts, respectively.

Forty $g_2(r, \tau)$ curves were collected from each S-D pair for each patient, and two source pairs at the beginning and ending steps of scanning were visually marked on the breast surface as the references for the alignment of sources and detectors on the surface mesh. The surface geometry of the breast with the source marks was then recorded by the 3-D camera for image reconstruction. Following the ncDCT measurement, a commercial frequency-domain tissue oximeter (Imagent, ISS, Illinois)[43] was used to measure $\mu_s'$ and $\mu_a$ of the breast tissue at three different locations. The averaged $\mu_s'$ and $\mu_a$ over the multiple sites were used as initial inputs for flow image reconstruction.

The solid breast mesh of the patient was created in the same way as that of the plastic mannequin breast. Boundary BFIs on the breast mesh surface were then extracted by fitting the measured $g_2(r, \tau)$ curves from effective S-D pairs. These boundary BFI data were then calibrated to the BFIs collected at the first scanning step, where the tissue underneath the probe was outside the tumor region and thus assumed to be homogeneous and healthy. The calibrated boundary data were finally used for DCT image reconstruction.

Results

Figure 23:
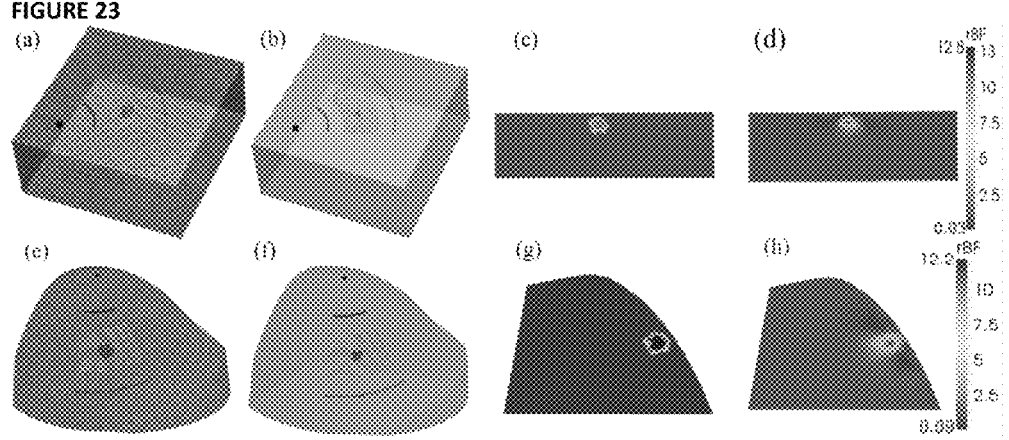
FIG. 23 shows recovery of anomaly blood flow contrasts inside the slab-shaped and breast-shaped volume meshes for ncDCT image reconstruction. A sphere anomaly with a diameter of 10 mm and 10-fold flow contrast was placed at 7 mm beneath the surface of background tissue volumes. (a) and (e) show the original assigned anomalies inside the volume meshes with sources and detectors aligned on the mesh surfaces; (b) and (f) show the reconstructed anomalies with full-width at half-maximum (FWHM) thresholds; (c) and (g) show 2-D cross-section views of original flow contrast distributions through the anomaly centers; (d) and (h) show the 2-D cross-section views of reconstructed flow contrast distributions.

Noncontact Diffuse Correlation Tomography Recovered an Anomaly Inside Both Slab-Shaped and Breast-Shaped Tissue Volumes with Similar Accuracies in Simulations FIG. 23 illustrates 3-D [FIGS. 23(a), 23(b), 23(e), and 23(f)] and two dimensional (2-D) cross-section [FIGS. 23(c), 23(d), 23(g), and 23(h)] views of blood flow distributions in the slab-shaped (top panel) and breast-shaped (bottom panel) tissue volumes, respectively. FIGS. 23(a), 23(e), 23(c), and 23(g) show the originally assigned/simulated anomaly inside tissue volumes and FIGS. 23(b), 23(f), 23(d), and 23(h) show the reconstructed results for comparisons.

To clearly visualize the anomaly inside the tissue volume, 3-D background meshes were presented with 30% transparency of their original colors. The reconstructed anomalies were presented with FWHM thresholds in 3-D images [FIGS. 23(b) and 23(f)] and without thresholds in 2-D cross-section views [FIGS. 23(d) and 23(h)]. Table 3 summarizes the discrepancies between the assigned and reconstructed anomalies inside the slab-shaped and breast-shaped tissue volumes. These results indicate that the ncDCT system can recover the anomaly inside both slab-shaped and breast-shaped tissue volumes with similar accuracies.

TABLE 3

Computer simulation results in recovering an anomaly[a] inside slab-shaped and breast-shaped volume meshes

| | Anomaly central depth (mm)/ % error | Anomaly diameter (mm)/ % error | Peak flow contrast/ % error | Average flow contrast/ % error |
|---|---|---|---|---|
| Slab-shaped | 6.4/8.6% | 7.2/28% | 12.8-fold/28% | 9.3-fold/7% |
| Bread-shaped | 6.65/7% | 7.5/25% | 12.2-fold/23% | 8.1-fold/19% |

[a] A spherical anomaly with a diameter of 10 mm and 10-fold flow contrast was placed at 7 mm beneath the surface of background issue volumes.

Figure 24:
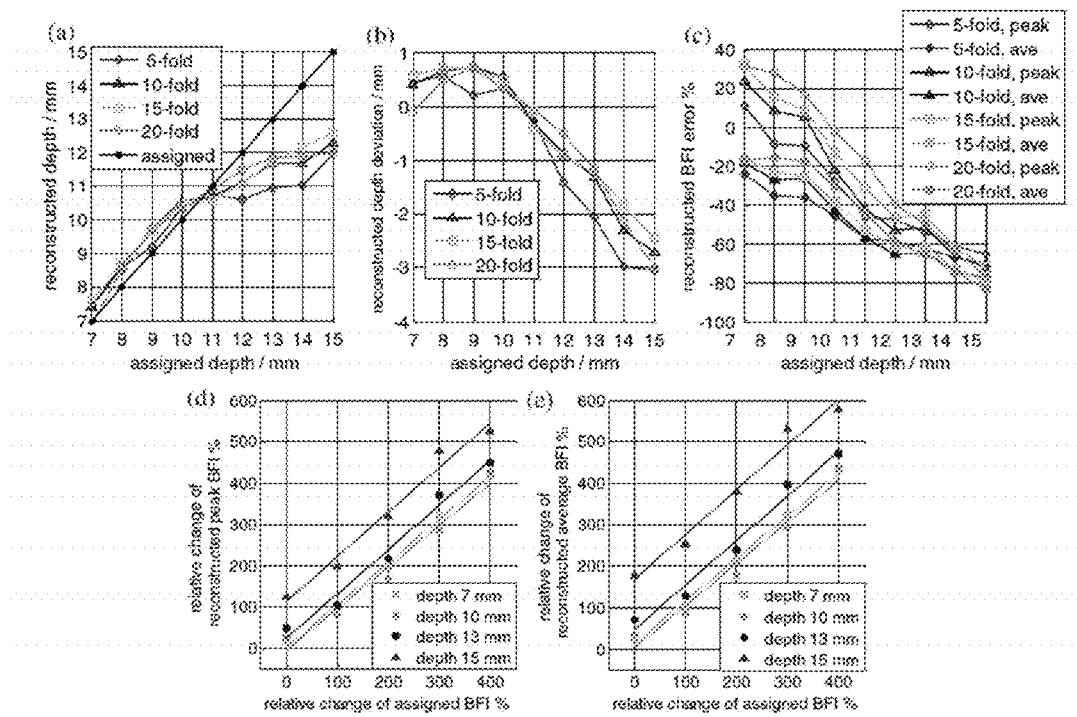
FIG. 24 shows evaluation of reconstruction accuracy of ncDCT in the breast-shaped volume mesh. (a) and (b) show the center location and deviation of the reconstructed anomaly at different depths; (c) shows the percentage deviations of anomaly peak and average blood flow index (BFI) contrasts at different depths; (d) and (e) show the linear relationships between the assigned and reconstructed peak and average BFI contrasts at different depths.

Higher Reconstruction Accuracy Achieved in Simulations when the Anomaly was within the Sensitive Region of Diffuse Light The reconstruction results with varied anomaly locations and flow contrasts are presented in FIG. 24. The discrepancies [FIG. 24(b)] between the reconstructed and assigned central locations of the anomaly were smaller than the mesh node distance (3 mm) at all depths. The reconstructed anomaly locations were more accurate in the sensitive region of diffuse light (errors 0.5 mm at central depths 10 mm) compared to those in deeper depths.

Reconstruction errors in peak and average BFI contrast of the anomaly at varied center location and assigned flow contrasts are displayed in FIG. 24(c). The largest reconstruction errors in peak and average flow contrasts ranged from 31.4% to −77.0% and −23.6% to −82.9% respectively, through all varied depths and flow contrasts. Similarly, the reconstructed peak and average BFI contrasts were more accurate in the sensitive region of diffuse light (peak and average BFI underestimations 27.8% and 45.3%, respectively, at central depths 10 mm) compared to those in larger depths.

FIGS. 24(d) and 24(e) demonstrate the linear relationships between the assigned and reconstructed peak and average BFI contrasts. The relative anomaly flow contrast changes were well reconstructed from the chosen central depths of 7 mm (peak BFI: linear regression slope=1.03, $R^2$=0.99, and p<0.001; average BFI: linear regression slope=1.02, $R^2$=0.99, and p<0.001), 10 mm (peak BFI: linear regression slope=1.01, $R^2$=0.97, and p<0.01; average BFI: linear regression slope=1.00, $R^2$=0.97, and p<0.01), 13 mm (peak BFI: linear regression slope=1.07, $R^2$=0.98, and p<0.01; average BFI: linear regression slope=1.07, $R^2$=0.98, and p<0.01), and 15 mm (peak BFI: linear regression slope=1.08, $R^2$=0.98, and p<0.01; average BFI: linear regression slope=1.08, $R^2$=0.98, and p<0.01). The relationships between the assigned and reconstructed relative anomaly flow contrast changes from other tested depths were similar (results not shown here).

In total, these results indicate that relatively higher accuracies were achieved when the entire anomaly was within the sensitive depth of diffuse light. Also, even though the recovery of anomaly BFI contrasts was not as accurate as its location, the reconstructed anomaly BFI contrast changes were fairly accurate.

Noise Reduced Anomaly Recovery Accuracy in Simulations

Figure 25:
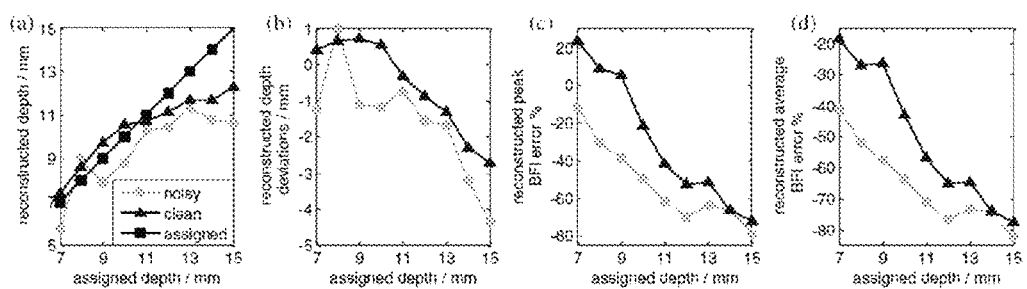
FIG. 25 shows noise influence on imaging accuracy of ncDCT. An anomaly was placed beneath the surface of the breast-shaped mesh with varied central depths from 7 to 15 mm. (a) and (b) show the center location and deviation of the anomaly at different depths, reconstructed with or without noise. (c) and (d) show percentage deviations of anomaly peak and average BFI contrasts at different depths, reconstructed with or without noise.

FIG. 25 shows the ncDCT image reconstruction results with simulated noise added to the forward problem. For comparisons, images reconstructed from clean data (no noise) and noisy data are plotted together. When the anomaly volume was within the sensitive region of diffuse light (anomaly central depth 10 mm), the largest discrepancy between the reconstructed and assigned central locations of the anomaly was 1.2 mm [FIG. 25(b)], 0.8 mm greater than that (0.4 mm) without noise. Similarly, the largest reconstruction errors in peak and average flow contrasts were 33.2% and 31.0% larger than those reconstructed without noise [FIGS. 25(c) and 25(d)]. Apparently, adding noise reduced reconstruction accuracies in recovery of the anomaly. However, the major conclusions drawn herein are still valid.

Figure 26:
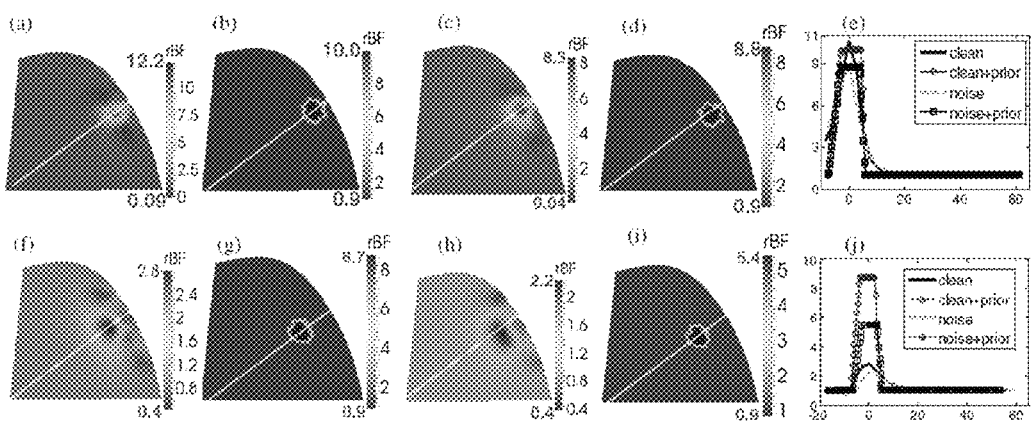
FIG. 26 shows comparison of anomaly reconstructions without and with a priori structural information for ncDCT. The top [(a)-(e)] and bottom [(f)-(j)] panels show the reconstructed flow contrast distributions of an anomaly (assigned a 10-fold flow contrast) located at 7 and 15 mm central depths, respectively. (a) and (f) show reconstructed results without the a priori structural knowledge of the anomaly; (b) and (g) show the reconstructed results with the a priori structural knowledge; (c) and (h) show the reconstructed results without the a priori structural knowledge and with noise. (d) and (i) show the reconstructed results with the a priori knowledge information and with noise. The flow contrast profiles crossing the yellow lines are shown in (e) and (j).
Figure 27:
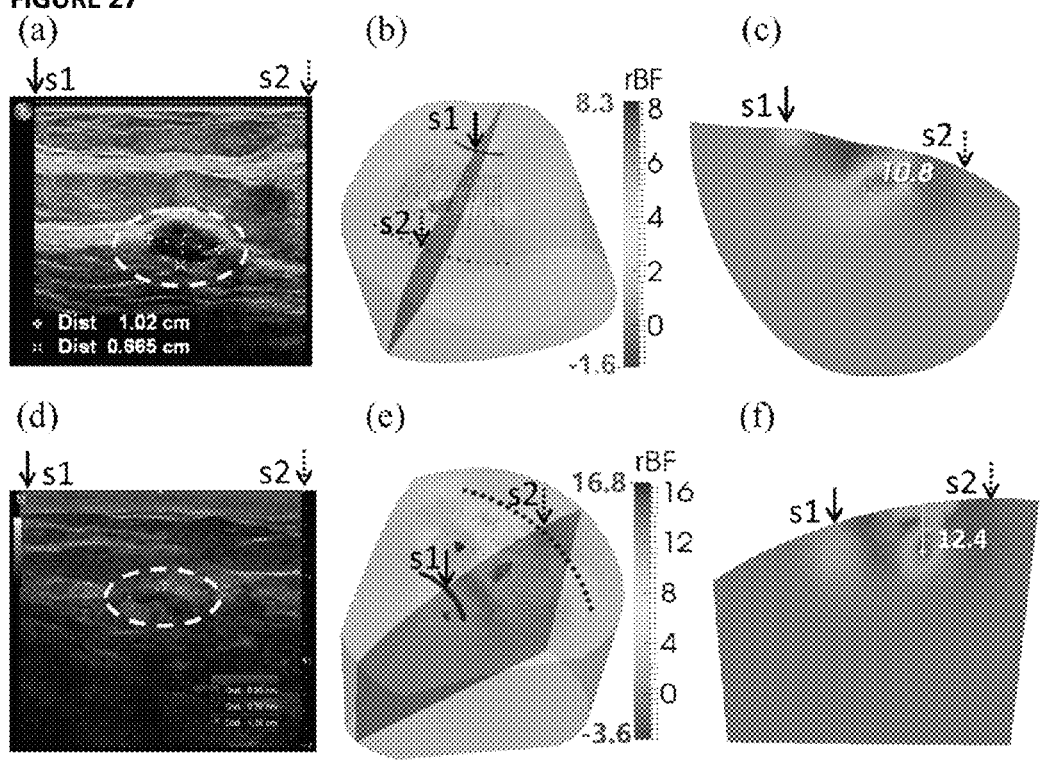
FIG. 27 shows clinical examples of two low-grade carcinomas in situ using ncDCT. (a) Patient 1 (P1) ultrasound image taken from radio direction shows a 10.2×6.65 mm$^2$ oval mass (inside the yellow dashed circle) with circumscribed margins parallel to the skin. The mass center is located at 19.2 mm beneath the skin surface. A core biopsy revealed a ductal papilloma with low-grade ductal adenocarcinoma in situ. (d) Patient 2 (P2) ultrasound image shows an 8.5×3.5 mm$^2$ mass (inside the yellow dashed circle), located at 13.3 mm beneath the skin surface. A core biopsy revealed atypical ductal hyperplasia and low-grade carcinoma in situ. (b) and (e) show the reconstructed 3-D tumor blood flow contrasts with FWHM thresholds for P1 and P2, respectively. The backgrounds are presented with 30% transparency of the original color clarity. For the comparison of ultrasound and ncDCT results, an ultrasound imaging plane along the transducer line and across the overlapped two specific sources (S1 and S2) is presented in the 3-D reconstructed image. (c) and (f) show the cross-section views of tumor flow contrast images through the ultrasound imaging planes, which can be directly compared to the 2-D ultrasound tumor images [(a) and (d)], respectively.
Figure 28:
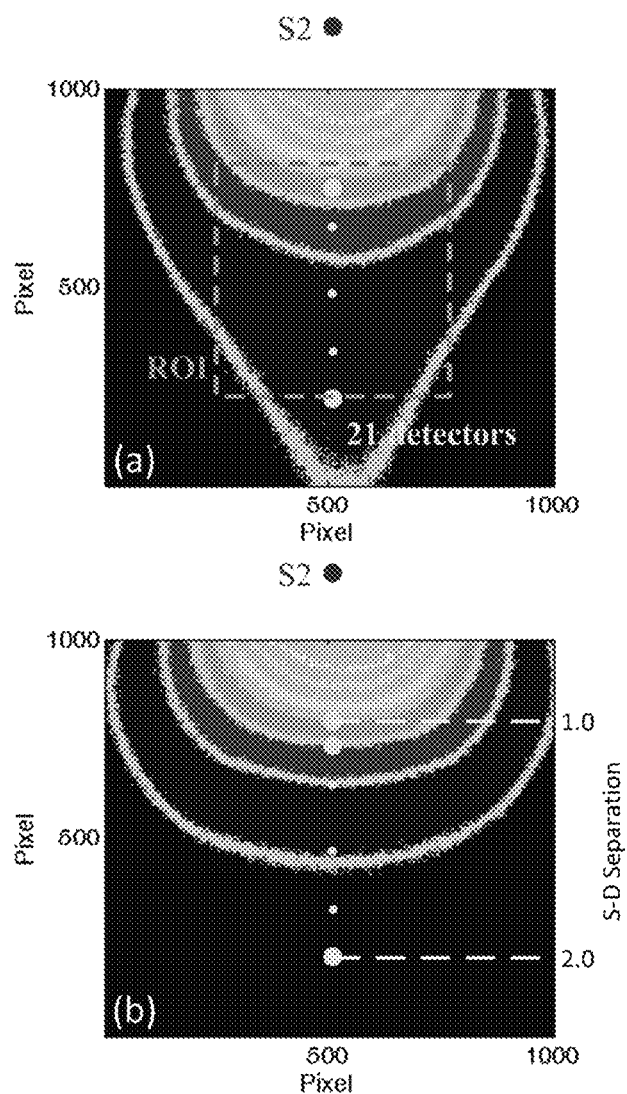
FIG. 28 shows results measured by scDCT. (a) Original intensity pattern for source S2 on the homogeneous phantom using scDCT. (b) Desmeared intensity distribution of (a) with a corresponding S-D separation axis. These images depict contours of the intensity profiles with dots representing 21 effective detectors for demonstrating the K distribution with the S-D separations. Note that the dots are not to scale and the smaller dots serve as an ellipsis for the intermediate detectors.
Figure 29:
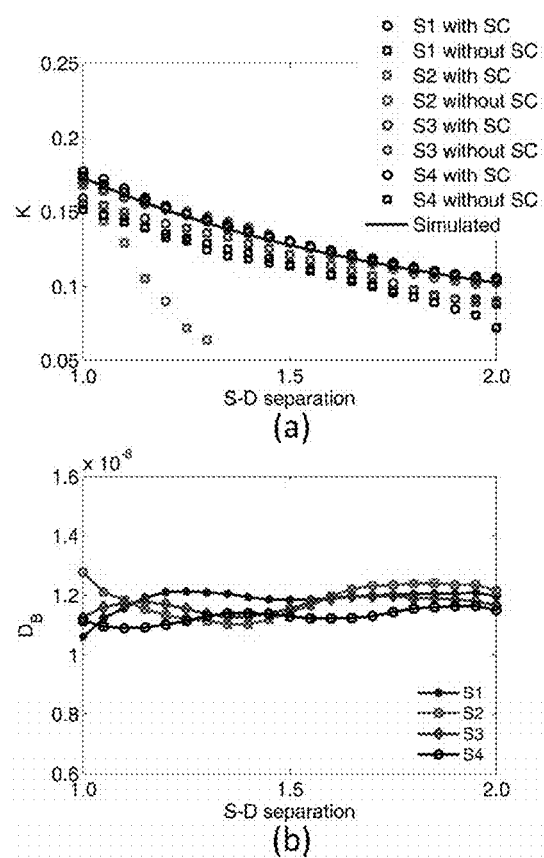
FIG. 29 shows results measured by scDCT. (a) K for all sources from detectors defined along the center row with and without smear correction (SC) and numerically simulated K at the S-D separations. (b) $D_B$ for center row detectors.

A Priori Knowledge of Anomaly Location and Volume Improved Flow Contrast Reconstruction in Simulations FIG. 26 demonstrates the improvements in the reconstruction of BFI contrasts using a priori knowledge of tumor location and volume in DCT image reconstruction. The top [FIGS. 26(a)-26(e)] and bottom [FIGS. 26(f)-26(j)] panels show the reconstructed results when the anomaly is at the central depth of 7 and 15 mm beneath the surface, respectively. In each panel, image results without/with a priori information and without/with noise are plotted, respectively. The transect plots [FIGS. 26(e) and 26(j)] show the BFI distributions across the anomaly. The reconstruction accuracies in BFI contrasts were significantly improved when a priori knowledge of anomaly structural information was applied on data with and without noise. The peak/average BFI contrast errors were only 0.1%/4% (without noise) and 12.3%/12.3% (with noise), respectively, when using a priori structural information for the anomaly located in the sensitivity region of diffuse light [i.e., at the central location of 7 mm, FIG. 26(e)]. The BFI contrast improvement at the deeper central depth of 15 mm was also remarkable [FIG. 26(j)].

High Blood Flow Contrasts were Observed in Human Breast Tumors

Two patients with low-grade carcinomas were imaged with our ncDCT system [FIGS. 27(b), 27(c), 27(e), and 27(f)]. The first patient (P1) was a 59-year-old female who had ductal papilloma and low-grade adenocarcinoma in situ. According to the ultrasound imaging [FIG. 27(a)], the lesion with the dimension of 10.2×6.65 mm² was located at 19.2 mm beneath the skin surface. For the comparison of ultrasound and ncDCT results, the cross-section view of tumor flow contrast image through the ultrasound imaging plane (along the line of ultrasound transducer) and across the overlapped two ncDCT sources (S1 and S2) is presented in the reconstructed 3-D image [FIG. 29(b)]. The dimension of the reconstructed tumor by ncDCT with the FWHM threshold was approximately 15.1×5.8 mm² [FIG. 27(c)], which matched the ultrasound image [FIG. 29(a)]. However, the reconstructed tumor central location was 10.8 mm beneath the breast surface, which differed from the ultrasound image result (19.2 mm). The peak and average tumor blood flow contrasts were 8.3-fold and 5.9-fold, respectively. Note that measurement noise caused some artifacts with $\mu_a^{total}(r, \tau)$ lower than static $\mu_a(r, \tau)$ in the region bordering the reconstructed tumor, leading to some negative flow values.

The second patient (P2) was a 49-year-old female, who had an a-typical ductal hyperplasia and low-grade carcinoma in situ. Ultrasound images [FIG. 27(d)] show that the lesion centroid was located at 13.3 mm beneath the skin surface with the dimension of 8.5×3.5 mm². Our ncDCT imaging results show a clear large tumor lesion with two small suspicious artificial anomalies [FIG. 27(e)]. The dimension of the reconstructed large tumor was approximately 12.3× 5.1 mm² [FIG. 27(f)] and its central depth was 12.4 mm beneath the breast surface, which fairly matched the ultrasound imaging result. The peak and average blood flow contrasts were 14.0-fold and 10.6-fold, respectively. Artifacts with negative flow values were also observed in the region bordering the reconstructed tumor.

The in vivo imaging results are consistent with our computer simulation results (in that the tumor central location can be accurately recovered when the tumor locates within the sensitive region of diffuse light.

Discussion and Conclusions

Since increased angiogenesis in breast tumor is commonly associated with blood flow increase, imaging of blood flow distribution in breast tissue is of great importance for tumor detection.[8] The recently developed ncDCT in our laboratory provides a unique imaging tool for noncontact detection of tumor blood flow contrasts.[21] We have previously demonstrated the ability of ncDCT for imaging blood flow contrast in tissue phantoms with a simple semi-infinite geometry.[21] The remaining challenge of applying ncDCT for breast tumor imaging includes translating the FEM-based imaging algorithm to breast-shaped geometry and handling potential problems arising from the in vivo measurements. The goal of this study is to demonstrate the feasibility and evaluate the accuracy of ncDCT in detecting breast tumors.

Computer simulations were used to investigate the origins of flow reconstruction discrepancies. From the simulations, we observed similar reconstruction accuracies in blood flow contrasts and tumor central locations with slab-shaped and breast-shaped boundaries (see FIG. 23 and Table 3), indicating the ability of ncDCT for reconstructing tumor flow contrast in human breast with irregular geometry. Further simulations on breast-shaped geometry evaluated reconstruction accuracies when tumors had different flow contrasts and located at different depths. The results suggested that the reconstructed tumor location and flow contrasts were more accurate when the tumor volume was within the sensitive region of diffuse light (see FIG. 24). Based on photon diffuse theory, the penetration depth of diffuse light is ~½ of the S-D separation.[35,38,39] The largest S-D separation of ncDCT was 30 mm, allowing for a penetration depth up to ~15 mm. As such, it was not surprising that the reconstruction errors increased as the tumor center located at a depth deeper than 10 mm. The S-D separation (associated with light penetration depth) and SNR are two inter-related parameters that affect the utility of ncDCT. Future study should explore using source fibers with larger diameter to deliver greater light intensity for promoting the SNR and penetration depth.

In contrast to the recovery of tumor location, the reconstruction of tumor blood flow contrasts was more complicated. The reconstructed peak BFIs were overestimated when the tumor located closer to the breast surface and underestimated when the tumor located out of the sensitive region of diffuse light [see FIG. 24(c)]. By contrast, the reconstructed average BFIs were consistently underestimated. These observations are similar to those in DOT for reconstruction of tumor absorption contrasts.[44,45] It is known from the DOT practice that imaging sensitivity is higher at the shallow region beneath tissue surface.[46] Therefore, the reconstructed peak BFI from a single node close to the tissue surface tends to be overestimated.

However, most of the reconstructed BFIs from the tumor node are prone to be underestimated due to the nature of inverse problem. Since the number of boundary data (S-D pairs) in ncDCT is much smaller than the unknowns to be solved (i.e., BFIs at all mesh nodes), the inverse problem is unstable,[47] leading to the underestimation.[44] In addition, according to the definition of $\mu_a^{total}(r, \tau) = \mu_a(r) + \mu_a^d(r, \tau)$, BFI reconstruction errors come from both "static" and "dynamic" absorption coefficients. Therefore, dynamic flow contrast errors may be further enlarged by attributing all reconstruction errors of $\mu_a^{total}(r, \tau)$ to dynamic $\mu_a^d(r, \tau)$ while ignoring static errors of $\mu_a(r)$.

Similar to our previous findings,[21] the relative changes of tumor flow contrasts can be accurately reconstructed in a large range of flow contrast variations [see FIGS. 24(d) and 24(e)]. The observed linear relationships with a slope of close to "1" indicate the ability of ncDCT to capture tumor blood flow changes, which can be potentially used to longitudinally monitor tumor hemodynamic responses to interventions.

As expected, adding noise reduced the reconstruction accuracies (see FIG. 25). However, tumors can still be reconstructed clearly from the boundary data with noise (see FIG. 25), indicating the feasibility of ncDCT for in vivo breast tumor detection. More importantly, adding a priori knowledge of the tumor volume and location improved significantly reconstruction accuracy (see FIG. 26), which agrees with previous observations in DOT.[37,40,42] The results from the two patients with low-grade carcinoma showed higher blood flow contrasts in the tumor regions compared to the surrounding tissues (see FIG. 27). The reconstructed positions of the two tumors on the x-y plane [see FIGS. 27(c) and 27(f)] agreed well with ultrasound imaging results [see FIGS. 27(a) and 27(d)]. The reconstructed tumor central depth from the second patient (P2) also matched the ultrasound image. For the first patient (P1), however, the reconstructed tumor central depth was at 10.8 mm beneath the breast surface, which did not match the ultrasound finding (19.2 mm). This was likely due to deep location of the tumor (P1), which was beyond the sensitive depth of diffuse light detected by our current system. To confirm this, we conducted computer simulations with the same location of tumor and similar level of measurement noise, and we found that the reconstructed tumor located at ~8.5 mm beneath the breast surface (data are not shown). The simulation result agrees well with our in vivo measurement result.

Due to the difficulty of coregistering the 2-D ultrasound image and 3-D ncDCT image, it was not possible in this study to apply the a priori structural knowledge of tumors for improving the accuracy of image reconstruction in patients. Future study may utilize 3-D anatomical imaging modalities, such as MRI or CT, to obtain accurate priori structural information of the tumor.

The average tumor-to-normal flow contrasts of 5.9- and 10.6-fold observed from the two carcinomas are comparable to previously reported flow contrasts of 2- to 10-fold in breast tumors detected by DCS.[10,11] It should be noted that the tumor flow contrasts quantified previously by DCS may be underestimated due to the partial volume effect by the healthy tissues surrounding the tumor. In addition, the potential crosstalk between $\mu_a$, $\mu_s'$, and BFI may also result in over- or underestimation of blood flow contrasts in both DCS and ncDCT.[33,35] According to the definition of $\mu_a^{total}$, $\mu_a$, $\mu_s'$, and $\alpha D_B$ variations cannot be completely separated unless they are independently measured. When assuming homogeneous $\mu_a$ and $\mu_s'$ over the entire breast, the realistic heterogeneous $\mu_a$ and $\mu_s'$ across the tumor can generate errors in tumor BFI contrasts. To overcome this limitation, a separate instrument enabling 3-D imaging of $\mu_a$ and $\mu_s'$ distributions in the breast is needed (e.g., a frequency domain or time-resolved DOT).[16,48-50]

In conclusion, this reports the first flow image reconstruction results in human breast tumors using a novel ncDCT system. Results from computer simulations suggest that relatively high accuracy can be achieved when the entire tumor was within the sensitive region of diffuse light. Image reconstruction with a priori knowledge of the tumor volume and location can significantly improve the accuracy in recovery of tumor blood flow contrasts. In vivo imaging results from the two breast carcinomas show higher blood flow contrasts in the tumor regions compared to the surrounding tissues, which are comparable with previous findings. The noncontact design of the ncDCT system has the potential to be used for imaging blood flow distributions in soft and vulnerable tissues without distorting tissue hemodynamics.

References: 1. Boyd et al., N. Engl. J. Med. 356(3), 227-236 (2007); 2. Nothacker et al., BMC Cancer 9(1), 335 (2009); 3. Beaney et al., Lancet 323(8369), 131-134 (1984); 4. Tafreshi et al., Cancer Control 17(3), 143-155 (2010); 5. Lindfors et al., Radiology 246(3), 725-733 (2008); 6. Prionas et al., Radiology 256(3), 714-723 (2010); 7. Avril et al., J. Clin. Oncol. 14(6), 1848-1857 (1996); 8. Vaupel et al., Cancer Res. 49(23), 6449-6465 (1989); 9. Kondepati et al., Anal. Bioanal. Chem. 390(1), 125-139 (2008); 10. Durduran et al., Opt. Lett. 30(21), 2915-2917 (2005); 11. Zhou et al., J. Biomed. Opt. 12(5), 051903 (2007); 12. Yu, J. Biomed. Opt. 17(1), 010901 (2012); 13. Choe et al., PloS One 9(6), e99683 (2014); 14. Ntziachristos et al., Neoplasia 4, 347-354 (2002); 15. Zhu et al., Radiology 237(1), 57-66 (2005); 16. Choe et al., J. Biomed. Opt. 14(2), 024020 (2009); 17. Tromberg et al., Med. Phys. 35(6), 2443-2451 (2008); 18. Zhu et al., Radiology 256(2), 367-378 (2010); 19. Fang et al., Radiology 258(1), 89-97 (2011); 20. Flexman et al., J. Biomed. Opt. 16(7), 076014 (2011); 21. Lin et al., Appl. Phys. Lett. 104(12), 121103 (2014); 22. Choe et al., IEEE J. Sel. Top. Quant. Electron. 18(4), 1367-1386 (2012); 23. Busch et al., PET Clin. 8(3), 345 (2013); 24. Boas et al., J. Opt. Soc. Am. A 14(1), 192-215 (1997); 25. Culver et al., J. Cereb. Blood Flow Metab. 23(8), 911-924 (2003); 26. Zhou et al., Opt. Express 14, 1125-1144 (2006); 27. Li et al., Sci. Rep. 3,1358 (2013); 28. Lin et al., J. Biomed. Opt. 17(1), 010502 (2012); 29. Dehghani et al., Commun. Numer. Methods Eng. 25(6), 711 (2009); 30. Durduran et al., NeuroImage 85(Pt 1), 51-63 (2014); 31. Dehghani et al., Phys. Med. Biol. 49(7), 1131-1145 (2004); 32. Koppel, Phys. Rev. A 10(6), 1938-1945 (1974); 33. Dong et al., IEEE Trans. Biomed. Eng. 60(2), 361-368 (2013); 34. Jermyn et al., J. Biomed. Opt. 18(8), 086007 (2013); 35. Irwin et al., Biomed. Opt. Express 2(7), 1969-1985 (2011); 36. Durduran et al., Rep. Prog. Phys. 73(7), 076701 (2010); 37. Dehghani et al., Appl. Opt. 42(16), 3117-3128 (2003); 38. Boas, Physics, p. 244, University of Pennsylvania, Philadelphia (1996); 39. Zhu et al., Appl. Opt. 40(19), 3288-3303 (2001); 40. Brooksby et al., J. Biomed. Opt. 10(5), 051504 (2005); 41. Yalavarthy et al., Opt. Express 15(13), 8043-8058 (2007); 42. Dehghani et al., Philos. Trans. Series A Math. Phys. Eng. Sci. 367(1900), 3073-3093 (2009); 43. Fantini et al., J. Opt. Soc. Am. B 11(10), 2128-2138 (1994); 44. Brooksby et al., IEEE J. Sel. Top. Quant. 9(2), 199-209 (2003); 45. Huang et al., Appl. Opt. 43(8), 1654-1662 (2004); 46. Dehghani et al., Appl. Opt. 48(10), D137-143 (2009); 47. Kabanikhin, J. Inverse Ill-Posed Probl. 16(4), 317-357 (2008).; 48. Ueda et al., Cancer Res. 72(17), 4318-4328 (2012); 49. Enfield et al., J. Biomed. Opt. 18(5), 056012 (2013); 50. Chen et al., J. Biomed. Opt. 9(3), 504-510 (2004).

Ex. 5: Speckle Contrast Diffuse Correlation Tomography of Complex Turbid Medium Flow Near-infrared (NIR) light enables the deep tissue investigation of microvascular hemodynamics.[1,2] Blood flow is one such available observable promoting a wealth of physiological insight both individually and in combination with other metrics. Diffuse correlation spectroscopy (DCS) and, to a lesser extent, tomography (DCT) have received interest over the past two decades as noninvasive methods for blood flow recovery.[3,4] In typical DCS implementations, the temporal fluctuations in individual speckles are measured by avalanche photodiodes (APDs) coupled to independent optical fibers.

These impose a physical and monetary overhead limiting the potential sampling density and temporal resolution. In our previous work, we extended DCS into a noncontact lens-based system succeeded by noncontact DCT (ncDCT) within a finite element method (FEM) framework.[1,5] These studies provided desirable operational attributes, especially the elimination of hemodynamic alterations due to contact compression and the ability to incorporate arbitrary tissue boundaries and compositions. Moreover, our FEM reconstruction method is based on readily available open source software for seamless integration of geometries and inversion algorithm techniques.[6] The mechanical scanning of an optical fiber array in ncDCT to cover a region of interest (ROI) provides one solution to increasing sampling density and reducing cost, but increases measurement duration and may introduce motion artifacts. Another solution we outline here, recruitment of charge-coupled device (CCD) detection, promotes advantages including increased sampling density, decreased sampling times and equipment overhead, and geometry extraction potential. CCD detection has frequently been utilized successfully in other flow monitoring techniques such as laser speckle contrast imaging.[7] This modality applies a wide-field illuminating source to enable rapid collection of two-dimensional images depicting spatial vessel flow variations on superficial tissues. There have been a few recent advancements toward blood flow monitoring in deep tissue with NIR point-source illumination and CCD detection. Diffuse speckle contrast analysis and speckle contrast optical spectroscopy approach the problem by using the relationship between a speckle contrast parameter and DCS theory.[8,9] Speckle contrast optical tomography (SCOT) extends the concept using an analytical Born approximation in the inverse problem on transmission based measurement of parallel-plane tissue phantoms.[10] We move forward from these studies in the direction of reflectance tomographic imaging by developing a robust technique combining the benefits of CCD detection and our FEM based DCT flow reconstruction. In contrast to SCOT which formulates the inverse problem with a direct analytical relationship between the speckle contrast and mean-square displacement of moving scatterers, we simplify the process by converting the speckle contrast to boundary flow indices and retaining our leverage of FEM-based DOT reconstruction advancements. Specifically, in this study we are able to take advantage of the nonlinear iterative algorithms, finite-element support functions, data filtering, and the many features included in the modified NIRFAST for DCT.[5] This is due to the formal similarity between DOT and DCT as outlined in our previous publication.[5] This unique method, termed speckle contrast DCT (scDCT), facilitates three-dimensional (3D) reflectance flow contrast imaging of complex turbid media. As this technique promotes incorporation of both heterogeneous optical properties and arbitrary tissue boundaries, scDCT can utilize highly representative sample characteristics in the recovery of accurate flow data. We apply this scDCT technique on a reflectance-based measurement which more adequately represents the situation encountered in larger subjects such as humans where transmission is not practical in most cases (due to the limited penetration depth of light), enhancing translatability. A smear correction algorithm is also incorporated in this study to resolve the influences on data uniquely incurred when using frame-transfer CCDs with the point-source illumination and reflectance setup.

Methods and Materials

As shown in FIG. 5(a), the scDCT equipment and experimental setup involve a 785 nm long coherence laser (coherence length>5 m, CrystaLaser, NV) to emit photons into the sample. A fiber optic switch (VX500, Dicon, CA) with fourchannel outputs delivered photons to four multimode optical fibers (FT200UMT, Thorlabs, NJ) individually. The fibers [S1-S4 in FIG. 5(b)] were located 1.5 cm from the field of view (FOV) edge centers. An electron-multiplying CCD (EMCCD; Cascade 1K, Photometrics, AZ) with a zoom lens (Zoom 7000, Navitar, N.Y.) aligned concentrically to the FOV detected the speckle patterns due to the diffused light. The focal length of the image lens was 35 mm, making the focal plane on the surface of the liquid phantom. An F number of 8 was chosen to ensure the speckle size satisfied the Nyquist sampling criteria.[11]

The application of DCS theory was applied as discussed herein. Reconstructions of the combined term, $\mu_a(r)+\mu_a^d(r,\tau)$, are then carried out in NIRFAST using the "Standard" options for a single wavelength and continuous-wave application. A median filter built into NIRFAST is used for phantom test reconstructions as it assists in stabilizing inherent experimental noise. This is because in real measurements the inverse problem is likely to generate odd solutions in a few nodes which may not be encountered with ideal simulation.[5,6] The median filter offers six-level smoothing from none to high (0-5) and we select level 2 in this study. The inverse problem is set up using modified-Tikhonov regularization with minimization with respect to optical properties and a biconjugate gradient stabilized iterative inversion scheme for Jacobian construction, as implemented in NIRFAST. The BFIs are then extracted from the reconstructed combined absorption coefficient using its definition above.

The speckle contrast with shot and dark correction were performed as discussed herein.

For physical experimentation, a liquid phantom provided a homogeneous tissue-like model by a mixture of distilled water, India ink (Black India, MA), and Intralipid (Fresenius Kabi, Sweden).[15] The property of real tissue was mimicked by setting $\mu_a$=0.05 cm$^{-1}$, $\mu'_s$=7.0 cm$^{-1}$, and $D_B$=1×10$^{-8}$ cm$^2$/s (assumed[15]). A cube-shaped solid phantom ($\mu_a$=0.05 cm$^{-1}$, $\mu'_s$=7.0 cm$^{-1}$, and $\alpha D_B$, was measured by DCS to be about three orders of magnitude lower than the liquid background) of carbon black, titanium dioxide, silicone with 7 mm side length was submerged to a 2 mm depth beneath the surface of the FOV center.

Results and Discussion

During both heterogeneity presence and absence experiments, the scDCT measurement protocol consisted of speckle contrast recovery over the liquid surface in a sequential manner for each of the four sources. For each source, 30 frames were acquired with an exposure time of 2 ms and frame rate of 8 frames/s. We defined 9×9 detectors centered in the FOV over 1.0×1.0 cm [FIG. 5(b)] surrounding the target surface. The resulting S-D separations were all 1.0-2.0 cm with 1.25 mm distance between detectors. Each detector (0.42×0.42 mm) included 3×3 windows and each window contained 7×7 pixels (8 μm pixel size). Measured speckle contrast was calculated per window and averaged across those corresponding to their associated detector.

Localized speckle contrast averages were then calculated along obtained frames. The homogeneous phantom was measured with scDCT first in the manner just described, followed by a standard DCS measurement for calibration purposes. Practically, the optical constant β is not available for measurement. A calibration factor was thus determined which equals to the ratio between speckle contrasts from scDCT and those calculated using Eq. (2) with the semi-infinite CDE analytical solution for g1 along with DCS (β=0.5) measured BFI on the homogeneous phantom.

FIG. 28(a) illustrates the intensity distribution with source S2 on the homogeneous phantom. FIG. 28(b) shows the distribution after desmearing, demonstrating a normal presentation for point-source intensity. To quantify the desmearing influence, we consider an array of detectors defined along the center row in line with the source location as shown relative to S2 in FIG. 28(a). The S-D ranges from 1.0 to 2.0 cm. For each remaining source the detectors are defined similarly, but with different orientation based on the source location. The measured K for such detectors and each source with and without desmearing is shown in FIG. 29(a), along with the calculated K. To refine this depiction, we increased effective detectors along the center row to 21 [see the ROI and dots in FIG. 29(a)] while defining them the same way as done elsewhere in the experimentation.

It can be seen that the desmeared K correlates with the calculation. The region of usable speckle contrast without desmearing is obviously limited with S2 most noticeably impacted. This is due to our system configuration in which frame transfer occurs in the direction from S2 to S4. The $D_B$ value across the center row of detectors is shown in FIG. 29(b). The $D_B$ value achieved from DCS at 2.0 cm S-D separation was 1.28×10$^{-8}$ cm$^2$/s. The independently averaged $D_B$ for S1-S4 at the 21 detectors were (1.19±0.05)×

Figure 30:
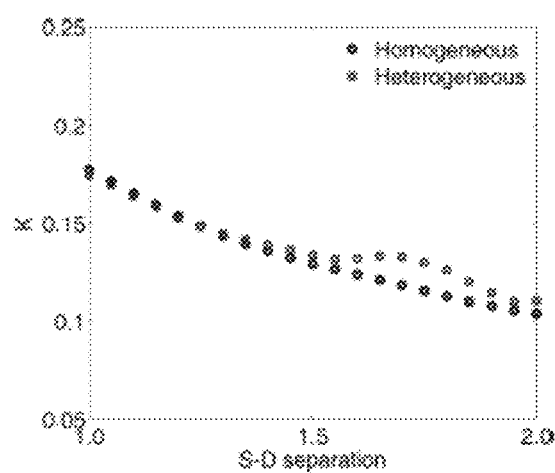
FIG. 30 shows results speckle contrast distributions from S1 on homogeneous and heterogeneous phantoms, measured by scDCT.
Figure 31:
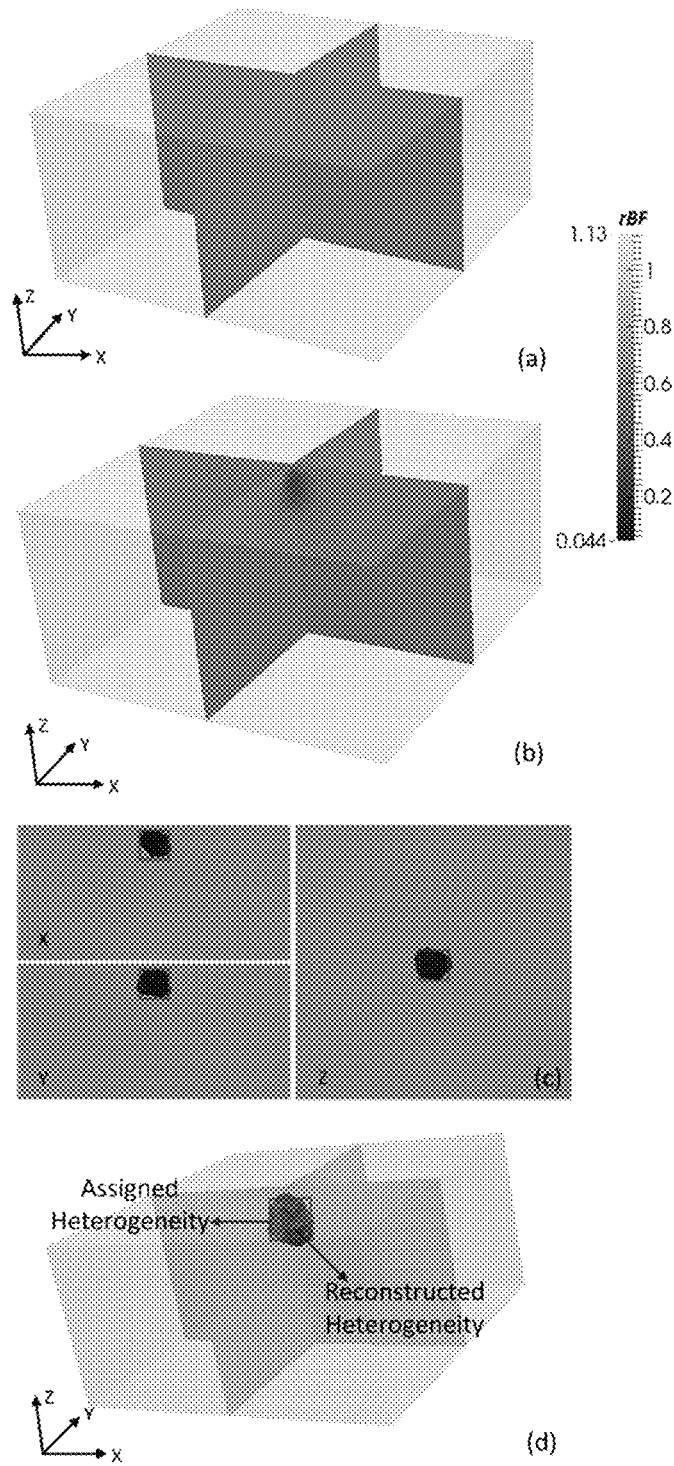
FIG. 31 shows reconstructed 3D flow contrasts measured by scDCT. Three-dimensional overlaid cross sectional views of the slab phantom (a) without heterogeneity and (b) with heterogeneity. (c) Two-dimensional cross-sectional view (x and y through side centers; z at 24.5) of the region with heterogeneity as extracted by half max contrast threshold criteria. The true region with heterogeneity is depicted by centered squares. (d) The extracted (half max contrast threshold) region with heterogeneity obtained by computer simulation. Images displayed with ParaView (Kitware, N.Y.).

$10^{-8}$ cm$^2$/s, $(1.18\pm0.08)\times10^{-8}$ cm$^2$/s, $(1.17\pm0.06)\times10^{-8}$ cm$^2$/s, and $(1.13\pm0.06)\times10^{-8}$ cm$^2$/s. These are in good agreement (within 12%) with the standard DCS measurement. The comparison of K distributions measured from S1 on the homogeneous and heterogeneous phantoms is shown in FIG. 30.

Next, we measured speckle contrast in the phantom with heterogeneity. The corresponding boundary BFIs were combined with the BFI obtained from the homogeneous phantom measurements for image reconstructions. We used a finite element mesh [dimension(mm): 60(H)×60(W)×30(D)] centered at (0,0,15) with a 3 mm node distance.[5] The mesh was refined in the known region of heterogeneity to improve detection resolution while not overwhelmingly increasing the number of nodes. Refinement was within a 15 mm radius (e.g., inclusive of five elements) centered from (0,0,30) to a 1.5 mm node distance (total nodes: 10 307) using ANSYSR (ANSYS, PA). The relative blood flow, rBF, is used to denote the ratio of phantom with heterogeneity to homogeneous phantom $\alpha D_B$'s. As presented in our previous work,[5] the algorithm based on an open software package NIRFAST[6] was used to reconstruct rBF in 3D. The reconstructed image from homogeneous phantom and heterogeneous phantom is shown in FIGS. 31(a) and 31(b). A reconstructed heterogeneity was clearly recognizable from the overlaid cross-sections compared between the two images. FIG. 31(c) shows cross sectional views of the heterogeneity extracted by half max contrast threshold criteria. The averaged heterogeneity rBF was 0.38 with center (0.0, −0.1, 25.0) close to the actual center (0, 0, 24.5). Reconstructed heterogeneity side length was 7.2 mm with dimensions that were accurate compared to the true solid phantom. We likewise simulated the phantom experiment by computer using identical parameters. The region with heterogeneity extracted by half max contrast threshold is shown in FIG. 31(d). The reconstructed heterogeneity averaged rBF was 0.37 with center (−0.1, 0.0, 24.0), similar to phantom results (averaged rBF within 3% of phantom test results). Corresponding 3D flow distributions were also similar to the phantom experiment [FIG. 31(b)] and hence are not shown. We also performed two simulations with off-center locations, but otherwise similar setup, of the heterogeneity and found the reconstructed center and side length in agreement with the expectation.

In this study, an exposure time of 2 ms was selected to achieve a good contrast to noise ratio.[16] The reconstruction and boundary data parameters of delay time t and window size used herein have been discussed in detail elsewhere.[5,11] We acknowledge that static scatterer contributions can degrade the current model. Ideally, recovered rBF would be zero. However, we only sought to validate 3D flow contrast detection using our new scDCT method rather than optimize flow recovery accuracy, and we produced sufficient contrast to identify and characterize the anomalous presence. The agreement between scDCT and DCS on a homogeneous phantom and between simulation and phantom in heterogeneity detection supports success. Furthermore, multiple two-dimensional S-D pairs provided by the CCD omit the probe scanning in ncDCT,[5] and thus significantly improve the spatial and temporal resolution. In addition, due to decreasing signal with increased S-D separation using a point source we were limited to at most 2.2 cm after noise correction. Nevertheless, this S-D separation is still capable of probing tissues ~1 cm depth. We also note that although the FEM framework allows incorporating complex heterogeneities and boundaries, we chose to exemplify our technique in a straightforward setup.

Further difficulties may be encountered when extending scDCT to real complex media. For example, surface curvature may result in modified light distributions and S-D separations potentially reducing the accuracy and reliability of reconstructed flow contrasts. These issues are beyond the scope of the current paper, but can be addressed in the future through computer simulations, possible free-space corrections,[17] and telecentric zoom lens incorporation.[18,19]

Conclusions

We reported a cost-effective CCD-based reflectance 3D flow imaging system from laser speckle contrast with four target-contacted fibers serving as point sources. Beyond dark and shot noise corrections, we successfully incorporated an additional desmearing algorithm. This correction was found to be imperative for reflectance applications using a point source to obtain accurate deep tissue speckle contrast.

Flow contrast was extracted using the relationship between a correlation diffusion equation solution and the speckle contrast. A FEM-based DCT framework was employed to reconstruct spatially distributed blood flow. This system was validated using a reflectance-based measurement on a liquid phantom with an internally placed heterogeneity. Compared to our previous ncDCT design,[5] this system demonstrated potential for fast and dense boundary data acquisition and deep tissue hemodynamics tomography translating directly to human studies (e.g., burn/ulcerous tissue flow detection).

References: 1 Lin et al., J. Biomed. Opt. 17, 010502 (2012); 2 Yu et al., Curr. Med. Imaging Rev. 8, 194-210 (2012); 3 Boas et al., J. Opt. Soc. Am. A 14, 192-215 (1997); 4 Zhou et al., Opt. Express 14, 1125-1144 (2006); 5 Lin et al., Appl. Phys. Lett. 104, 121103 (2014); 6 et al., Commun. Numer. Methods Eng. 25, 711-732 (2008); 7 et al., Opt. Commun. 37, 326-330 (1981); 8 Bi et al., Opt. Lett. 38, 1401-1403 (2013); 9 Valdes et al., Biomed. Opt. Express 5, 2769-2784 (2014); 10 Varma et al., Biomed. Opt. Express 5, 1275-1289 (2014); 11 Boas et al., J. Biomed. Opt. 15, 011109 (2010); 12 Bandyopadhyay et al., Rev. Sci. Instrum. 76, 093110 (2005); 13 Ruyten, Opt. Lett. 24, 878-880 (1999); 14 Yuan, Ph.D. thesis, Tufts University, M A, 2008; 15 Irwin et al., Biomed. Opt. Express 2, 1969-1985 (2011); 16 Yuan et al., Appl. Opt. 44, 1823-1830 (2005); 17 Ripoll et al., Phys. Rev. Lett. 91, 103901 (2003); 18 Zhang et al., Opt. Eng. 49, 053001 (2010); 19 Watanabe et al., IEEE Trans. Pattern Anal. Mach. Intell. 19, 1360-1365 (1997).

Ex. 6: nc_scDCT Test in Tissue Phantom and Human Forearm

Figure 32:
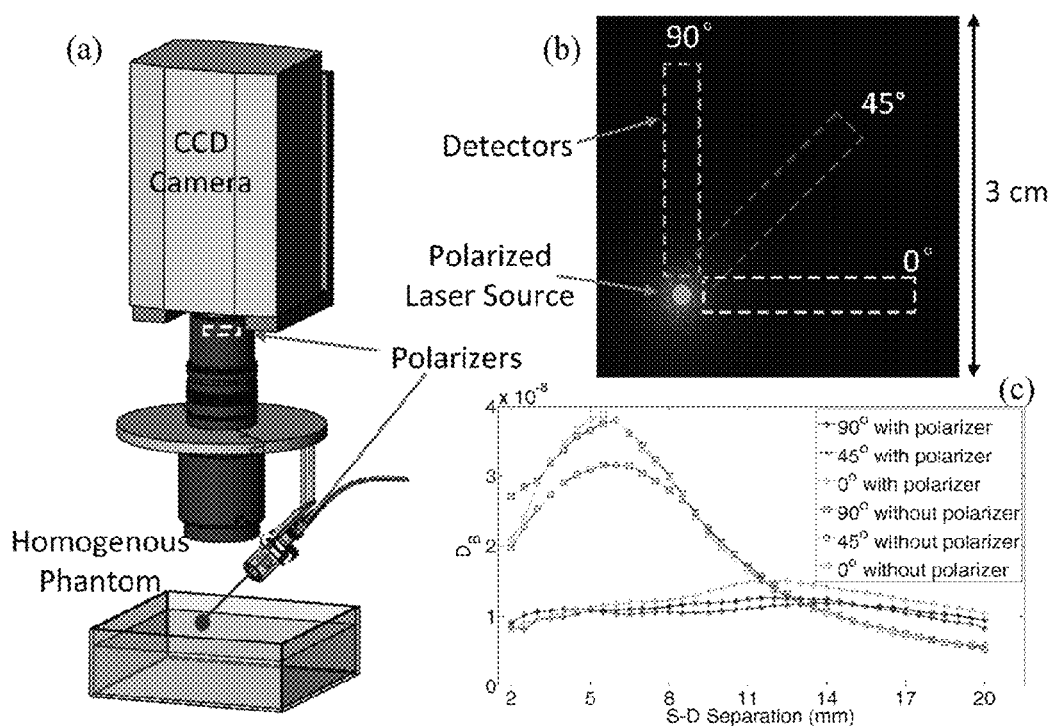
FIG. 32 shows phantom test results measured by the nc_scDCT. (a) The point laser source (785 nm) and CCD were focused onto a homogenous liquid phantom surface. (b) Configuration of the point source and 37 detectors on the CCD inside the FOV (c) Comparison of flow indices measured at multiple detectors with or without polarizers crossing the source and detectors.

The fully noncontact speckle contrast diffuse correlation tomography nc_scDCT system integrated with a crossed pair of polarizers (FIG. 32(a)) was tested in the homogenous tissue phantom with source and detectors pattern in FIG. 32(b). FIG. 32(c) suggests the reflectance nc_scDCT can produce homogenous flow index in homogenous phantom.

Figure 33:
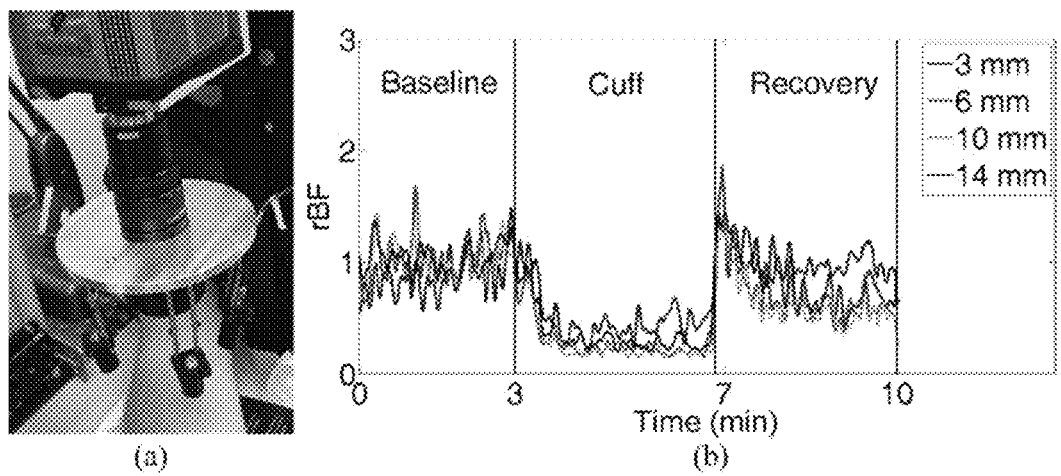
FIG. 33 shows in vivo test results in a human forearm measured by the nc_scDCT. (a) The point laser source (785 nm) and CCD were focused onto the surface of forearm. (b) Blood flow responses in forearm during 4-minute arterial cuff occlusion measured by the nc_scDCT with source-detector (S-D) separations of 3, 6, 10, and 14 mm.

The spectroscopic version of nc_scDCT system has been tested on a human forearm. Protocol included 3-minute baseline, 4-minute arterial occlusion and 3-minute recovery. Flow index of each point were normalized to the mean value of the baseline. FIG. 33(a) shows the experimental setup. FIG. 33(b) shows the relative blood flow (rBF) of four S-D distances (3 mm, 6 mm, 10 mm, 14 mm).

Figure 34:
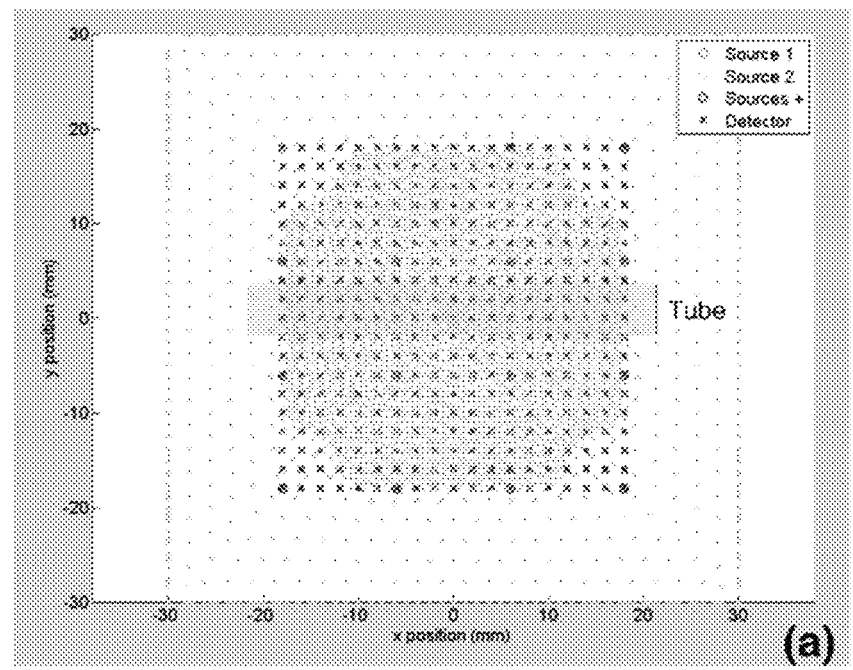
FIG. 34 shows results using nc_scDCT probe (a) on a homogeneous slab phantom background with internally placed tube-shaped anomaly of varied flow contrast (b).
Figure 34:
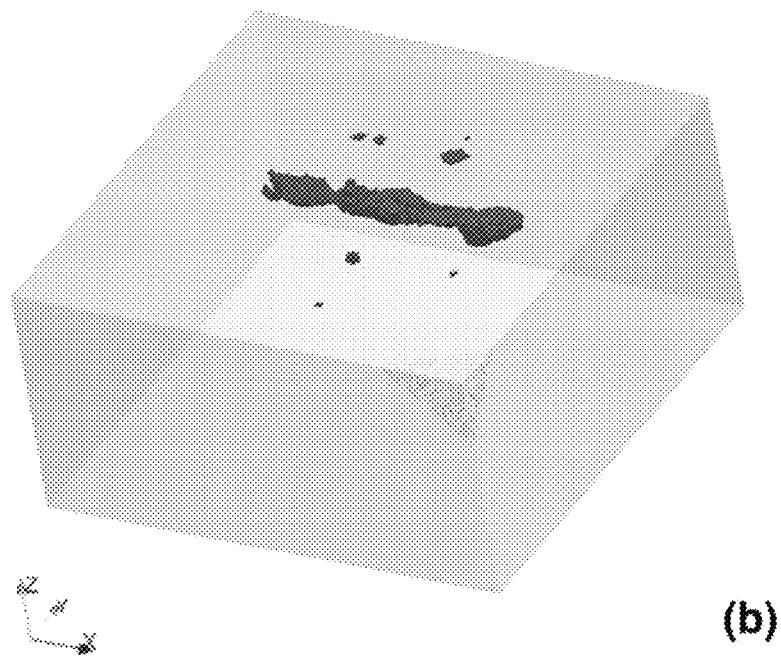

The nc_scDCT system integrated with Galvo mirror was tested on liquid tissue phantom. FIG. 34(a) shows the pattern of sources and detectors; 16 sources and 361 detectors were evenly distributed in an ROI of 3.6 cm$^2$. A pump-connected 6 mm diameter cylindrical tube anomaly was filled with liquid and small pieces of solid phantom, and was placed 2 mm beneath the liquid surface. The pump speed was set as 60 ml/min. The CCD camera captures image at each source position at 10 ms exposure time. FIG. 34b shows the reconstructed heterogeneity anomaly, which agrees with the setup. To the best of our knowledge, this is the first 3-D flow image generated by a reflectance nc_scDCT.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled. All documents referenced herein including patents, patent applications and journal articles and hereby incorporated by reference in their entirety.

We claim:

1. An optical method for three-dimensional (3-D) reflectance imaging of blood flow distribution in deep tissue of up to about 1.5 cm with an arbitrary tissue geometry comprising:
    projecting/focusing an imaging probe comprising long-coherence laser sources and a detector array on a tissue surface of a subject;
    applying source beams of near-infrared light to the tissue through a set of optical lenses;
    detecting diffused near-infrared light reflected from the tissue surface through a second set of optical lenses by a detector array and
    constructing a 3-D image based on a data set comprising measured diffused near-infrared light from the detector array,
    wherein the sources and the detector array are not in physical contact with the tissue.

2. The method of claim 1, wherein the detector array comprises a one-dimensional (1-D) array of avalanche photodiodes.

3. The method of claim 1, wherein the detector array comprises a two-dimensional (2-D) array of avalanche photodiodes.

4. The method of claim 1, wherein the imaging probe is affixed to a motorized stage such that the probe can be systematically and automatically moved across a region of interest of the tissue.

5. The method of claim 1, wherein the probe is focused through a wound, surgical opening, or a tissue flap within the subject.

6. The method of claim 1, wherein the 3-D image is reconstructed through a system that applies a finite-element-method from the measured data set.

7. An optical method for 3-D imaging of blood flow distribution in deep tissue of up to approximately 1.5 cm with an arbitrary tissue geometry comprising:
    applying near-infrared light through source fibers to borders of a region of interest of a tissue of a subject;
    detecting the near-infrared diffused light through an optical lens coupled to a charge-coupled-device (CCD), wherein adjustable optical zoom lenses provide a focal length and varied field of view such that the region of interest is covered by the 2-D array of detectors provided by the CCD; and,
    constructing an image based on a data set comprising measured diffused near-infrared light from the 2-D array of detectors provided by the CCD.

8. The method of claim 7, wherein the source fibers are not in contact with the subject and further wherein the source fibers are projected onto tissue surface using adjustable optical zoom lenses.

9. The method of claim 8, wherein the near infrared light is projected to the tissue by redirection using a Galvo mirror.

10. The method of claim 7, wherein the charge-coupled-device along with the sources is connected to a motorized stage such that the probe can be systematically moved across a region of interest of the tissue.

11. The method of claim 7, wherein the image is constructed through a system that applies a finite-element-method from the measured data set.

* * * * *